United States Patent
Zhang et al.

(10) Patent No.: US 8,426,430 B2
(45) Date of Patent: Apr. 23, 2013

(54) QUINAZOLINE DERIVATIVES

(75) Inventors: Weihan Zhang, Pudong (CN); Wei-Guo Su, Shanghai (CN); Haibin Yang, Shanghai (CN); Yumin Cui, Shanghai (CN); Yongxin Ren, Shanghai (CN); Xiaoqiang Yan, Nan Hui (CN)

(73) Assignee: Hutchison Medipharma Enterprises Limited, Nassau (BS)

( * ) Notice: Subject to any disclaimer, the term of this patent is extended or adjusted under 35 U.S.C. 154(b) by 1020 days.

(21) Appl. No.: 12/164,610

(22) Filed: Jun. 30, 2008

(65) Prior Publication Data

US 2010/0009958 A1 Jan. 14, 2010

(51) Int. Cl.
*A01N 43/54* (2006.01)
*A61K 31/517* (2006.01)
*C07D 239/72* (2006.01)

(52) U.S. Cl.
USPC .................................. 514/266.4; 544/293

(58) Field of Classification Search .................. None
See application file for complete search history.

(56) References Cited

U.S. PATENT DOCUMENTS

| | | | |
|---|---|---|---|
| 5,457,105 | A | 10/1995 | Barker |
| 6,235,741 | B1 | 5/2001 | Bilodeau et al. |
| 6,723,726 | B1 | 4/2004 | Cockerill et al. |
| 2003/0149041 | A1 | 8/2003 | Erickson et al. |
| 2004/0092750 | A1 | 5/2004 | Hasegawa et al. |
| 2006/0247262 | A1 | 11/2006 | Baenteli et al. |

FOREIGN PATENT DOCUMENTS

| | | | |
|---|---|---|---|
| CA | 2086968 | * | 7/1993 |
| EP | 0 566 226 | | 10/1993 |
| EP | 1154774 | | 6/2005 |
| NZ | 535109 | | 5/2006 |
| WO | WO 96/09294 | | 3/1996 |
| WO | WO 99/06378 | | 2/1999 |
| WO | WO 99/24037 | | 5/1999 |
| WO | WO 01/98277 | | 12/2001 |
| WO | WO 02/50043 | | 6/2002 |
| WO | WO02/68396 | * | 6/2002 |
| WO | 03/063794 | | 8/2003 |
| WO | WO 03/066060 | | 8/2003 |
| WO | 2004/014382 | | 2/2004 |
| WO | WO 2004/105765 | | 12/2004 |
| WO | 2005/009978 | | 2/2005 |
| WO | 2005/026158 | | 3/2005 |
| WO | 2005/063739 | | 7/2005 |
| WO | 2006/071017 | | 7/2006 |
| WO | 2006/071079 | | 7/2006 |
| WO | 2006/138304 | | 12/2006 |
| WO | WO 2008/034776 | | 3/2008 |

OTHER PUBLICATIONS

PCT Notification Concerning Transmittal of International Preliminary Report on Patentability and the Written Opinion of the International Searching Authority, mailed Jan. 13, 2011, in International Application No. PCT/US2009/049182.
PCT Notification of Transmittal of the International Search Report and the Written Opinion of the International Searching Authority, or the Declaration, mailed Feb. 9, 2010, in International Application No. PCT/US2009/049182.
Extended European Search Report dated Apr. 5, 2012, for European Patent Application No. 09774296.9.
Verma et al. "Substituted Aminobenzimidazole Pyrimidines as Cyclin-Dependent Kinase Inhibitors" Bioorganic & medicinal Chemistry Letters, 15(8), 2005, 1973-1977, 5 pages.
Zhang et al. "Discovery of EGFR Selective 4,6-Disubstituted Pyrimidines from a Combinatorial Kinase-Directed Heterocycle Library," J.AM. Chem. Soc. 2006, 128, 2182-2183.

* cited by examiner

*Primary Examiner* — Jeffrey Murray
(74) *Attorney, Agent, or Firm* — Finnegan, Henderson, Farabow, Garrett & Dunner, LLP

(57) ABSTRACT

Quinazoline derivatives of the following formula:

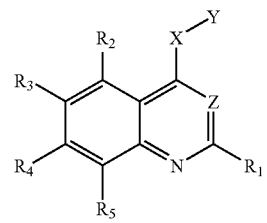

wherein $R_1$, $R_2$, $R_3$, $R_4$, $R_5$, X, Y, and Z are defined herein. It also discloses a method of treating cancer with one of these compounds.

10 Claims, No Drawings

QUINAZOLINE DERIVATIVES

BACKGROUND

Binding of epidermal growth factor (EGF) to epidermal growth factor receptor (EGFR) activates tyrosine kinase activity and thereby triggers reactions that lead to cellular proliferation. Overexpression and overactivity of EGFR could result in uncontrolled cell division—a predisposition for cancer. See, e.g., Science, 2004, 304:1497-1500.

Compounds that inhibit the overexpression and overactivity of EGFR are therefore potential candidates for treating cancer.

SUMMARY

This invention is based on the discovery that a number of quinazoline compounds inhibit the activity of EGFR.

One aspect of this invention relates to compound of the following formula:

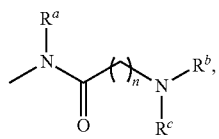

in which each of $R_1$, $R_2$, and $R_5$, independently, is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl; one of $R_3$ and $R_4$ is

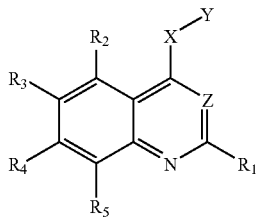

in which n is 1, 2, 3, 4, or 5; each of $R^a$, $R^b$, and $R^c$, independently, is H, alkyl, alkenyl, alkynyl, cycloalkyl, heterocycloalkyl, aryl, or heteroaryl, or $R^b$ and $R^c$, together with the nitrogen atom to which they are attached, form a 3-12 membered saturated, unsaturated, or aromatic ring containing 1-3 heteroatoms selected from N, O and S; and each of $R^d$ and $R^e$, independently, is H, alkyl, alkenyl, or alkynyl; or $R^d$ and $R^e$, together with the nitrogen to which they are attached, form a 3-12 membered saturated, unsaturated, or aromatic ring containing 1-3 heteroatoms selected from N, O, and S; and the other of $R_3$ and $R_4$ is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl; X is O, S, or $NR^f$, wherein $R_f$ is H, alkyl, alkenyl, alkynyl, aryl, cycloalkyl, heterocycloalkyl, heteroaryl, alkylcarbonyl, alkoxycarbonyl, aminocarbonyl, or aminosulfonyl; Y is phenyl optionally substituted with halo, nitro, cyano, alkyl, alkenyl, or akynyl, or optionally fused with another 3-8 membered ring, or Y is alkyl substituted with phenyl, which is optionally substituted with halo, nitro, cyano, alkyl, alkenyl, or akynyl, or optionally fused with another 3-8 membered ring; and Z is N or C—CN.

Referring to the above formula, a subset of the compounds feature that one of $R_3$ and $R_4$ is

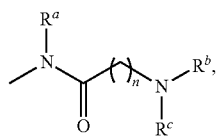

in which n is 1 and each of $R^a$, $R^b$, and $R^c$, independently, is H, alkyl, alkenyl, alkynyl, cycloalkyl, heterocycloalkyl, aryl, or heteroaryl.

Another subset of the compounds feature that one of $R_3$ and $R_4$

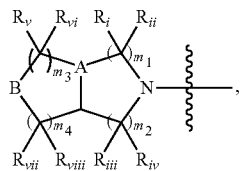

in which n is 1 or 2; $R^a$ is H, alkyl, alkenyl, alkynyl, cycloalkyl, heterocycloalkyl, aryl, or heteroaryl; and $R^b$ and $R^c$, together with the nitrogen atom to which they are attached, form a 3-12 membered saturated, unsaturated, or aromatic ring containing 1-3 heteroatoms selected from N, O and S. In some of the compounds, $R^b$ and $R^c$, together with the nitrogen atom to which they are attached, form a bicyclic ring of the following formula:

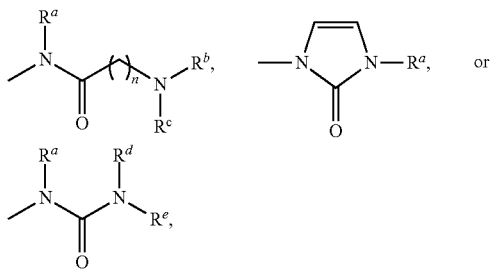

in which each of $m_1$, $m_2$, $m_3$, and $m_4$, independently, is 0, 1, 2, or 3; A is N or CR; B is NR or CRR', each R and R', independently, being H, alkyl, or halo; and each of $R_i$, $R_{ii}$, $R_{iii}$, $R_{iv}$, $R_v$, $R_{vi}$, $R_{vii}$, and $R_{viii}$, independently, is H, alkyl, or halo.

Still another subset of the compounds feature that one of $R_3$ and $R_4$ is

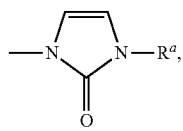

in which $R^a$ is H, alkyl, alkenyl, alkynyl, cycloalkyl, heterocycloalkyl, aryl, or heteroaryl.

Still another subset of the compounds feature that one of $R_3$ and $R_4$ is

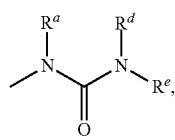

in which $R^a$ is H, alkyl, alkenyl, alkynyl, cycloalkyl, heterocycloalkyl, aryl, or heteroaryl; and each of $R^d$ and $R^e$, independently, is H, alkyl, alkenyl, or alkynyl; or $R^a$ is H, alkyl, alkenyl, or alkynyl; and $R^d$ and $R^e$, together with the nitrogen to which they are attached, form a 3-12 membered saturated, unsaturated, or aromatic ring containing 1-3 heteroatoms selected from N, O, and S.

Further another subset of the compounds feature that X is O, NH, or N—CH$_3$; Z is N; or Y is

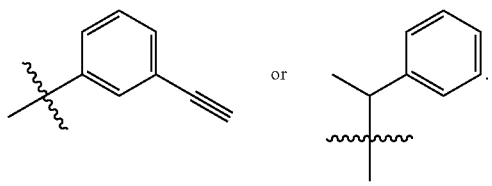

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl.

The term "alkenyl" herein refers to a $C_{2-10}$ straight or branched hydrocarbon, containing one or more C=C double bonds. Examples of alkenyl groups include, but are not limited to, vinyl, 2-propenyl, and 2-butenyl.

The term "alkynyl" herein refers to a $C_{2-10}$ straight or branched hydrocarbon, containing one or more C≡C triple bonds. Examples of alkynyl groups include, but are not limited to, ethynyl, 2-propynyl, and 2-butynyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocycloalkyl" refers to a nonaromatic 3-8 membered monocyclic, 8-12 membered bicyclic, or 11-14 membered tricyclic ring system having one or more heteroatoms (such as O, N, or S). Examples of heterocycloalkyl groups include, but are not limited to, piperazinyl, pyrrolidinyl, dioxanyl, morpholinyl, and tetrahydrofuranyl. Heterocycloalkyl can be a saccharide ring, e.g., glucosyl.

Alkyl, alkenyl, alkynyl, cycloalkyl, heterocycloalkyl, aryl, heteroaryl, and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, heterocycloalkyl, in which alkyl, alkenyl, alkynyl, alkyloxy, aryl, heteroaryl cycloalkyl, and heterocycloalkyl may further substituted.

The quinazoline compounds described above include their pharmaceutically acceptable salts, solvate, and prodrug, if applicable.

Examples of the compounds of this invention are shown below:

Compound 1

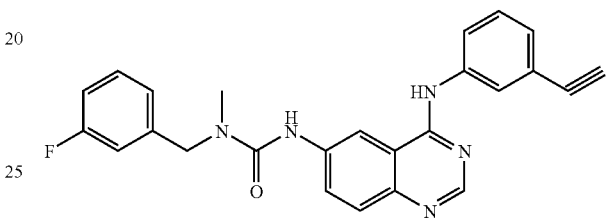

Compound 2

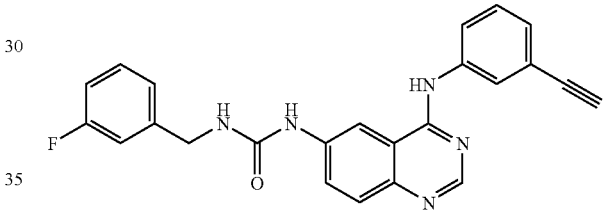

Compound 3

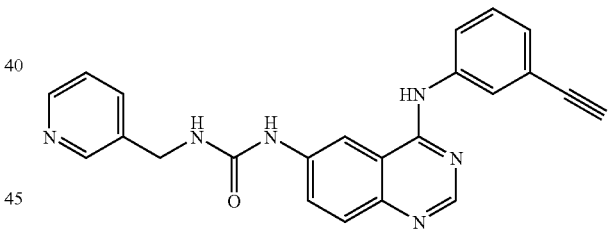

Compound 4

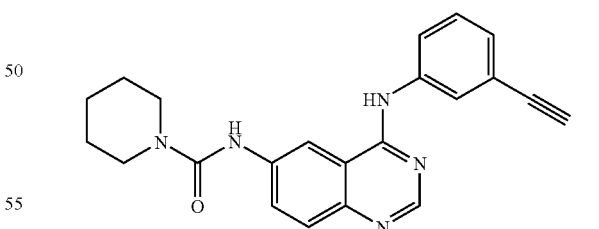

Compound 5

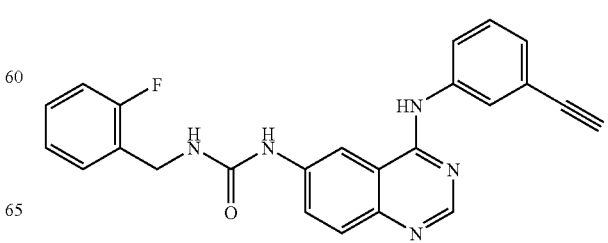

Compound 6
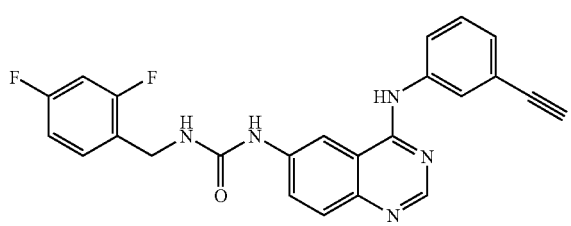
Compound 7
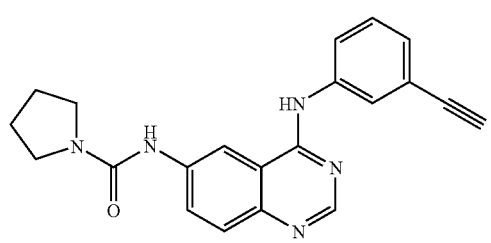
Compound 8
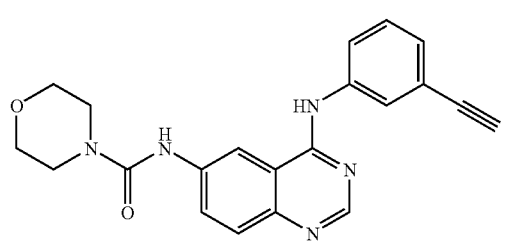
Compound 9
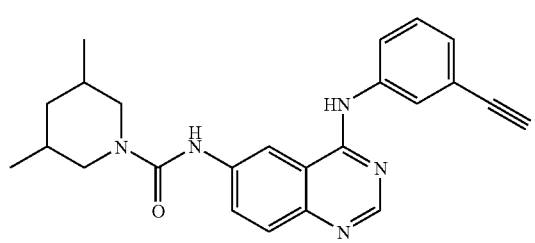
Compound 10
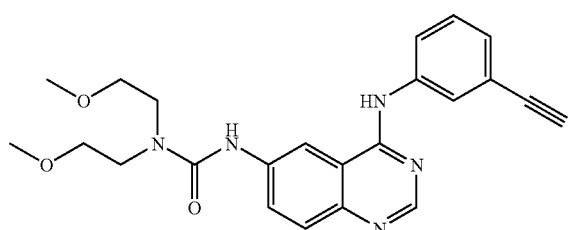
Compound 11
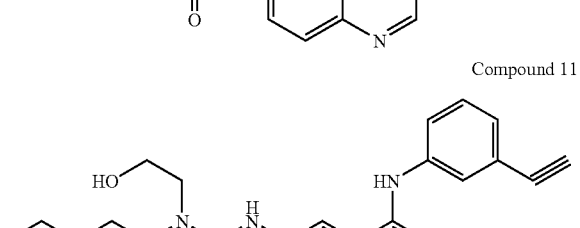
Compound 12
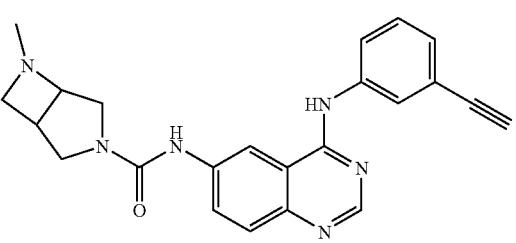
Compound 13
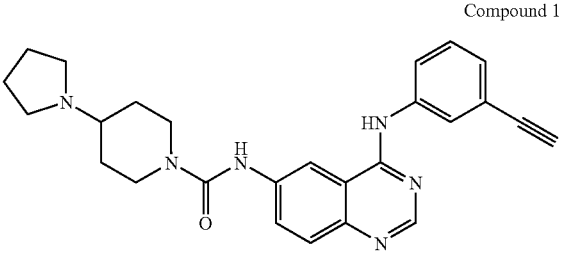
Compound 14
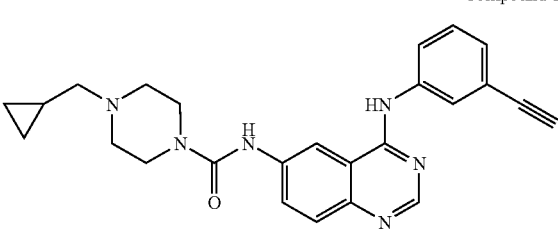
Compound 15
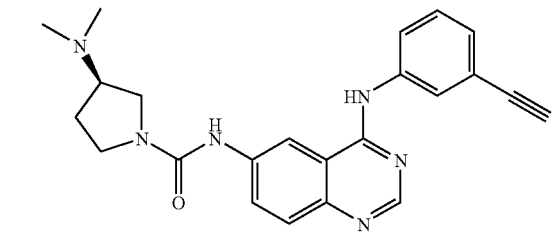
Compound 16
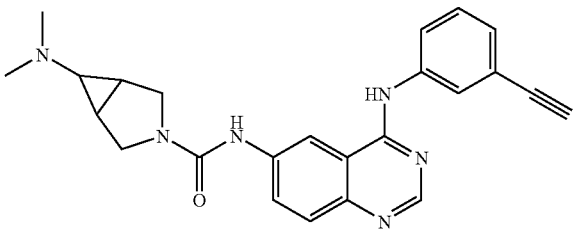
Compound 17
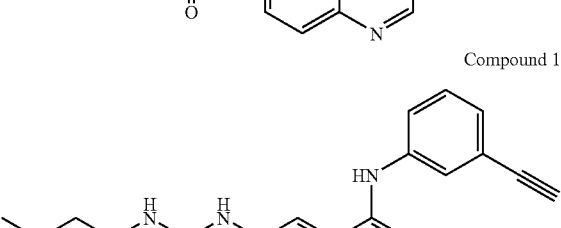

Compound 18
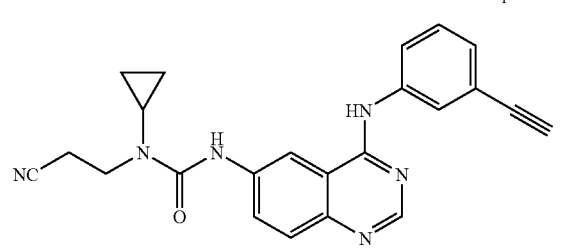
Compound 19
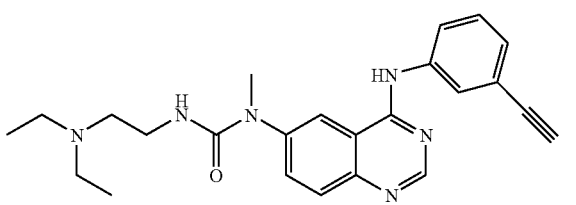
Compound 20
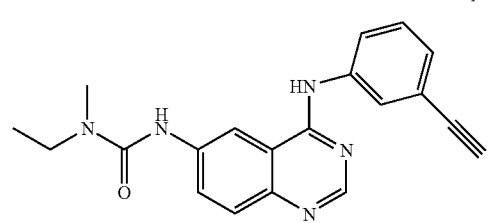
Compound 21
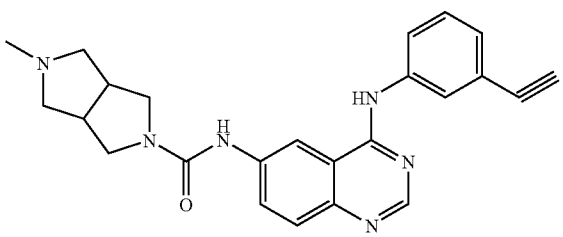
Compound 22
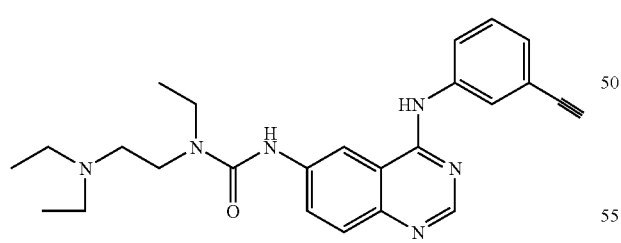
Compound 23
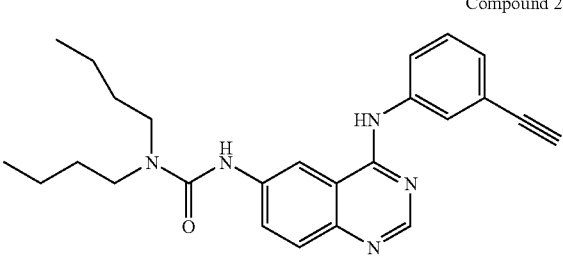
Compound 24
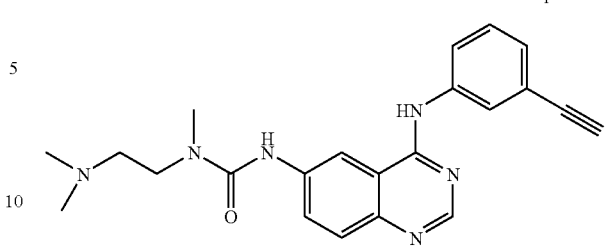
Compound 25
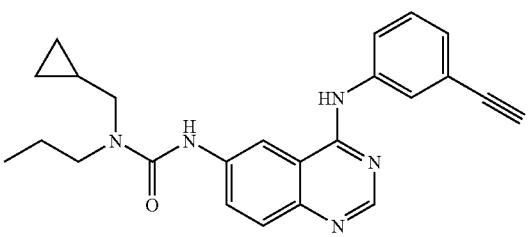
Compound 26
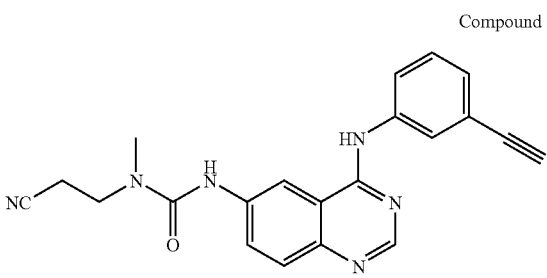
Compound 27
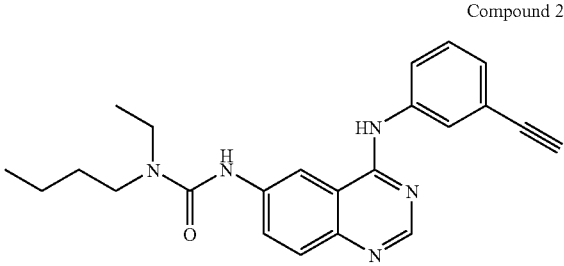
Compound 28
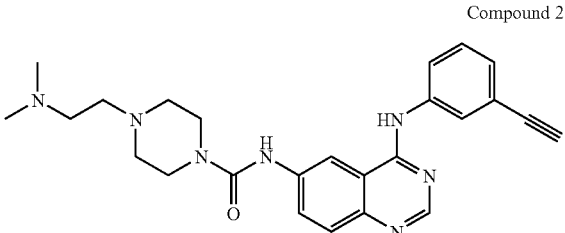
Compound 29
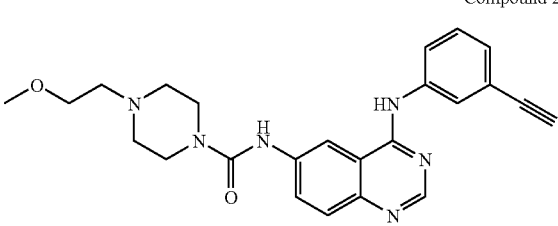

Compound 30
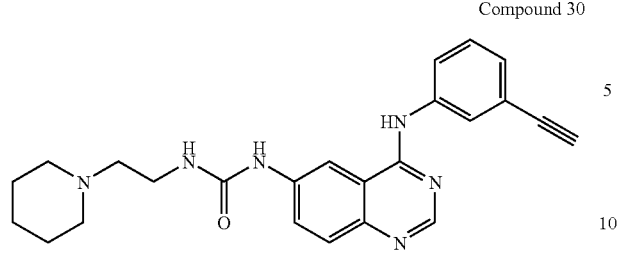
Compound 31
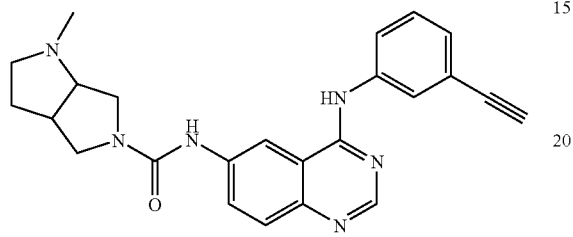
Compound 32
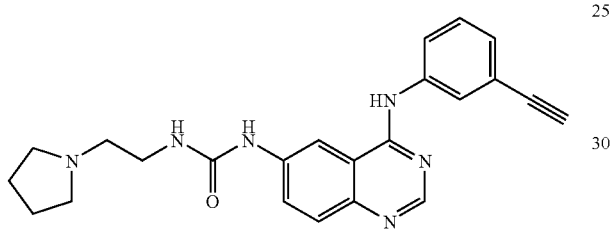
Compound 33
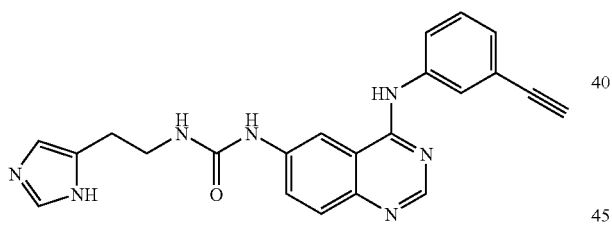
Compound 34
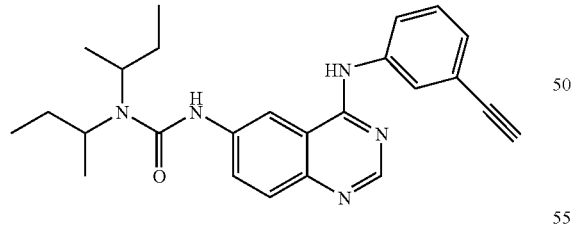
Compound 35
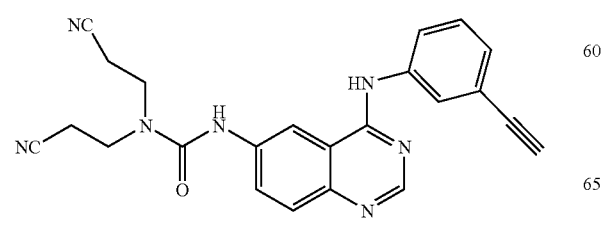
Compound 36
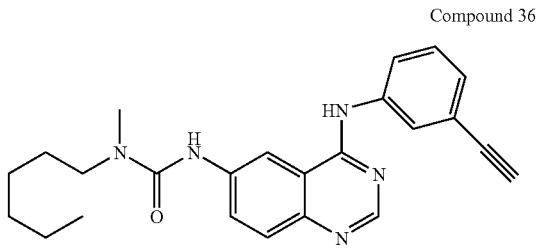
Compound 37
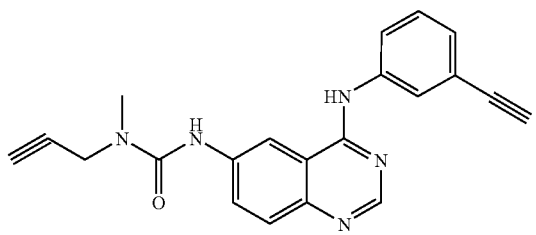
Compound 38
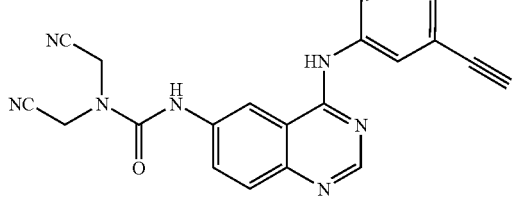
Compound 39
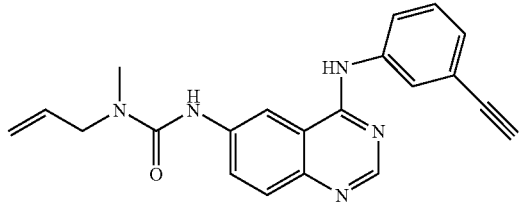
Compound 40
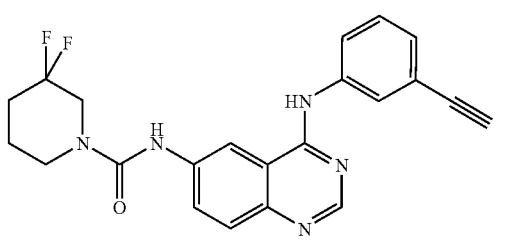
Compound 41
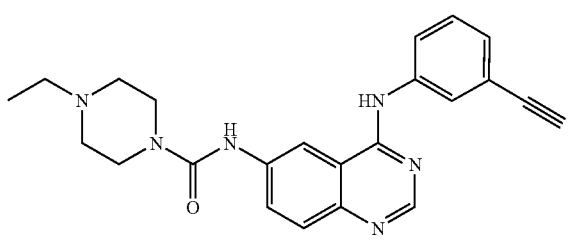

Compound 42
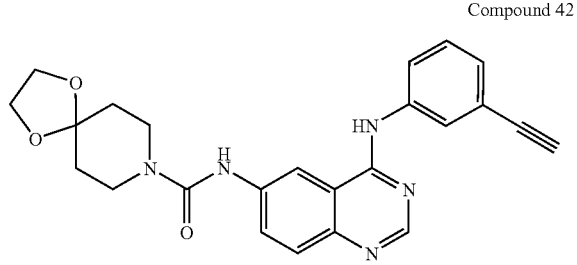
Compound 43
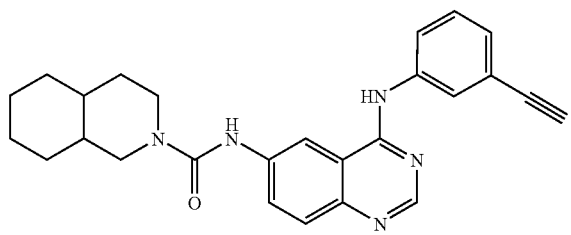
Compound 44
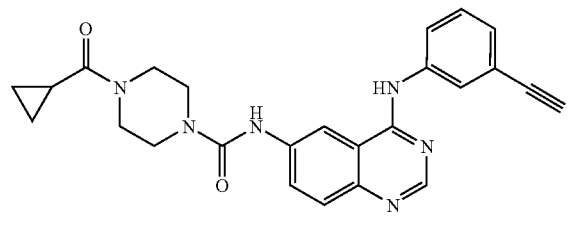
Compound 45
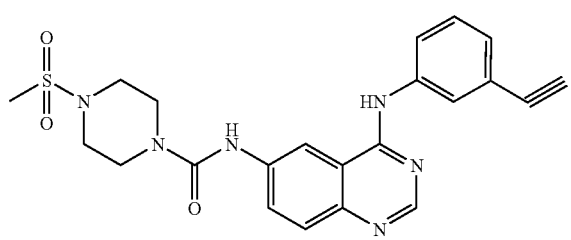
Compound 46
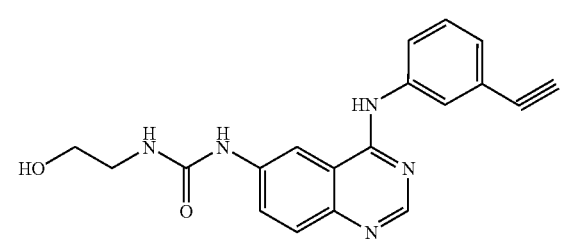
Compound 47
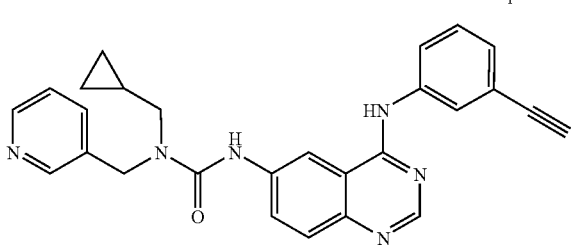
Compound 48
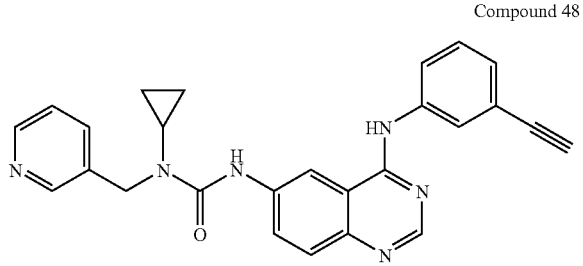
Compound 49
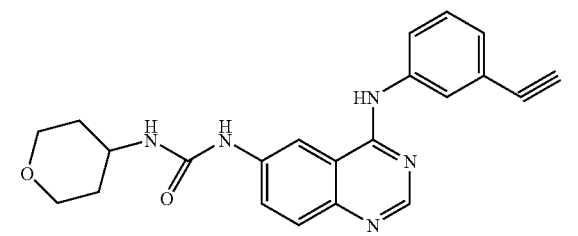
Compound 50
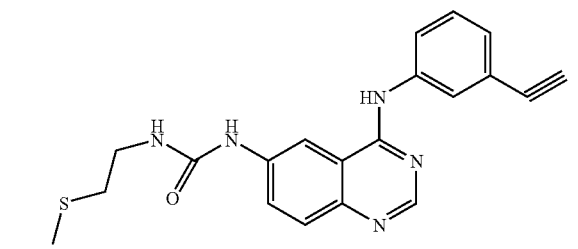
Compound 51
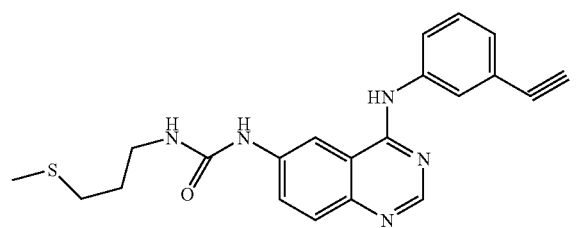
Compound 52
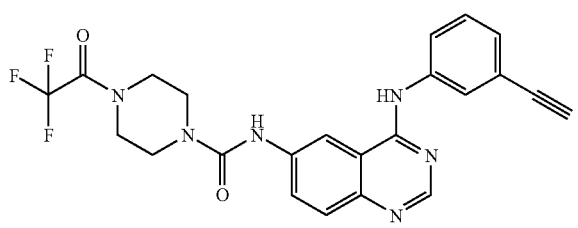
Compound 53
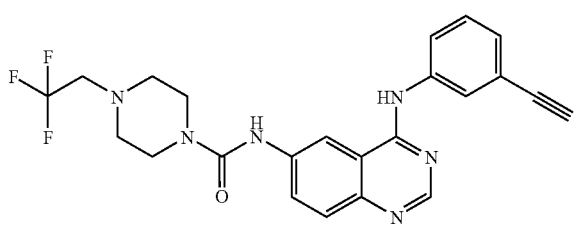

Compound 54
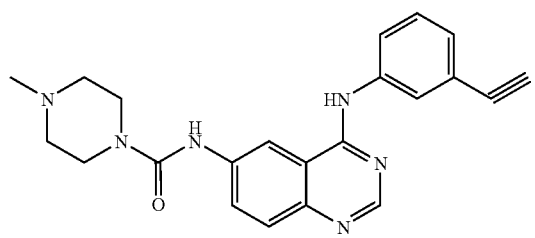
Compound 55
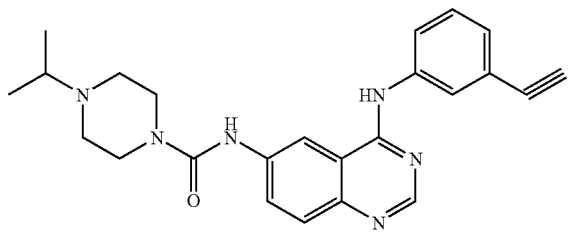
Compound 56
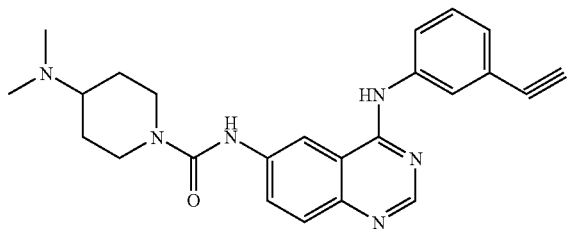
Compound 57
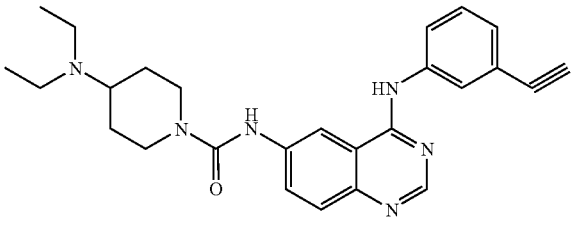
Compound 58
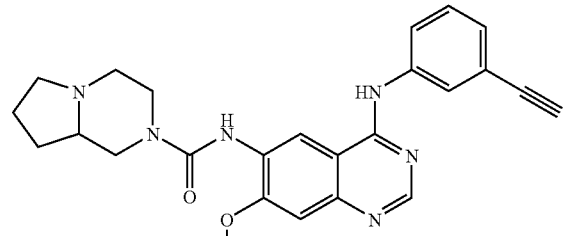
Compound 59
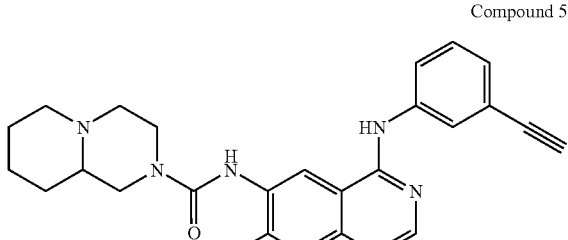
Compound 60
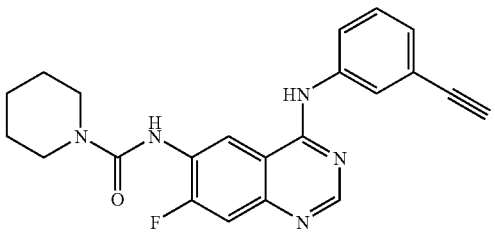
Compound 61
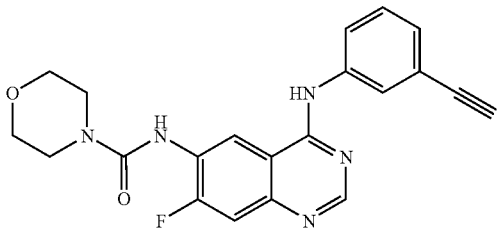
Compound 62
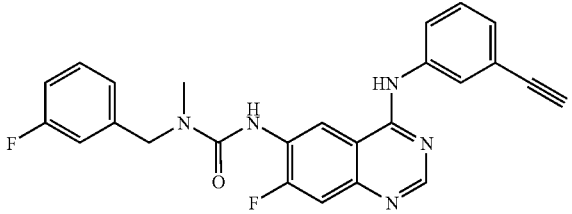
Compound 63
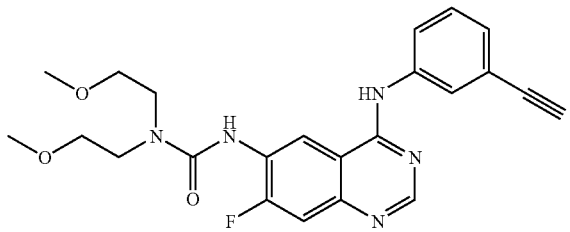
Compound 64
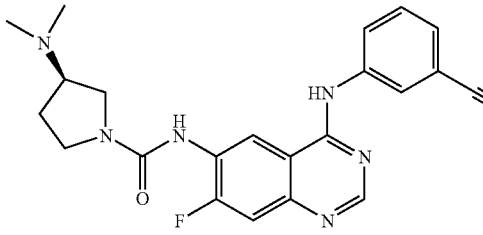
Compound 65
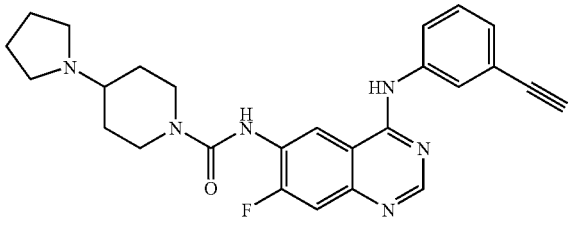

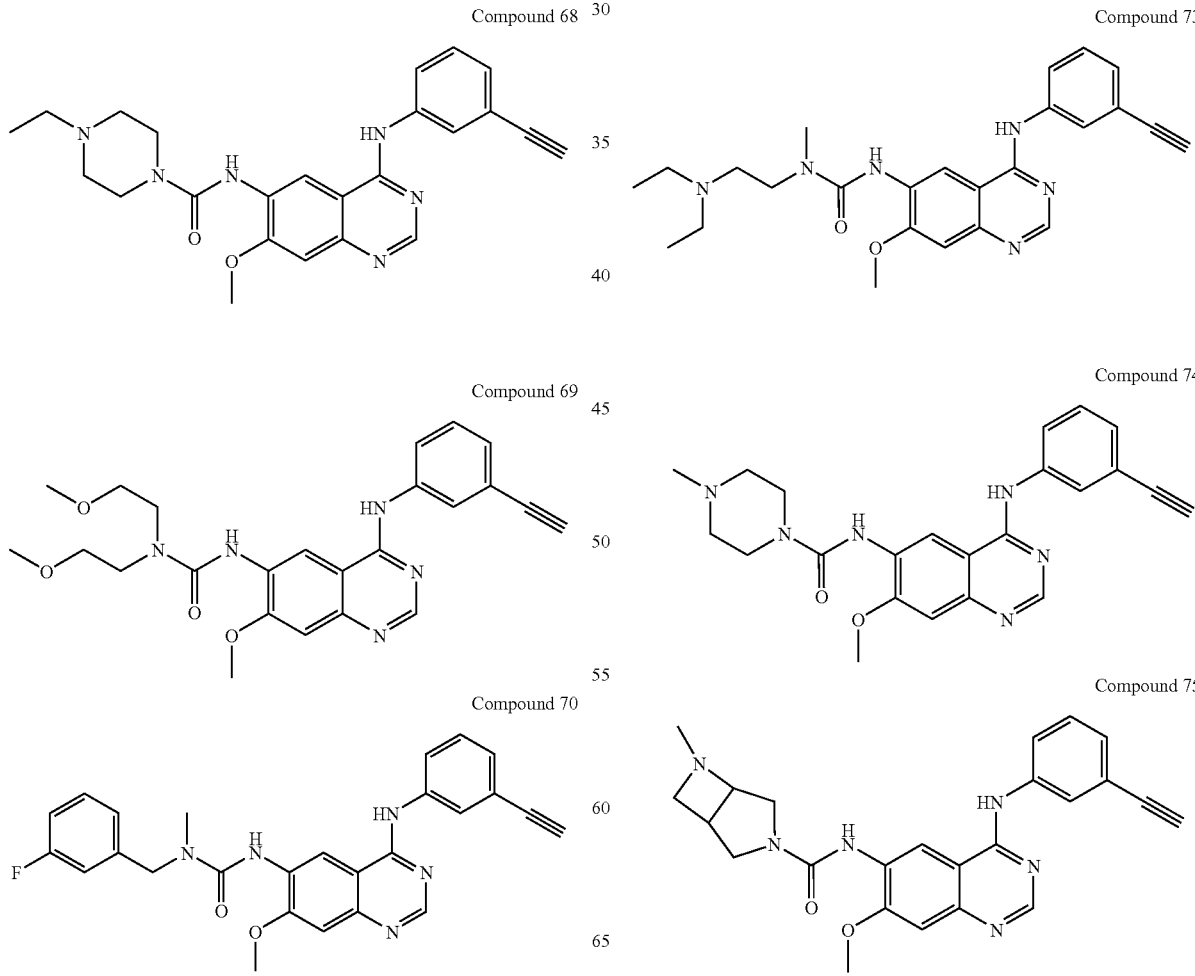

Compound 76
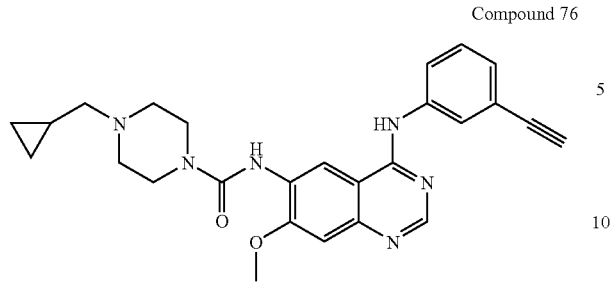
Compound 77
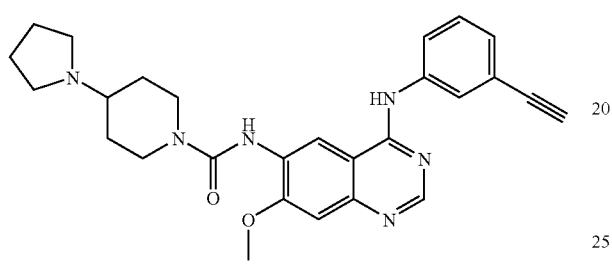
Compound 78
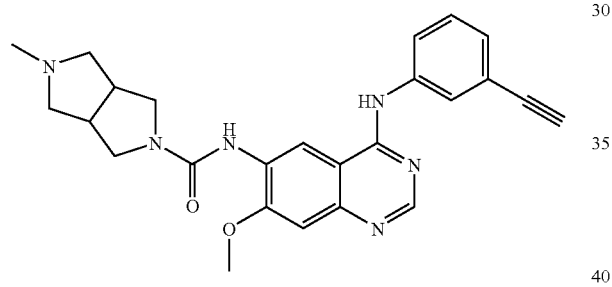
Compound 79
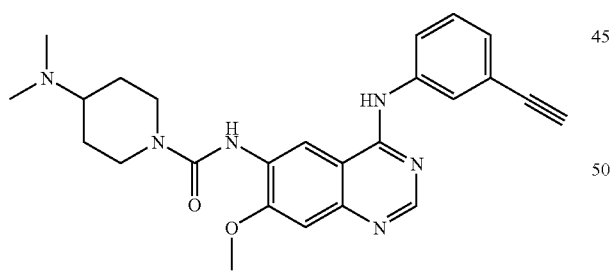
Compound 80
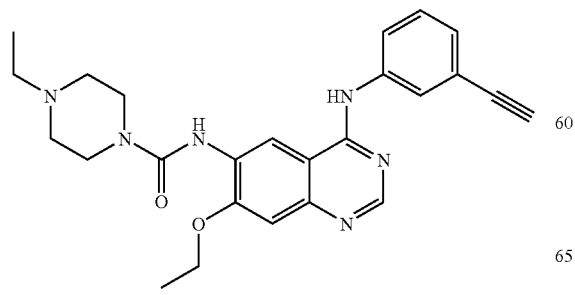
Compound 81
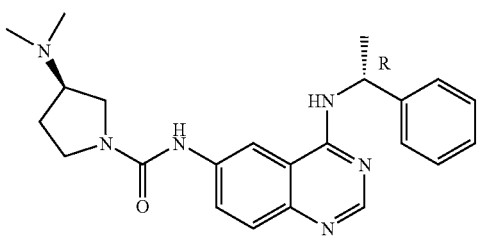
Compound 82
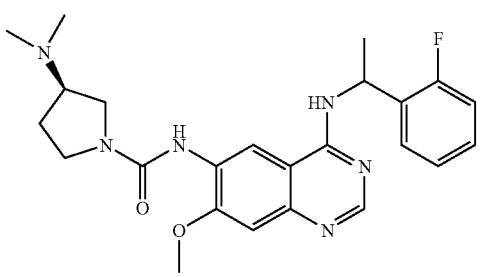
Compound 83
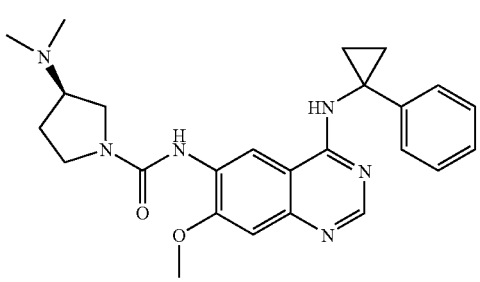
Compound 84
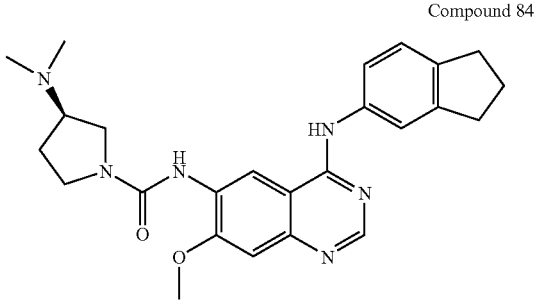
Compound 85
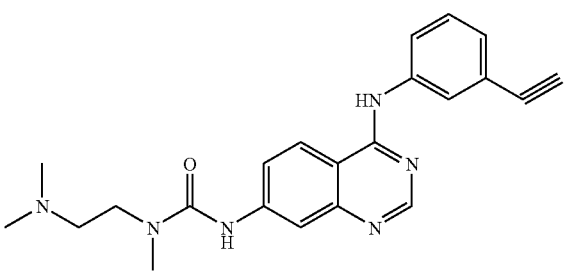

Compound 86
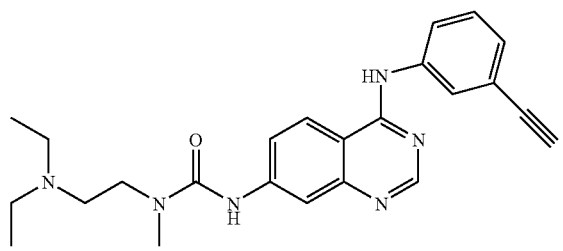
Compound 87
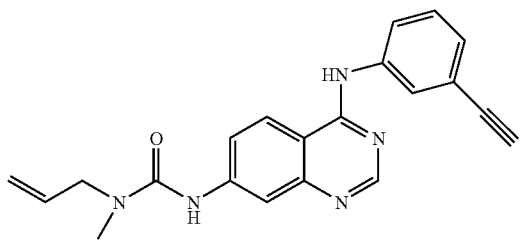
Compound 88
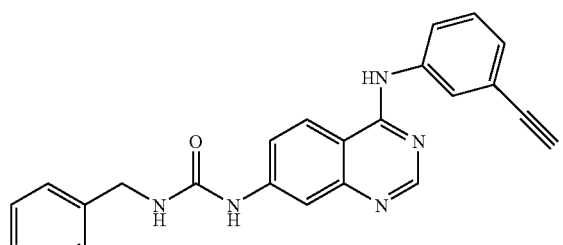
Compound 89
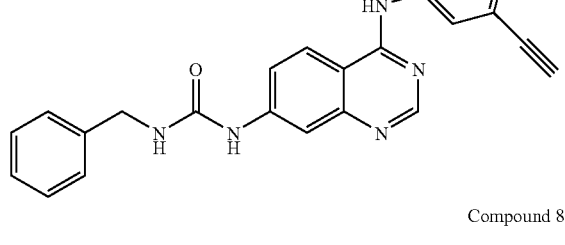
Compound 90
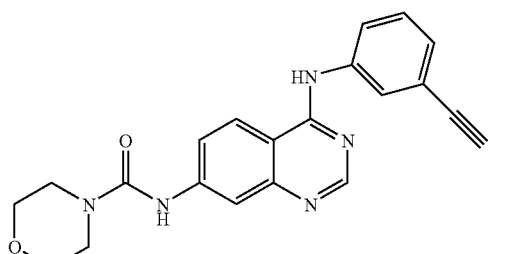
Compound 91
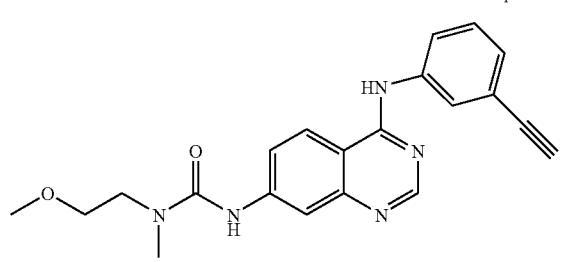
Compound 92
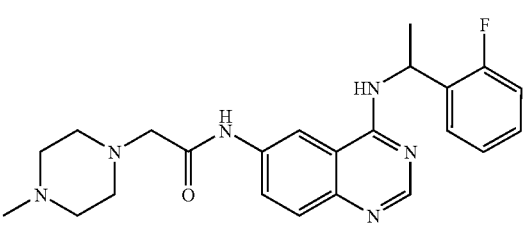
Compound 93
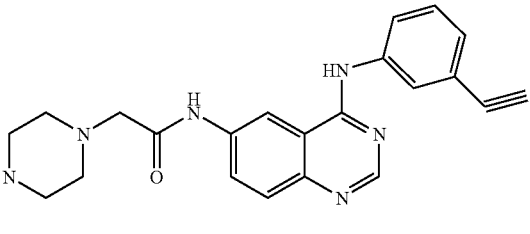
Compound 94
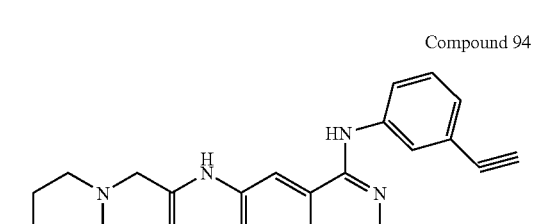
Compound 95
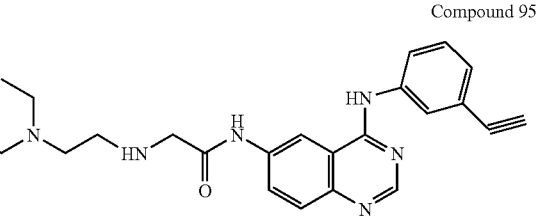
Compound 96
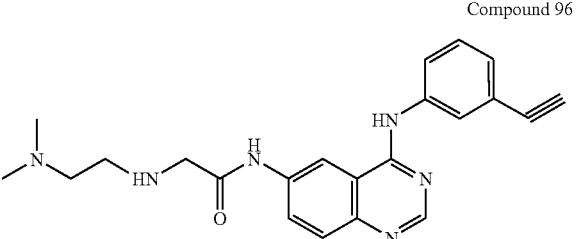
Compound 97
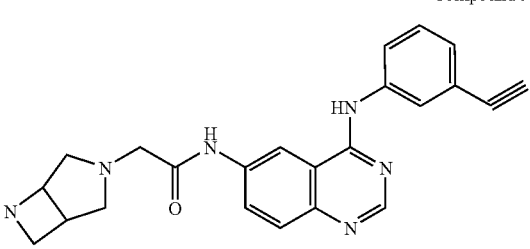

Compound 98
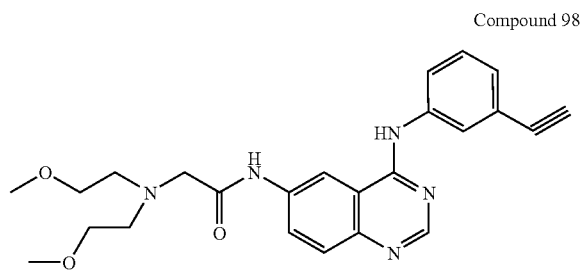
Compound 99
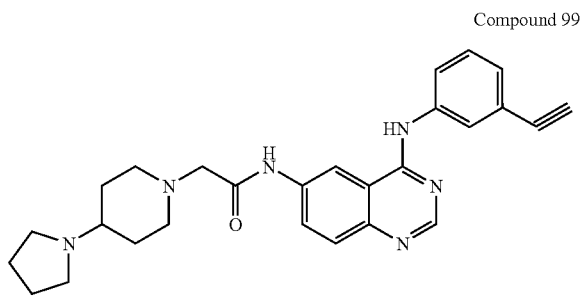
Compound 100
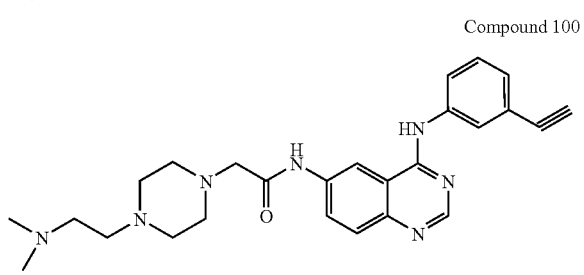
Compound 101
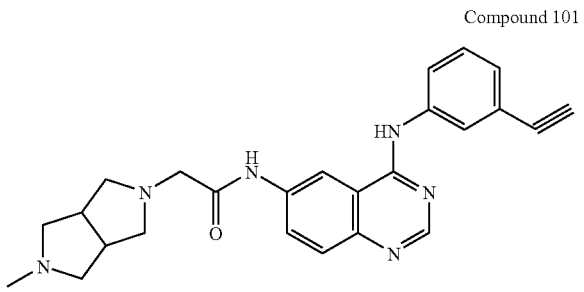
Compound 102
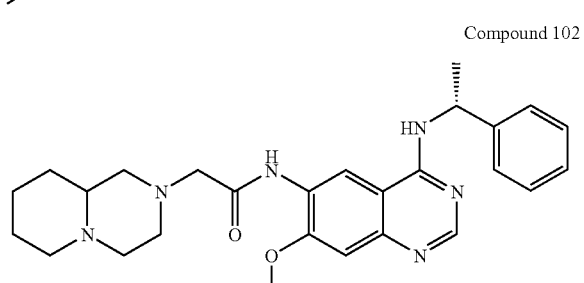
Compound 103
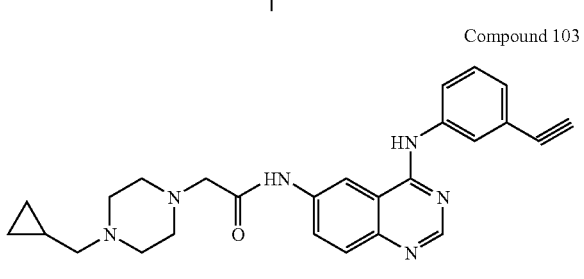
Compound 104
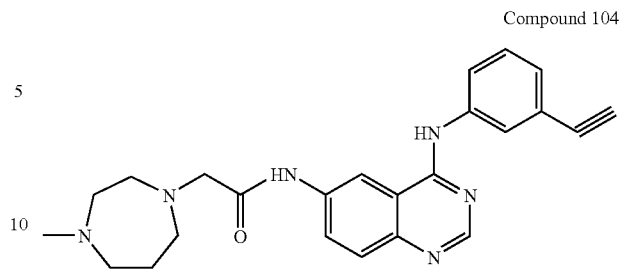
Compound 105
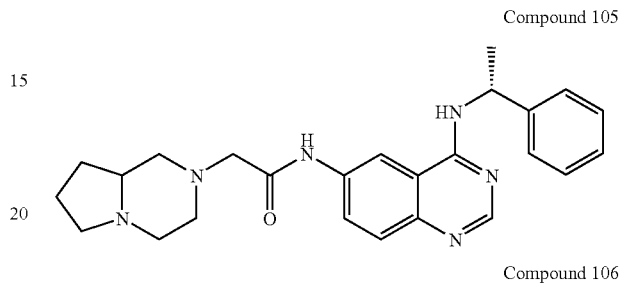
Compound 106
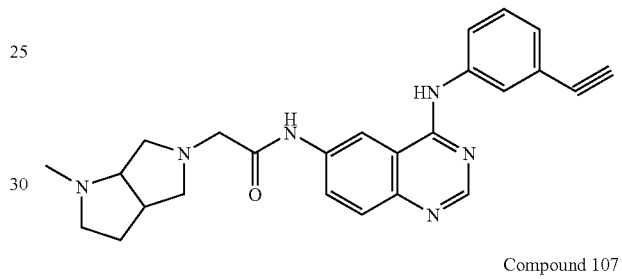
Compound 107
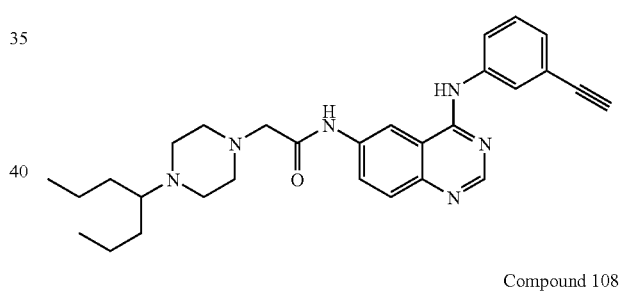
Compound 108
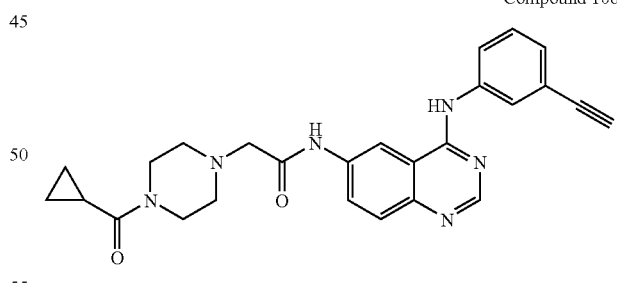
Compound 109
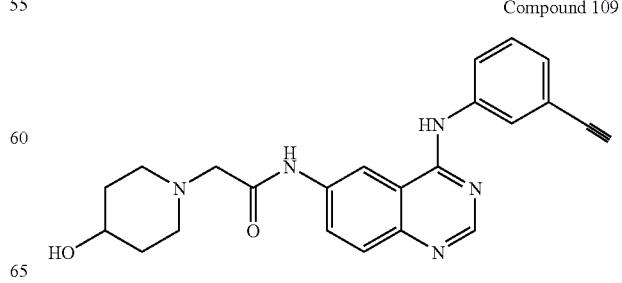

-continued
Compound 110
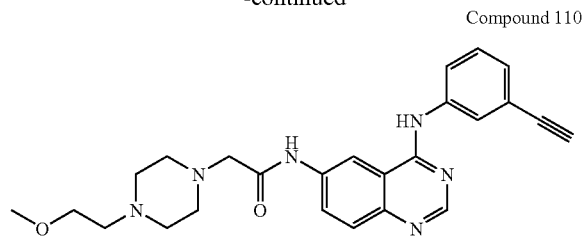
Compound 111
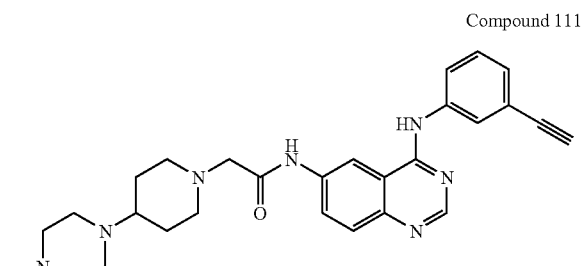
Compound 112
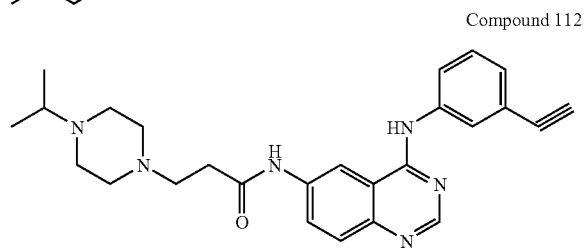
Compound 113
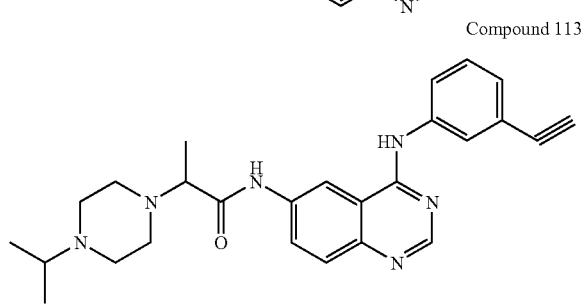
Compound 114
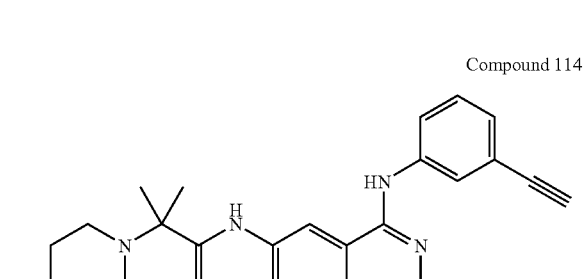
Compound 115
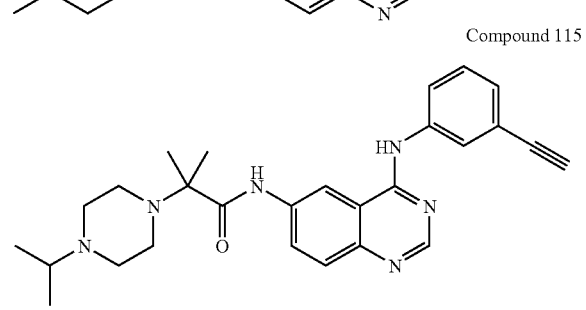
-continued
Compound 116
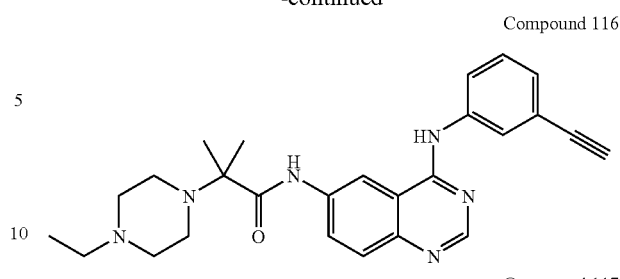
Compound 117
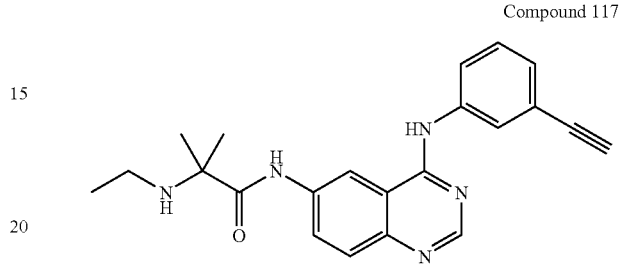
Compound 118
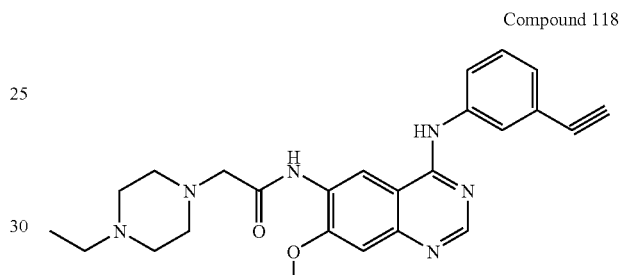
Compound 119
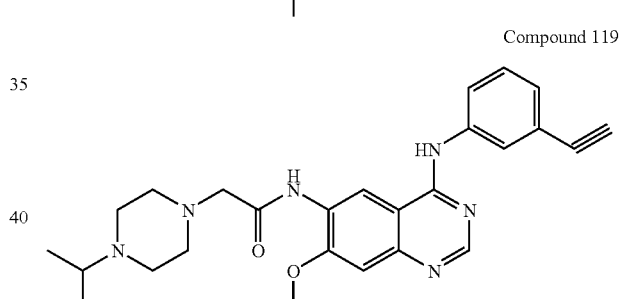
Compound 120
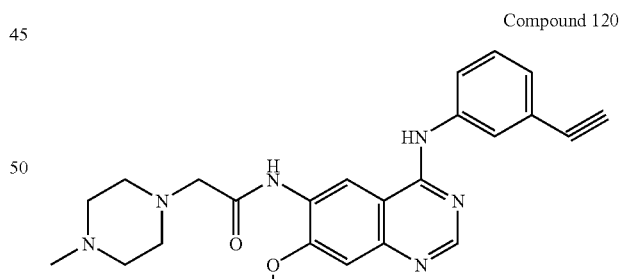
Compound 121
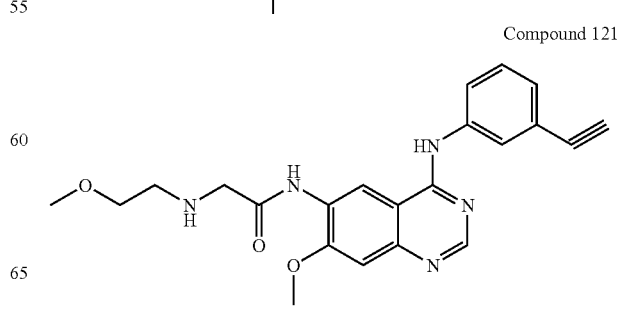

Compound 122
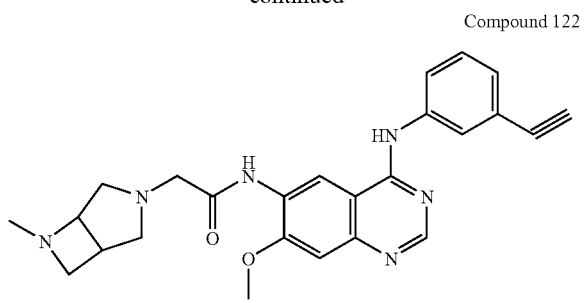
Compound 123
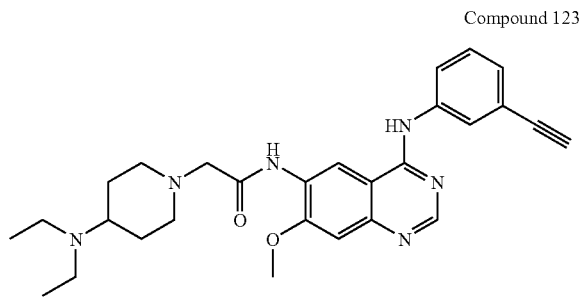
Compound 124
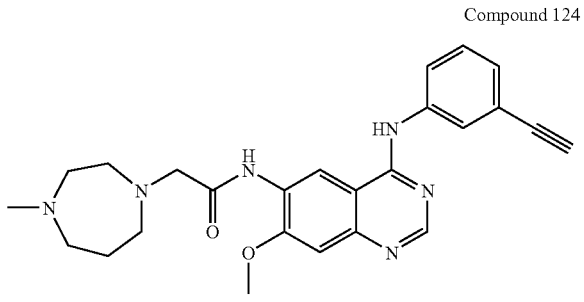
Compound 125
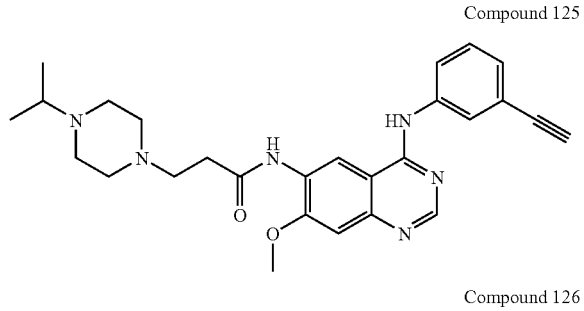
Compound 126
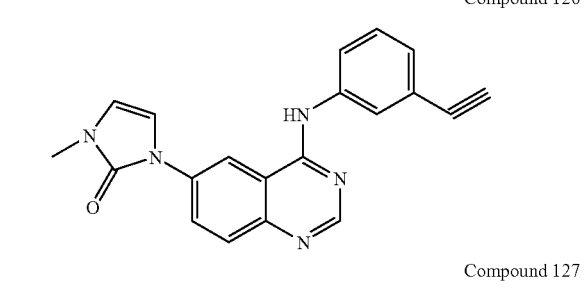
Compound 127
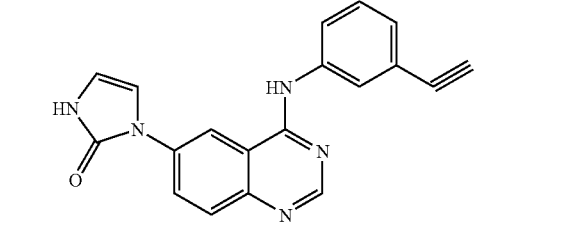
Compound 128
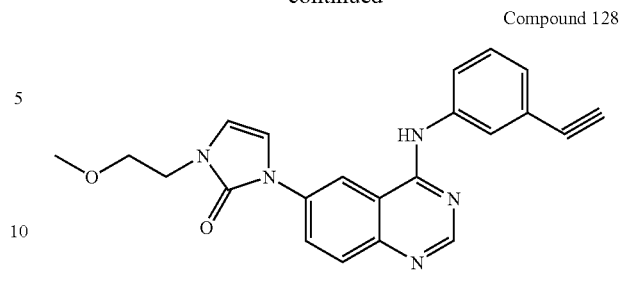
Compound 129
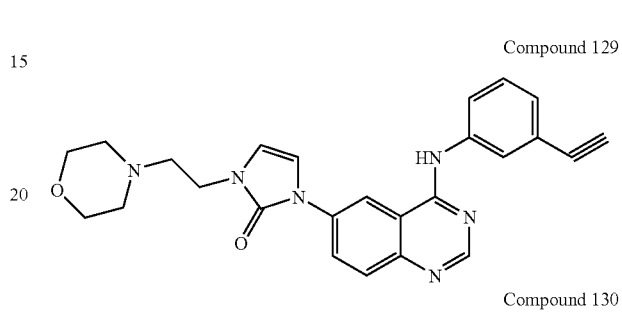
Compound 130
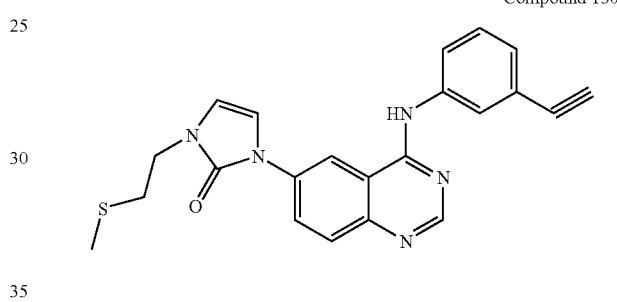
Compound 131
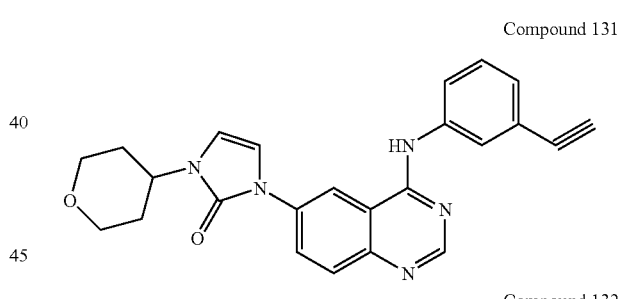
Compound 132
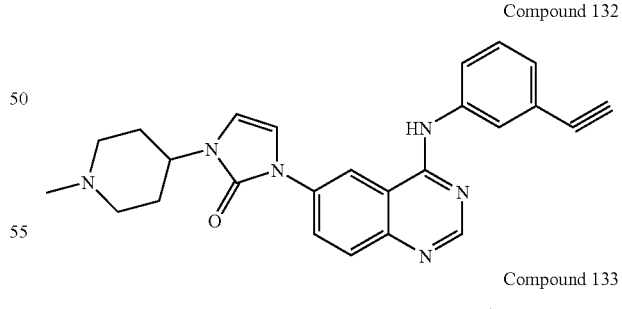
Compound 133
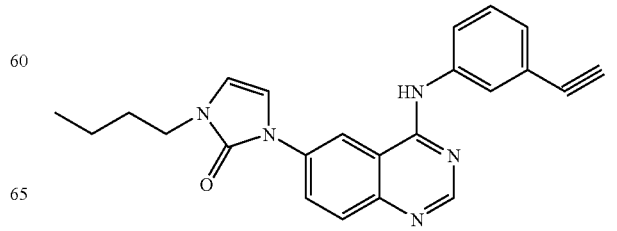

Compound 134
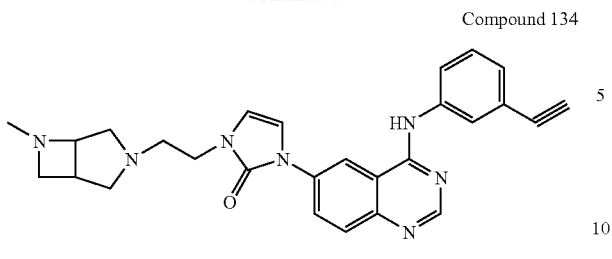
Compound 140
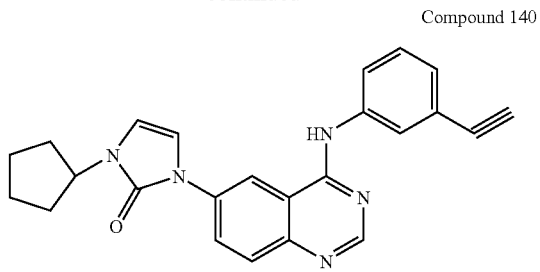
Compound 135
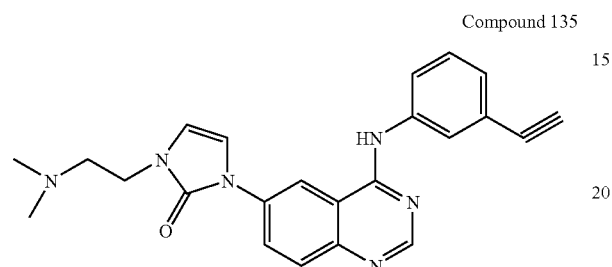
Compound 141
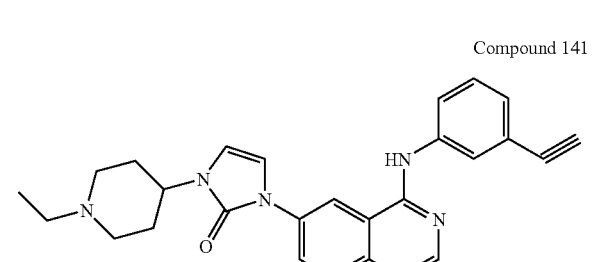
Compound 136
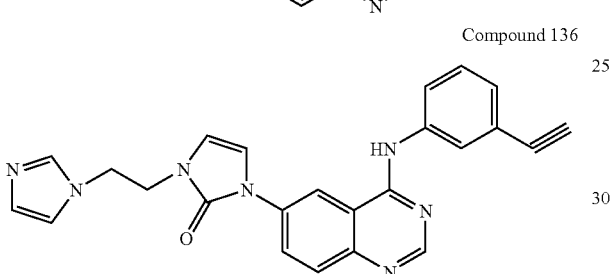
Compound 142
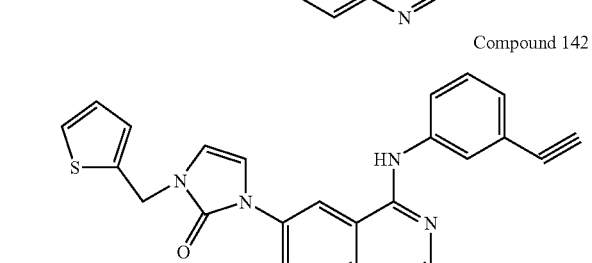
Compound 137
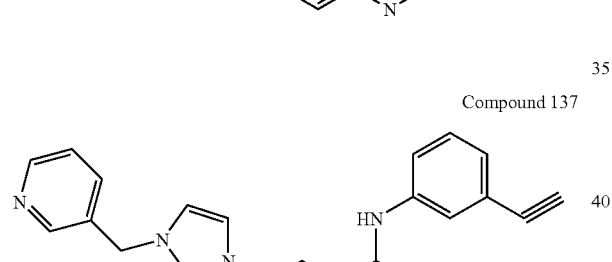
Compound 143
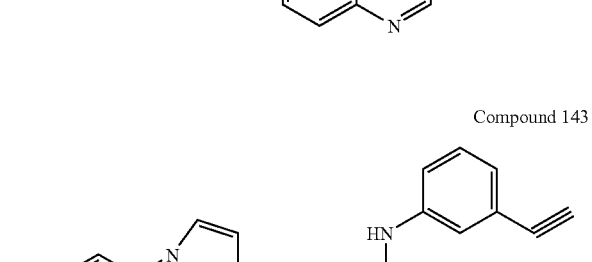
Compound 138
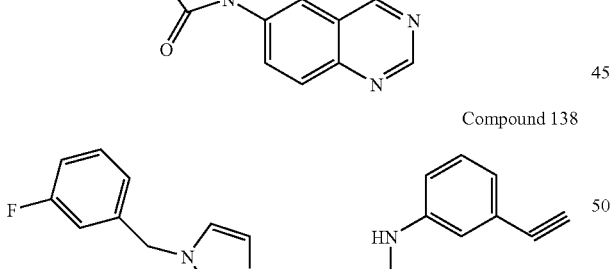
Compound 144
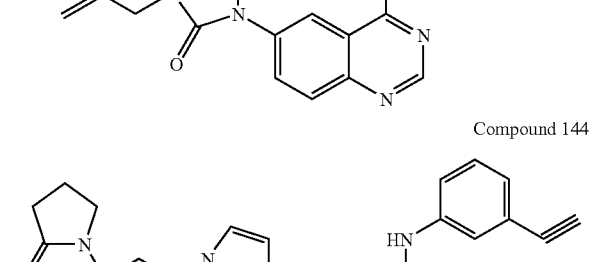
Compound 139
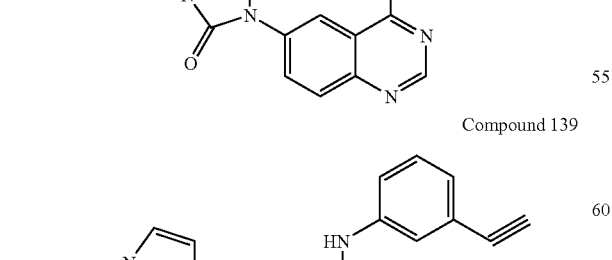
Compound 145
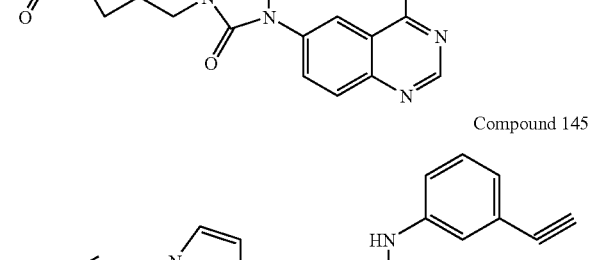

Compound 146
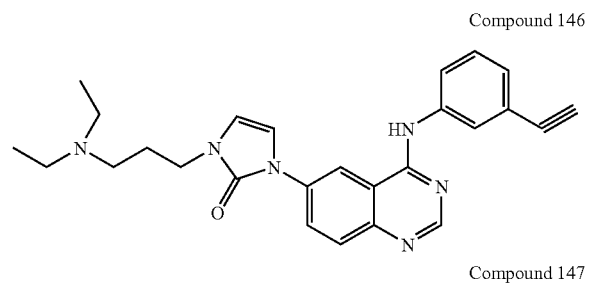
Compound 152
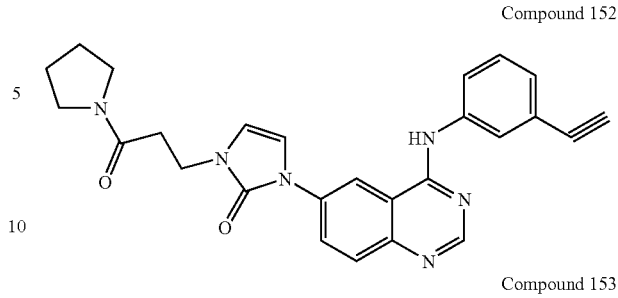
Compound 147
Compound 153
Compound 148
Compound 154
Compound 149
Compound 155
Compound 150
Compound 156
Compound 151
Compound 157

Compound 158
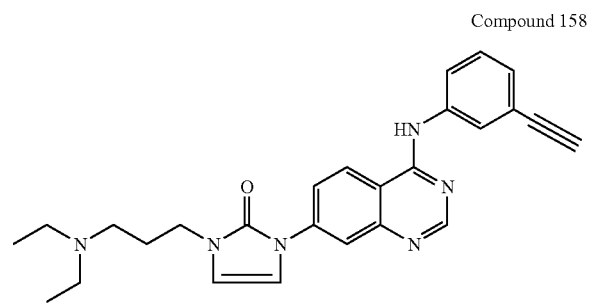
Compound 159
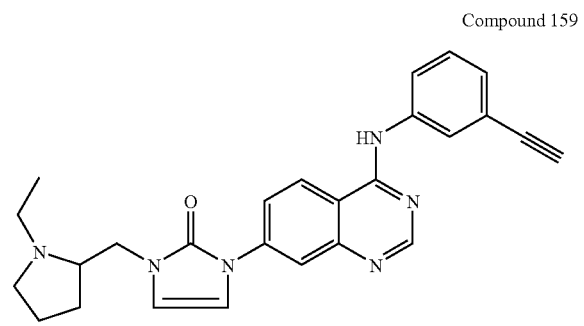
Compound 160
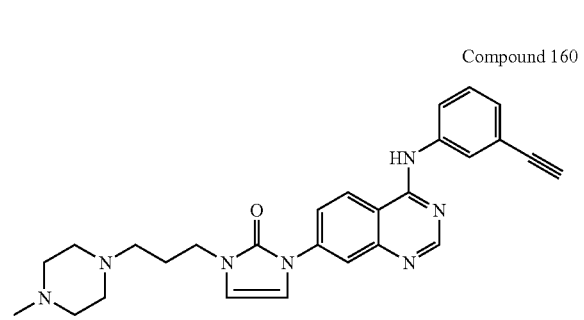
Compound 161
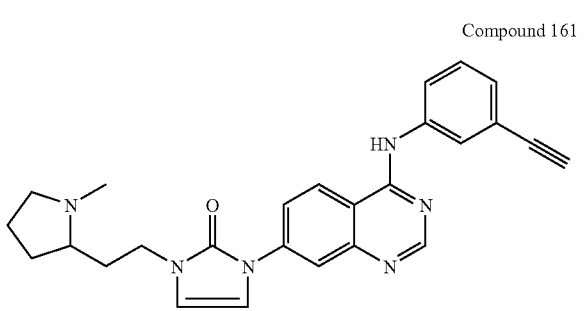
Compound 162
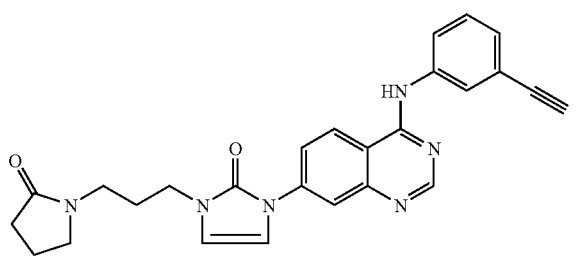
Compound 163
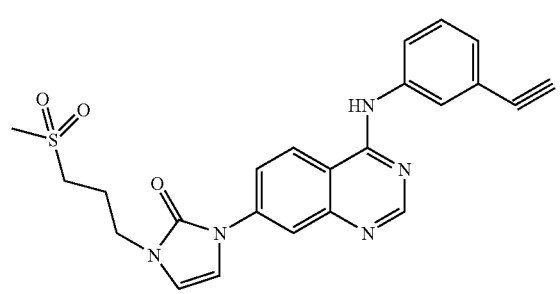
Compound 164
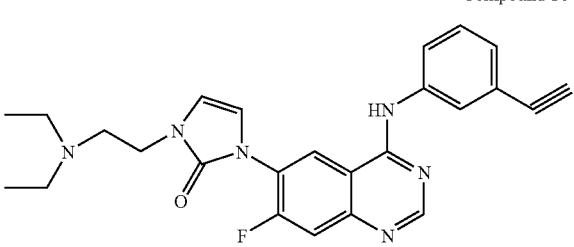
Compound 165
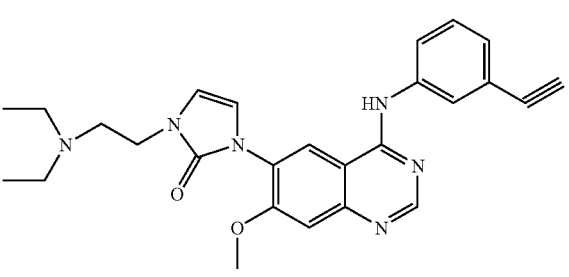
Compound 166
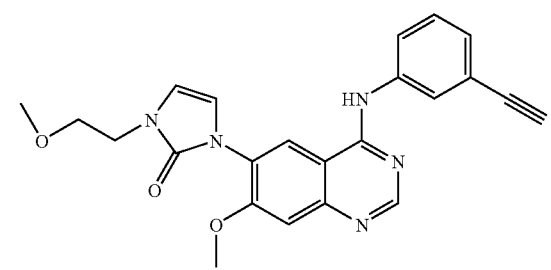
Compound 167
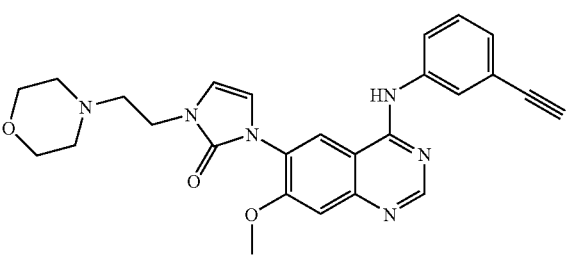

-continued

Compound 168

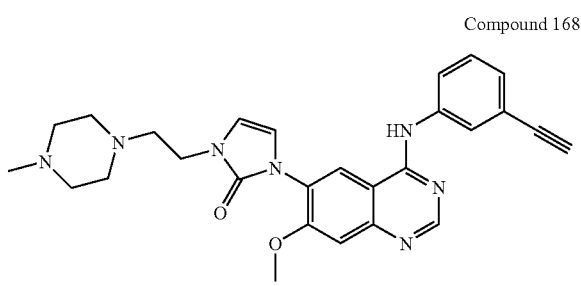

Compound 169

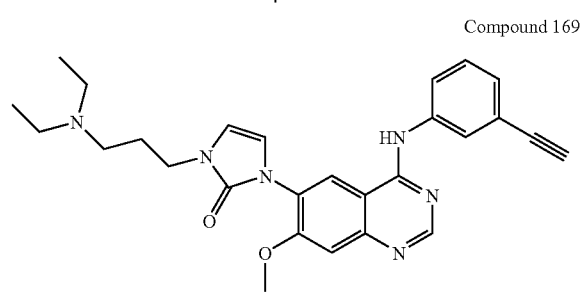

Compund 170

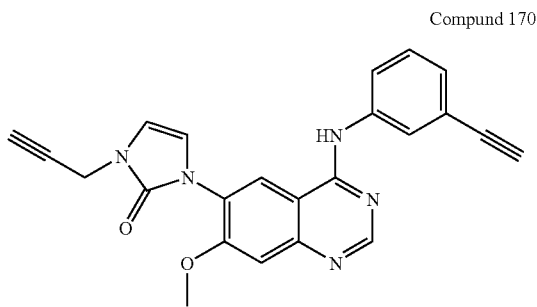

Another aspect of this invention relates to a method of treating cancer. The method includes administering to a subject having cancer an effective amount of one or more of the quinazoline compounds of this invention. Examples of the cancer to be treated include, but are not limited to, lung cancer, head and neck cancer, colorectal cancer, pancreatic cancer, colon cancer, breast cancer, ovarian cancer, prostate cancer, stomach cancer, kidney cancer, liver cancer, brain cancer, bone cancer, and leukemia.

Also within the scope of this invention are (1) a composition containing one or more of the quinazoline compounds described above and a pharmaceutically acceptable carrier for use in treating cancer, and (2) use of one or more of the quinazoline compounds for the manufacture of a medicament for treating cancer.

The details of one or more embodiments of the invention are set forth in the description below. Other features, objects and advantages of the invention will be apparent from the description and from the claims.

DETAILED DESCRIPTION

The quinazoline compounds of this invention can be synthesized from commercially available starting materials by methods well known in the art. For example, as shown in the scheme below, one can couple a suitable 4-chloro-quinazoline derivative with a benzene compound to obtain a compound of this invention.

Z is N or C—CN
X is O, S, NH or NCH$_3$

The compound thus obtained can be further modified at their peripheral positions to provide other compounds of this invention.

Synthetic chemistry transformations useful in synthesizing desirable quinazoline compounds are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the compounds can be purified by column chromatography, high performance liquid chromatography, crystallization, or other suitable methods.

The quinazoline compounds of this invention, when contacting with EGFR, inhibit this receptor's activity. An effective amount of one or more of these compounds can be therefore used to treat cancers that are associated with over-expression and over-activity of EGFR.

The term "an effective amount" refers to the amount of a quinazoline compound that is required to confer the intended effect in the subject. Effective amounts may vary, as recognized by those skilled in the art, depending on route of administration, excipient usage, and the possibility of co-usage with other agents. The term "treating" refers to administering one or more of the above-described quinazoline compounds to a subject that has cancer, or has a symptom of cancer, or has a predisposition toward cancer, with the purpose to cure, heal, alleviate, relieve, alter, remedy, ameliorate, improve, or affect cancer, the symptoms of cancer, or the predisposition toward cancer.

To practice this method, a composition having one or more of the quinazoline compounds of this invention can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond and about 70% by weight white soft paraffin.

A carrier in a pharmaceutical composition must be "acceptable" in the sense that it is compatible with active ingredients of the formulation (and preferably, capable of stabilizing it) and not deleterious to the subject to be treated. For example, solubilizing agents, such as cyclodextrins (which form specific, more soluble complexes with one or more of active quinazoline compounds of the extract), can be utilized as pharmaceutical excipients for delivery of the active ingredients. Examples of other carriers include colloidal silicon dioxide, magnesium stearate, cellulose, sodium lauryl sulfate, and D&C Yellow #10.

Suitable in vitro assays can be used to preliminarily evaluate the efficacy of the above-described quinazoline compounds in inhibiting the activity of EGFR. The compounds can further be examined for its efficacy in treating cancers by in vivo assays. For example, the compounds can be administered to an animal (e.g., a mouse model) having cancer and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever.

Example 1

Synthesis of 1-(3-fluorobenzyl)-3-(4-(3-ethynylphenylamino)quinazolin-6-yl)-1-methylurea (Compound 1)

The synthetic route to Compound 1 is shown below:

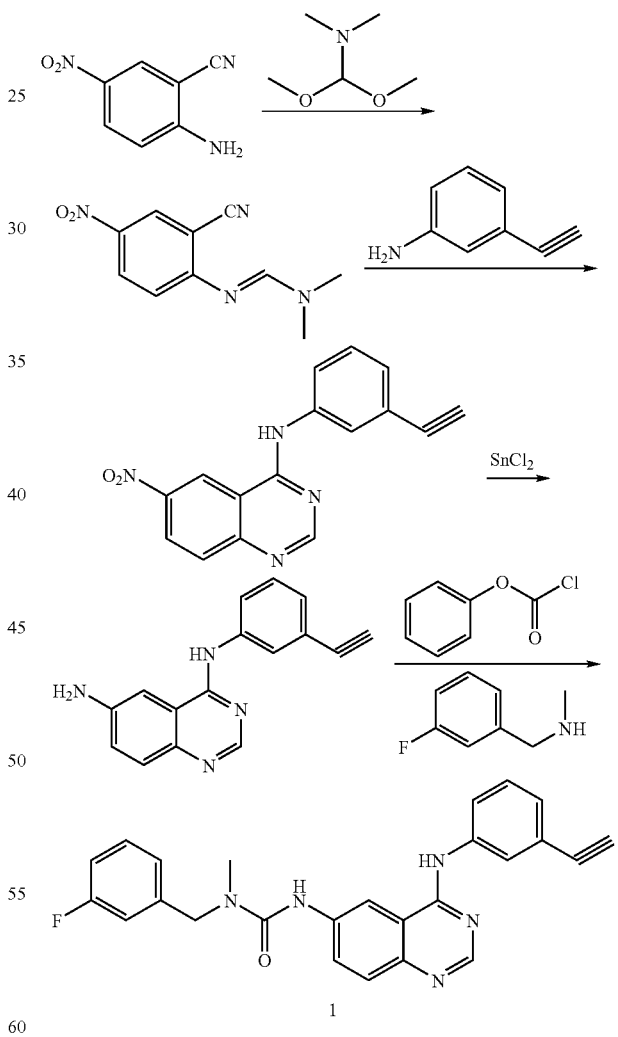

To a solution of 5-nitroanthranilonitrile (1.00 g, 6.13 mmol) in dioxane (25 mL) was added dimethylformamide dimethylacetal (0.88 g, 7.36 mmol). After stirred at 100° C. for 2 h, the reaction mixture was cooled to room temperature and refrigerated. The precipitate was filtered out, washed with cold ether several times, and dried in vacuo to give 1.30 g (97%) of product (E)-N'-(2-cyano-4-nitrophenyl)-N,N-dimethylformamidine as a yellow solid.

A mixture of (E)-N'-(2-cyano-4-nitrophenyl)-N,N-dimethylformamidine (1.00 g, 4.58 mmol) and 3-aminophenylacetylene (0.64 g, 5.49 mmol) in HOAc (15 mL) was stirred at 100° C. for 3 h. The resulting mixture was cooled to room temperature. The precipitate was filtered out, washed with ether, and dried in vacuo to give 1.23 g (93%) of N-(3-ethynylphenyl)-6-nitroquinazolin-4-amine as a yellow solid.

A mixture of N-(3-ethynylphenyl)-6-nitroquinazolin-4-amine (1.00 g, 3.45 mmol) and $SnCl_2 \cdot 2H_2O$ (3.10 g, 13.8 mmol) in ethyl acetate (35 mL) was refluxed for 2 h and then cooled to room temperature. After its pH was adjusted to 9-10 with 5% aqueous $NaHCO_3$, the mixture was subject to extraction with EtOAc. The combined organic layers were washed with saturated brine and $H_2O$ and dried. The solvent was removed under reduced pressure to provide 0.79 g (89%) of N4-(3-ethynylphenyl)quinazoline-4,6-diamine as a yellow solid.

To a solution of N4-(3-ethynylphenyl)quinazoline-4,6-diamine (100 mg, 0.38 mmol) in DMF (2 mL) containing pyridine (37 μL, 0.46 mmol) was added phenyl chloroformate (49 μL, 0.38 mmol) in dropwise at room temperature. After 10 min, (3-fluorobenzyl)methylamine (52.9 mg, 0.38 mmol) was added and the reaction mixture was heated to 80° C. for 1 h. After cooled to r.t, the reaction mixture was diluted with ethyl acetate and washed with water. The combined organic layers were concentrated and purified with a silica column to give Compound 1 as a yellow solid in 86% yield.

$^1$H NMR (DMSO-$d_6$, 400 MHz): δ 9.83 (s, 1H), 8.89 (s, 1H), 8.55 (d, J=8 Hz, 2H), 8.04 (s, 1H), 7.79 (dd, J=2.4 Hz, 2.0 Hz, 1H), 7.79 (dd, J=2.0 Hz, 2.4 Hz, 1H), 7.74 (d, J=2.0 Hz 1H), 7.41~7.37 (m, 3H), 7.13~7.10 (m, 3H), 4.64 (s, 2H), 4.20 (s, 1H), 3.03 (s, 3H); MS (m/e): 426 (M+1).

Examples 2-59

Synthesis of Compounds 2-59

Compounds 2-59 were prepared in a manner similar to that described in Example 1.

Compound 2:
$^1$H NMR (DMSO-$d_6$, 400 MHz): δ 9.83 (s, 1H), 8.88 (s, 1H), 8.79 (s, 1H) 8.43 (d, J=8 Hz, 2H), 8.10 (s, 1H), 7.94 (t, J=2.4 Hz, 1H), 7.82 (t, J=2.0 Hz, 1H), 7.80 (d, J=2.0 Hz, 1H), 7.42~7.36 (m, 3H), 7.09~7.06 (m, 3H), 4.48 (s, 2H), 3.53 (s, 1H); MS (m/e): 412 (M+1).

Compound 3:
$^1$H NMR (DMSO-$d_6$, 400 MHz): δ 9.42 (s, 1H), 8.93 (s, 1H), 8.63 (s, 1H), 8.53 (s, 1H), 8.44 (d, J=3.2 Hz, 2H), 8.21 (s, 1H), 7.35 (t, J=2.4 Hz, 1H), 7.32~6.88 (m, 5H), 6.80 (d, J=2.0 Hz 1H), 6.68 (d, J=2.4 Hz, 1H), 6.65 (s, 1H), 4.44 (s, 2H), 4.04 (s, 1H); MS (m/e): 395 (M+1).

Compound 4:
$^1$H NMR (DMSO-$d_6$, 400 MHz): 9.68 (s, 1H), 9.14 (s, 1H), 8.51 (s, 1H), 8.51 (d, J=2.0 Hz, 1H), 8.11 (s, 1H), 7.89 (t, J=2.0 Hz, 2H), 7.72 (d, J=8 Hz, 1H), 7.40 (t, J=3.6 Hz, 1H), 7.21 (d, J=4 Hz, 1H), 4.24 (s, 1H), 3.46 (s, 4H), 1.53 (s, 6H): MS (m/e): 372 (M+1).

Compound 5:
$^1$H NMR (DMSO-$d_6$, 400 MHz): δ 9.83 (s, 1H), 8.88 (s, 1H), 8.79 (s, 1H) 8.43 (d, J=8 Hz, 2H), 8.10 (s, 1H), 7.94 (t, J=2.4 Hz, 1H), 7.82 (t, J=2.0 Hz, 1H), 7.80 (t, J=2.0 Hz, 1H), 7.42~7.36 (m, 3H), 7.09~7.06 (m, 3H), 4.48 (s, 2H), 3.53 (s, 1H); MS (m/e): 412 (M+1).

Compound 6:
$^1$H NMR (DMSO-$d_6$, 400 MHz): δ 9.83 (s, 1H), 8.87 (d, 1H), 8.79 (s, 1H) 8.43 (d, J=8 Hz, 2H), 8.10 (s, 1H), 7.94 (t, J=2.4 Hz, 1H), 7.80 (d, J=2.0 Hz, 1H), 7.42~7.36 (m, 3H), 7.09~7.06 (m, 3H), 4.48 (s, 2H), 3.53 (s, 1H); MS (m/e): 430 (M+1).

Compound 7:
$^1$H NMR (DMSO-$d_6$, 400 MHz): δ 9.77 (s, 1H), 8.57 (d, J=10.8 Hz, 1H), 8.50 (s, 1H), 8.04 (s, 1H), 7.96 (d, J=2 Hz, 1H), 7.89 (d, J=8 Hz, 1H), 7.69 (d, J=20 Hz, 1H), 7.35 (t, J=8.0 Hz, 1H), 4.20 (s, 1H), 2.49 (s, 4H), 1.86 (s, 4H); MS (m/e): 358 (M+1).

Compound 8:
$^1$H NMR (DMSO-$d_6$, 400 MHz): δ 9.77 (s, 1H), 9.02 (s, 1H), 8.53 (s, 1H), 8.51 (d, J=2 Hz, 1H), 8.05 (s, 1H), 7.88 (t, J=8 Hz, 2H), 7.72 (d, J=8 Hz, 1H), 7.38 (d, J=8 Hz, 1H), 7.20 (d, J=7.2 Hz, 1H), 4.18 (s, 1H), 3.65 (t, J=4.4 Hz, 4H), 3.51 (t, J=4.8 Hz, 4H); MS (m/e): 374 (M+1).

Compound 9:
$^1$H NMR (DMSO-$d_6$, 400 MHz): δ 9.77 (s, 1H), 8.99 (s, 1H), 8.52 (s, 2H), 8.05 (s, 1H), 7.93 (m, 2H), 7.69 (d, J=8.8 Hz, 1H), 7.38 (t, J=8 Hz, 1H), 7.19 (d, J=8 Hz, 1H), 4.23 (s, 1H), 2.23-0.91 (m, 8H), 0.91 (m, J=2.8 Hz, 6H); MS (m/e): 400 (M+1).

Compound 10:
$^1$H NMR (DMSO-$d_6$, 400 MHz): δ 9.83 (s, 1H), 8.75 (s, 1H), 8.52 (s, 1H), 8.44 (s, 1H), 7.90 (m, 2H), 7.71 (d, J=8.4 Hz, 2H), 7.39 (t, J=8 Hz, 1H), 7.20 (d, J=8 Hz, 1H), 4.20 (s, 1H), 3.59 (s, 4H), 3.53 (s, 4H), 3.53 (s, 6H); MS (m/e): 420 (M+1).

Compound 11:
$^1$H NMR (CD$_3$OD, 400 MHz): δ 8.5 (s 1H), 8.06 (s 1H), 8.05 (s, 1H), 7.68-7.80 (d, J=9.2 Hz, 3H), 7.39-7.42 (t, J=8.0 Hz 1H), 7.29-7.31 (d, J=3.2 Hz, 1H), 7.20-7.20 (d, J=0.4 Hz, 1H), 4.08-4.12 (t, J=8.0 Hz, 2H), 3.67-3.73 (m, 4H), 3.21-3.25 (m, 6H), 1.65-1.85 (m, 6H); MS (m/e): 459.3 (M+1).

Compound 13:
$^1$H NMR (DMSO-$d_6$, 400 MHz): δ 9.81 (s, 1H), 8.63 (s, 1H), 8.54 (s, 1H), 8.49 (s, 1H), 8.51 (s, 1H), 8.05 (s, 1H), 7.92 (m, 2H), 7.70 (d, J=12 Hz, 1H), 7.37 (t, J=2.4 Hz, 1H), 7.19 (d, J=4 Hz, 1H), 4.17 (s, 1H), 3.71 (m, 2H), 3.76 (m, 2H), 3.16 (m, 1H), 2.70 (m, 1H), 2.18-2.07 (m, 8H), 1.73 (m, 1H), 1.31 (m, 1H); MS (m/e): 441 (M+1).

Compound 14:
$^1$H NMR (DMSO-$d_6$, 400 MHz): δ 9.76 (s, 1H), 8.97 (s, 1H), 8.51 (d, J=8.8 Hz, 2H), 8.05 (s, 1H), 7.89 (t, J=8.8 Hz, 2H), 7.71 (d, J=8.8 Hz, 1H), 7.38 (t, J=8.0 Hz, 1H), 7.20 (d, J=8 Hz, 1H), 4.19 (s, 1H), 3.54 (s, 4H), 2.26 (t, J=2 Hz, 2H), 0.87 (d, J=4 Hz, 1H), 0.49 (d, J=8 Hz, 2H), 0.11 (s, 2H); MS (m/e): 427 (M+1).

Compound 15:
$^1$H NMR (DMSO-$d_6$, 400 MHz): δ 9.95 (s, 1H), 8.87 (s, 1H), 8.51 (s, 1H), 8.47 (s, 1H), 8.03 (s, 1H), 7.85 (m, 2H), 7.69 (d, J=8.8 Hz, 1H), 7.37 (t, J=8.0 Hz, 1H), 7.19 (d, J=8 Hz, 1H), 4.41 (s, 1H), 4.08 (s, 1H), 4.05 (s, 1H), 2.94 (t, J=10.8 Hz, 2H), 2.17 (t, J=4 Hz, 1H), 1.86 (t, J=6 Hz, 2H), 1.66 (s, 4H), 1.33 (m, 2H); MS (m/e): 401 (M+1).

Compound 17:
$^1$H NMR (DMSO-$d_6$, 400 MHz): δ 9.96 (s, 1H), 9.44 (s, 1H), 8.50 (s, 1H), 8.45 (s, 1H), 8.00 (s, 1H), 7.88 (t, J=2.8 Hz, 1H), 7.70 (d, J=8.8 Hz, 1H), 7.36 (t, J=8.0 Hz, 1H), 7.19 (d, J=7.6 Hz, 1H), 6.85 (d, J=6 Hz, 1H), 4.19 (s, 1H), 3.33 (m, 4H), 3.22 (s, 3H); MS (m/e): 362 (M+1).

Compound 18:
$^1$H NMR (CD$_3$OD, 400 MHz): δ 8.51 (s, 1H), 8.47~8.46 (d, J=2.4 Hz, 1H), 7.97 (s, 1H), 7.93~7.91 (dd, J=2.4 Hz, 8.8 Hz, 1H), 7.83~7.81 (dd, J=1.6 Hz, 8.4 Hz, 1H), 7.77~7.74 (d, J=8.8 Hz, 1H), 7.40~7.36 (t, J=8.0 Hz, 1H), 7.28~7.26 (dd, J=1.2 Hz, 8 Hz, 1H), 3.78~7.74 (t, J=6.4 Hz, 2H), 3.52 (s, 1H), 2.93~2.90 (m, 1H), 2.86~2.82 (t, J=6.0 Hz, 2H), 1.13~1.10 (m, 2H), 0.97~0.95 (m, 2H); MS (m/e): 397.4 (M+1)

Compound 19:

$^1$H NMR (DMSO-$d_6$, 400 MHz): δ 9.77 (s, 1H), 8.90 (s, 1H), 8.55~8.55 (d, J=2 Hz, 1H), 8.44 (s, 1H), 8.18~8.17 (d, J=1.2 Hz, 1H), 8.07 (s, 1H), 7.94~7.91 (dd, J=2 Hz, 9.2 Hz, 1H), 7.70~7.65 (m, 2H), 7.56~7.54 (d, J=8.8 Hz, 1H), 7.43~7.40 (m, 1H), 7.17~7.09 (m, 3H), 4.64 (s, 2H), 3.03 (s, 3H); MS (m/e): 417.5 (M+1)

Compound 20:

$^1$H NMR (DMSO-$d_6$, 400 MHz): δ 9.78 (s, 1H), 8.71 (s, 1H), 8.54~8.53 (d, J=1.6 Hz, 1H), 8.52 (s, 1H), 8.06 (s, 1H), 7.96~7.90 (m, 2H). 7.71~7.69 (d, J=9.2 Hz, 1H), 7.40~7.36 (t, J=8 Hz, 1H), 7.20~7.19 (d, J=7.2 Hz, 1H), 4.20 (s, 1H), 3.43~3.41 (m, 2H), 2.99 (s, 3H), 1.13-1.09 (t, J=7.2 Hz, 3H); MS (m/e): 346.4 (M+1)

Compound 22:

$^1$H NMR (CD$_3$OD, 400 MHz): δ 8.49 (s, 1H), 8.40~8.39 (d, J=2.4 Hz, 1H), 7.99 (s, 1H), 7.94 (s, 1H), 7.80~7.77 (d, J=8.8 Hz, 1H), 7.74~7.72 (d, J=8.8 Hz, 1H), 7.62~7.57 (m, 1H), 7.39~7.35 (t, J=7.6 Hz, 1H), 7.28~7.26 (d, J=7.6 Hz, 1H), 3.55 (s, 1H), 3.56~3.49 (m, 4H), 2.85~2.78 (m, 6H), 1.28~1.25 (t, J=6.8 Hz, 3H), 1.19~1.15 (t, J=6.8 Hz, 6H); MS (m/e): 431.5 (M+1)

Compound 23:

$^1$H NMR (CD$_3$OD, 400 MHz): δ 8.51 (s, 1H), 8.39~8.39 (d, J=2.4 Hz, 1H), 7.98 (s, 1H), 7.83 (s, 1H), 7.81~7.78 (dd, J=2 Hz, 9.6 Hz, 1H), 7.75~7.73 (d, J=9.4 Hz, 1H), 7.41~7.37 (t, J=8 Hz, 1H), 7.30~7.27 (m, 1H), 3.53 (s, 1H), 3.46~3.43 (t, J=7.2 Hz, 4H), 1.68~1.65 (m, 4H), 1.45~1.40 (m, 4H), 1.03~0.99 (t, J=7.2 Hz, 6H); MS (m/e): 416.5 (M+1)

Compound 24:

$^1$H NMR (CD$_3$OD, 400 MHz): δ 8.50 (s, 1H), 8.40~8.39 (d, J=2.0 Hz, 1H), 7.97 (s, 1H), 7.83~7.81 (d, J=8.4 Hz, 1H), 7.75~7.68 (m, 2H), 7.41~7.37 (t, J=8.4 Hz, 1H), 7.29~7.27 (m, 1H), 3.61~3.58 (t, J=6.0 Hz, 2H), 3.53 (s, 1H), 3.12 (s, 1H), 2.72~2.69 (t, J=6.0 Hz, 2H), 2.45 (s, 6H); MS (m/e): 389.5 (M+1).

Compound 25:

$^1$H NMR (CD$_3$OD, 400 MHz): δ 8.51 (s, 1H), 8.40~8.39 (d, J=2 Hz, 1H), 7.98 (s, 1H), 7.83~7.80 (dd, J=2.4 Hz, 9.2 Hz, 1H), 7.75~7.73 (d, J=9.2 Hz, 1H), 7.41~7.27 (t, J=8 Hz, 1H), 7.29~7.27 (d, J=7.6 Hz, 1H), 3.53 (s, 1H), 3.53~3.48 (t, J=7.6 Hz, 2H), 3.39~3.36 (t, J=6.8 Hz, 2H), 1.77~1.71 (m, 2H), 1.15~1.14 (m, 1H), 1.02~0.98 (t, J=7.2 Hz, 3H), 0.62~0.58 (m, 2H), 0.37~0.34 (m, 2H); MS (m/e): 400.5 (M+1)

Compound 26:

$^1$H NMR (CD$_3$OD, 400 MHz): δ 8.75 (s, 1H), 8.73~8.72 (d, J=2 Hz, 1H), 8.08~8.05 (dd, J=2.4 Hz, 9.2 Hz, 1H), 7.92~7.92 (d, J=1.2 Hz, 1H), 7.83 (s, 1H), 7.81 (s, 1H), 7.78~7.75 (m, 1H), 7.50~7.47 (m, 2H), 3.80~3.77 (t, J=6.4 Hz, 2H), 3.63 (s, 3H), 3.24 (s, 3H), 2.86~2.83 (t, J=6.4 Hz, 2H); MS (m/e): 371.4 (M+1)

Compound 27:

$^1$H NMR (CD$_3$OD, 400 MHz): δ 8.50 (s, 1H), 8.40~8.39 (d, J=2.4 Hz, 1H), 7.79 (s, 1H), 7.82~7.79 (dd, J=2.0 Hz, 8.8 Hz, 2H), 7.73~7.71 (d, J=8.8 Hz, 1H), 7.40~7.36 (t, J=8.0 Hz, 1H), 7.28~7.26 (d, J=8.4 Hz, 1H), 3.53 (s, 1H), 3.51~3.4 (q, J=7.2 Hz, 2H), 3.46~3.42 (t, J=7.6 Hz, 2H), 1.68~1.64 (m, 2H), 1.45~1.40 (m, 2H), 1.28~1.25 (t, J=7.2 Hz, 3H), 1.02~0.99 (t, J=7.6 Hz, 3H); MS (m/e): 388.5 (M+1)

Compound 28:

$^1$H NMR (DMSO-$d_6$, 400 MHz): δ 9.76 (s, 1H), 8.91 (s, 1H), 8.53 (s, 1H), 8.49 (s, 1H), 8.04 (s, 1H), 7.90 (d, J=8 Hz, 1H), 7.75 (d, J=8.8 Hz, 1H), 7.39 (t, J=8.0 Hz, 1H), 7.20 (d, J=7.6 Hz, 1H), 4.19 (s, 1H), 3.50 (s, 8H), 2.43 (s, 4H), 2.16 (s, 6H); MS (m/e): 444 (M+1).

Compound 29:

$^1$H NMR (DMSO-$d_6$, 400 MHz): δ 9.78 (s, 1H), 9.11 (s, 1H), 8.52 (s, 2H), 8.04 (s, 1H), 7.91 (d, J=8 Hz, 2H), 7.69 (t, J=8.0 Hz, 1H), 7.37 (d, J=7.6 Hz, 1H), 7.18 (d, J=7.6 Hz, 1H), 4.19 (s, 1H), 3.65-3.23 (m, 12H), 3.14 (s, 3H); MS (m/e): 431 (M+1)

Compound 30:

$^1$H NMR (DMSO-$d_6$, 400 MHz): δ 9.78 (s, 1H), 9.15 (s, 1H), 8.50 (s, 1H), 8.41 (s, 1H), 8.03 (s, 1H), 7.88 (d, J=8 Hz, 1H), 7.84 (d, J=8.8 Hz, 1H), 7.70 (d, J=8.8 Hz, 1H), 7.38 (t, J=8.0 Hz, 1H), 7.20 (d, J=7.6 Hz, 1H), 6.45 (t, J=2.4 Hz, 1H), 4.19 (s, 1H), 2.38 (t, J=6.4 Hz, 6H), 1.52 (m, J=5.2 Hz, 4H), 1.40 (m, 2H), 1.23 (s, 2H); MS (m/e): 415 (M+1)

Compound 32:

$^1$H NMR (DMSO-$d_6$, 400 MHz): δ 9.77 (s, 1H), 9.01 (s, 1H), 8.50 (s, 1H), 8.40 (s, 1H), 8.02 (s, 1H), 7.85 (t, J=8.0 Hz, 2H), 7.71 (d, J=8.8 Hz, 1H), 7.39 (t, J=8.0 Hz, 1H), 7.20 (d, J=6.8 Hz, 1H), 6.44 (t, J=2.4 Hz, 1H), 4.19 (s, 1H), 3.27 (m, 4H), 2.54 (m, 4H), 1.70 (s, 4H); MS (m/e): 401 (M+1)

Compound 33:

$^1$H NMR (DMSO-$d_6$, 400 MHz): δ 9.46 (s, 1H), 8.87 (s, 1H), 8.50 (s, 1H), 8.44 (s, 1H), 8.03 (s, 1H), 7.88 (d, J=8 Hz, 2H), 7.70 (d, J=5.2 Hz, 1H), 7.38 (t, J=8.0 Hz, 2H), 7.20 (d, J=8 Hz, 2H), 4.21 (s, 1H), 3.20 (m, 2H), 2.95 (m, 2H); MS (m/e): 398 (M+1)

Compound 34:

$^1$H NMR (CDCl$_3$, 400 MHz): δ 9.79 (s, 1H), 8.50 (s, 1H), 8.45~8.36 (m, 2H), 8.05 (s, 1H), 7.97~7.95 (d, J=8.4 Hz, 1H), 7.92~7.90 (d, J=8.4 Hz, 1H), 7.68~7.65 (d, J=8.8 Hz, 1H), 7.38~7.34 (t, J=7.6 Hz, 1H), 7.19~7.17 (d, J=7.6 Hz, 1H), 4.19 (s, 1H), 3.58~3.56 (m, 2H), 1.74~1.60 (m, 4H), 1.26~1.23 (m, 6H), 0.91~0.86 (m, 6H); MS (m/e): 416.5 (M+1)

Compound 35:

$^1$H NMR (CDCl$_3$, 400 MHz): δ 9.86 (s, 1H), 9.20 (s, 1H), 8.56~8.56 (d, J=2 Hz, 1H), 8.53 (s, 1H), 8.06 (s, 1H), 7.98~7.95 (dd, J=2 Hz, 8.8 Hz, 1H), 7.93~7.91 (d, J=8.4 Hz, 1H), 7.73~7.70 (d, J=8.8 Hz, 1H), 7.39~7.35 (t, J=7.2 Hz, 1H), 7.20~7.18 (d, J=7.6 Hz, 1H), 4.20 (s, 1H), 3.79~3.75 (t, J=6.8 Hz, 4H), 2.85~2.82 (t, J=6.8 Hz, 4H); MS (m/e): 410.4 (M+1)

Compound 36:

$^1$H NMR (CDCl$_3$ MHz): δ 9.77 (s, 1H), 8.69 (s, 1H), 8.53~8.51 (m, 2H), 8.05 (s, 1H), 7.95~7.89 (m, 2H), 7.69~7.67 (d, J=8.8, 1H), 7.39~7.35 (t, J=7.2 Hz, 1H), 7.19~7.17 (d, J=7.2 Hz, 1H), 4.19 (s, 1H), 2.98 (s, 3H), 1.51~1.50 (m, 2H), 1.26~1.25 (m, 6H), 0.84 (s, 3H); MS (m/e): 402.5 (M+1)

Compound 37:

$^1$H NMR (CD3OD, 400 MHz): δ 8.50 (s, 1H), 8.40~8.40 (d, J=2.0 Hz, 1H), 7.97 (s, 1H), 7.80~7.77 (m, 2H), 7.74~7.71 (d, J=9.2 Hz, 1H), 7.38~7.36 (t, J=8.0 Hz, 1H), 7.28~7.27 (d, J=7.6 Hz, 1H), 4.29~4.29 (d, J=2.4 Hz, 2H), 3.53 (s, 1H), 3.18 (s, 3H), 2.75~2.73 (t, J=2.4 Hz, 1H); MS (m/e): 356.4 (M+1)

Compound 38:

$^1$H NMR (DMSO-$d_6$, 400 MHz): δ 8.51 (s, 1H), 8.49 (s, 1H), 7.94 (s, 1H), 7.91~7.88 (dd, J=1.6 Hz, 9.2 Hz, 1H), 7.80~7.78 (d, J=8.8 Hz, 1H), 7.76~7.76 (d, J=0.8 Hz, 1H), 7.46~7.44 (t, J=8.8 Hz, 1H), 7.38~7.36 (t, J=7.6 Hz, 1H), 7.29~7.28 (m, 1H), 7.27~7.24 (t, J=8.4 Hz, 1H), 4.60 (s, 4H), 3.51 (s, 1H); MS (m/e): 382.4 (M+1)

Compound 39:

$^1$H NMR (CDCl$_3$, 400 MHz): δ 9.78 (s, 1H), 8.77 (s, 1H), 8.53~8.52 (d, J=2 Hz, 1H), 8.51 (s, 1H), 8.04 (s, 1H), 7.94~7.88 (m, 2H), 7.70~7.68 (d, J=8.8 Hz, 1H), 7.39~7.353 (t, J=8 Hz, 1H), 7.19~7.17 (d, J=7.6 Hz, 1H), 5.84~5.79 (m, 1H), 5.22~5.16 (m, 2H), 4.19 (s, 1H), 4.02~4.01 (d, J=4.8 Hz, 2H), 2.97 (s, 1H); MS (m/e): 357.4 (M+1)

Compound 40:
$^1$H NMR (DMSO-$d_6$, 400 MHz): δ 9.81 (s, 1H), 9.23 (s, 1H), 8.52 (s, 2H), 8.49 (s, 1H), 8.04 (s, 1H), 7.90 (m, 2H), 7.70 (d, J=8.8 Hz, 1H), 7.37 (t, J=7.6 Hz, 1H) 7.18 (d, J=7.6 Hz, 1H), 4.19 (s, 1H), 3.87 (t, J=8 Hz, 2H), 3.59 (s, 2H), 2.06 (m, 2) 1.72 (s, 2H); MS (m/e): 408 (M+1).

Compound 41:
$^1$H NMR (DMSO-$d_6$, 400 MHz): δ 9.78 (s, 1H), 9.11 (s, 1H), 8.51 (s, 2H), 8.04 (s, 1H), 7.90 (d, J=8.8 Hz, 2H), 7.69 (d, J=8.8 Hz, 1H), 7.37 (t, J=8.0 Hz, 1H), 7.18 (d, J=8.8 Hz, 1H), 4.19 (s, 1H), 3.68 (m, 4H), 2.59 (m, 6H), 1.07 (m, 3H); MS (m/e): 401 (M+1).

Compound 42:
$^1$H NMR (DMSO-$d_6$, 400 MHz): δ 9.77 (s, 1H), 9.13 (s, 1H), 8.51 (s, 2H), 8.04 (s, 1H), 7.92 (t, J=7.6 Hz, 2H), 7.69 (d, J=8.8 Hz, 1H), 7.37 (t, J=8.0 Hz, 1H), 7.18 (d, J=6.0 Hz, 1H), 4.19 (s, 1H), 3.88 (s, 4H), 3.59 (t, J=5.2 Hz, 4H), 1.64 (t, J=5.2 Hz, 4H); MS (m/e): 430 (M+1).

Compound 43:
$^1$H NMR (DMSO-$d_6$, 400 MHz): δ 9.76 (s, 1H), 9.92 (s, 1H), 8.51 (s, 2H), 8.04 (s, 1H), 7.90 (d, J=8 Hz, 2H), 7.68 (d, J=8.8 Hz, 1H), 7.37 (t, J=8.0 Hz, 1H), 7.17 (d, J=8.8 Hz, 1H), 4.19 (s, 1H), 2.76 (t, J=12 Hz, 1H), 2.41 (t, J=10.8 Hz, 6H), 1.66-1.42 (m, 6H), 1.22~1.07 (m, 8H); MS (m/e): 428 (M+1).

Compound 44:
$^1$H NMR (DMSO-$d_6$, 400 MHz): δ 9.77 (s, 1H), 8.90 (s, 1H), 8.51 (d, J=6.8 Hz, 2H), 8.03 (s, 1H), 7.87 (t, J=8.8 Hz, 2H), 7.71 (d, J=8.8 Hz, 1H), 7.37 (t, J=8.0 Hz, 1H), 7.18 (d, J=8 Hz, 1H), 4.18 (s, 1H), 3.67 (m, 8H), 1.15 (d, J=2.0 Hz, 1H), 0.79 (m, 4H); MS (m/e): 441 (M+1).

Compound 45:
$^1$H NMR (DMSO-$d_6$, 400 MHz): δ 9.79 (s, 1H), 9.18 (s, 1H), 8.54 (d, J=4.4 Hz, 2H), 8.05 (s, 1H), 7.89 (m, 2H), 7.74~7.71 (d, J=8.8 Hz, 1H), 7.41~7.37 (t, J=8.0 Hz, 1H), 7.21~7.19 (d, J=7.6 Hz, 1H), 4.20 (s, 1H), 3.65 (bs, 4H), 3.18 (bs, 4H), 2.94 (s, 3H); MS (m/e): 451.5 (M+1).

Compound 46:
$^1$H NMR (CD$_3$OD, 400 MHz): δ 8.51 (s 1H), 8.06 (s 1H), 8.05 (s, 1H), 7.68-7.80 (d, J=9.2 Hz, 3H), 7.39-7.42 (t, J=8.0 Hz, 1H), 7.29-7.31 (d, J=3.2 Hz, 1H), 7.20-7.20 (d, J=0.4 Hz, 1H), 4.08-4.12 (t, J=8.0 Hz, 2H), 3.67-3.73 (t, J=8.0 Hz, 2H); MS (m/e): 348.1 (M+1).

Compound 47:
$^1$H NMR (DMSO-$d_6$, 400 MHz): δ 9.82 (s, 1H), 8.93 (s, 1H), 8.52~8.46 (m, 4H), 8.03 (s, 1H), 7.90~7.88 (m, 2H), 7.72~7.70 (m, 2H), 7.37 (s, 2H), 7.19~7.18 (m, 1H), 4.74 (s, 2H), 4.20 (s, 1H), 3.33~3.35 (m, 2H), 1.07~1.05 (m, 1H), 0.42~0.41 (m, 2H), 0.23~0.19 (m, 2H); MS (m/e): 449.5 (M+1)

Compound 48:
$^1$H NMR (CDCl$_3$, 400 MHz): δ 9.78 (s, 1H), 8.70 (s, 1H), 8.53~8.48 (m, 4H), 8.02~7.97 (m, 2H), 7.88~7.84 (m, 1H), 7.74~7.65 (m, 2H), 7.32 (s, 2H), 7.19 (s, 1H), 4.54 (s, 2H), 4.19 (s, 1H), 2.65~2.58 (m, 1H), 0.96~0.89 (m, 2H), 0.76~0.75 (m, 2H); MS (m/e): 435.5 (M+1)

Compound 49:
$^1$H NMR (DMSO-$d_6$, 400 MHz): δ 9.79 (s, 1H), 9.04 (s, 1H), 8.50 (s, 1H), 8.41 (s, 1H), 8.03 (s, 1H), 7.90~7.84 (m, 2H), 7.71~7.69 (d, J=8.8 Hz, 1H), 7.41-7.37 (t, J=8.0 Hz, 1H), 7.21~7.19 (d, J=7.6 Hz, 1H), 6.82~6.80 (d, J=8.0 Hz, 1H), 4.20 (s, 1H), 3.87~3.82 (m, 2H), 3.75~3.73 (bs, 1H), 3.43~3.38 (t, J=9.2 Hz, 2H), 1.85-1.81 (d, J=5.6 Hz, 2H), 1.44~1.40 (m, 2H); MS (m/e): 388.4 (M+1).

Compound 50:
$^1$H NMR (DMSO-$d_6$, 400 MHz): δ 9.79 (s, 1H), 9.09~9.05 (m, 1H), 8.50 (s, 1H), 8.41 (s, 1H), 8.03 (s, 1H), 7.89~7.84 (m, 2H), 7.72~7.70 (d, J=9.2 Hz, 1H), 7.41~7.37 (t, J=8.0 Hz, 1H), 7.21~7.19 (d, J=7.2 Hz, 1H), 6.69~6.65 (m, 1H), 4.20 (s, 1H), 3.73~3.40 (t, J=7.2 Hz, 2H), 2.62~2.59 (t, J=7.2 Hz, 2H), 2.10 (s, 3H); MS (m/e): 378.4 (M+1).

Compound 51:
$^1$H NMR (DMSO-$d_6$, 400 MHz): δ 9.79 (s, 1H), 9.02 (s, 1H), 8.50 (s, 1H), 8.41 (s, 1H), 8.03 (s, 1H), 7.89~7.84 (m, 2H), 7.71~7.69 (d, J=8.8 Hz, 1H), 7.41~7.37 (t, J=8.8 Hz, 1H), 7.21~7.19 (d, J=7.2 Hz, 1H), 6.69 (m, 1H), 4.20 (s, 1H), 3.24~3.20 (t, J=6.8 Hz, 2H), 2.55~2.53 (t, J=7.2 Hz, 2H), 2.06 (s, 3H), 2.55~2.53 (tt, J=6.8 Hz, 7.2 Hz, 2H); MS (m/e): 392.5 (M+1).

Compound 52:
$^1$H NMR (DMSO-$d_6$, 400 MHz): δ 9.83 (s, 1H), 9.37 (s, 1H), 8.54 (d, J=8.8, 2H), 8.08 (s, 1H), 7.93 (t, J=8.8 Hz, 2H), 7.74 (d, J=9.2 Hz, 1H), 7.39 (t, J=8.0 Hz, 1H), 7.20 (d, J=7.6 Hz, 1H), 4.23 (s, 1H), 3.55 (m, 8H); MS (m/e): 469 (M+1).

Compound 53:
$^1$H NMR (DMSO-$d_6$, 400 MHz): δ 9.77 (s, 1H), 9.01 (s, 1H), 8.52 (d, J=6.8, 2H), 8.05 (s, 1H), 7.88 (m, 2H), 7.72 (d, J=7.2 Hz, 1H), 7.39 (t, J=8.4 Hz, 1H), 7.20 (d, J=7.6 Hz, 1H), 4.20 (s, 1H), 3.66 (d, J=6.4 Hz, 2H), 3.54 (t, J=5.2 Hz, 4H), 2.66 (t, J=4.8 Hz, 4H); MS (m/e): 455 (M+1).

Compound 54:
$^1$H NMR (CD3OD, 400 MHz): δ 8.49 (s, 1H), 8.37 (s, 1H), 7.96 (s, 1H), 7.81~7.79 (d, J=7.2 Hz, 1H), 7.74~7.73 (m, 2H), 7.40~7.36 (t, J=8.0 Hz, 1H), 7.27~7.25 (d, J=7.2 Hz, 1H), 3.64~3.62 (bs, 4H), 3.52 (s, 1H), 2.53~2.51 (bs, 4H), 2.35 (s, 3H); MS (m/e): 387.5 (M+1).

Compound 55:
$^1$H NMR (CD3OD, 400 MHz): δ 8.48 (s, 1H), 8.37 (s, 1H), 7.96 (s, 1H), 7.81~7.79 (d, J=7.2 Hz, 1H), 7.74~7.73 (m, 2H), 7.40~7.36 (t, J=8.0 Hz, 1H), 7.27~7.25 (d, J=7.2 Hz, 1H), 3.64~3.61 (bs, 4H), 3.52 (s, 1H), 2.77~2.74 (m, 1H), 2.64~2.62 (bs, 4H), 1.12~1.10 (d, J=6.4 Hz, 3H); MS (m/e): 415.5 (M+1).

Compound 56:
$^1$H NMR (CD3OD, 400 MHz): δ 8.48 (s, 1H), 8.37 (s, 1H), 7.96 (s, 1H), 7.81~7.79 (d, J=7.2 Hz, 1H), 7.74~7.73 (m, 2H), 7.40~7.36 (t, J=8.0 Hz, 1H), 7.27~7.25 (d, J=7.2 Hz, 1H), 4.34~4.31 (d, J=13.6 Hz, 2H), 3.51 (s, 1H), 297~2.91 (t, J=12.4 Hz, 2H), 2.52~2.48 (m, 1H), 2.33 (s, 6H), 2.00~1.97 (d, J=11.6 Hz, 2H), 1.49~1.45 (m, 2H); MS (m/e): 415.5 (M+1).

Compound 57:
$^1$H NMR (CD3OD, 400 MHz): δ 8.48 (s, 1H), 8.37 (s, 1H), 7.96 (s, 1H), 7.81~7.79 (d, J=7.2 Hz, 1H), 7.74~7.73 (m, 2H), 7.40~7.36 (t, J=8.0 Hz, 1H), 7.27~7.25 (d, J=7.2 Hz, 1H), 4.34~4.31 (d, J=13.6 Hz, 2H), 3.51 (s, 1H), 2.98~2.91 (t, J=13.2 Hz, 3H), 2.73 (m, 4H), 1.96~1.93 (d, J=12.4 Hz, 2H), 1.56~1.53 (m, 2H), 1.14~1.10 (t, J=7.6 Hz, 6H); MS (m/e): 443.5 (M+1).

Compound 58:
MS (m/e): 443 (M+1).

Compound 59:
MS (m/e): 45.2 (M+1).

Example 60

Synthesis of N-(4-(3-ethynylphenylamino)-7-fluoro-quinazolin-6-yl)piperidine-1-carboxamide (Compound 60)

The synthetic route to Compound 60 is shown below:

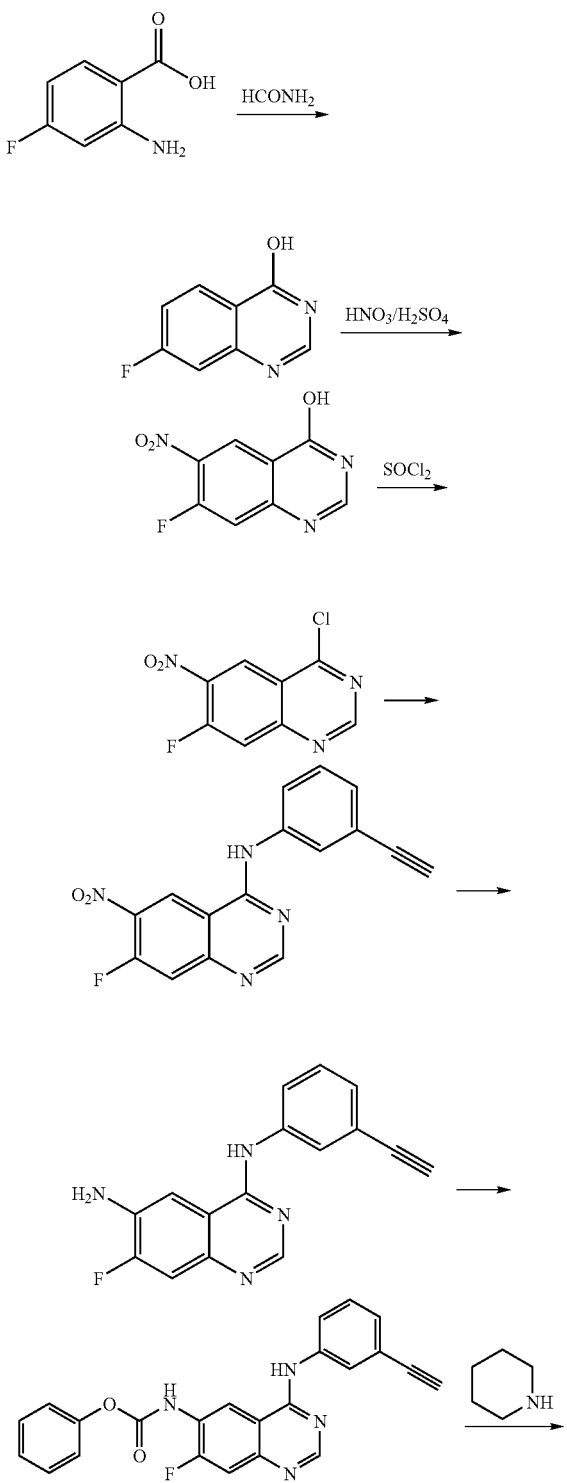

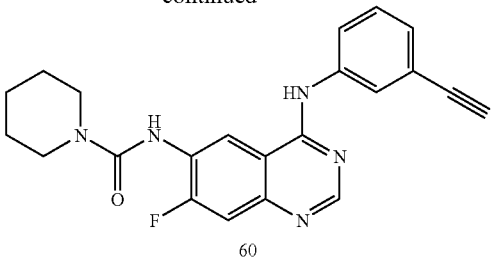

2-Amino-4-fluorobenzoic acid (1.55 g, 10 mmol) in formamide (5 mL) was heated to 150° C. for 6 h. The mixture was cooled to room temperature with stirring. The precipitate was filtered out and washed with ethyl ether to give 1.3 g of 7-fluoroquinazolin-4-ol (78%).

7-Fluoroquinazolin-4-ol (1 g, 6.0 mmol) was dissolved in concentrated $H_2SO_4$ (3 mL) at 0° C. Concentrated $HNO_3$ (3 mL) was added dropwise with stirring in 15 min. The mixture was heated to 100° C. for 3 h, and poured into ice-water with stirring after cooled to room temperature. The precipitate was filtered out and recrystallized with HOAc to give 0.60 g of 7-fluoro-6-nitroquinazolin-4-ol (38%).

7-Fluoro-6-nitroquinazolin-4-ol (518 mg, 2 mmol) was dissolved into thionyl chloride (3 mL) contain 2 drops of DMF. The solution was refluxed for 3 h and then the solvent was removed under reduced pressure. The residue, 4-chloro-7-fluoro-6-nitroquinazoline, was used directly in the next step without purification.

4-Chloro-7-fluoro-6-nitroquinazoline and 3-ethynylbenzenamine (234 mg, 2 mmol) was dissolved into isopropanol (5 mL) and refluxed for 3 h. After cooled to room temperature, the precipitate was filtered out and washed with water to give 0.59 g of N-(3-ethynylphenyl)-7-fluoro-6-nitroquinazolin-4-amine (95%).

A mixture of N-(3-ethynylphenyl)-7-fluoro-6-nitroquinazolin-4-amine (310 mg, 1 mmol) and $SnCl_2.2H_2O$ (171 mg, 4.5 mmol) in ethyl acetate (35 mL) was refluxed for 2 h. After cooled to room temperature, the mixture was treated with 5% aqueous $NaHCO_3$ to adjust its pH value to 9-10. It was then subjected to extraction with EtOAc. The combined organic layers were washed with saturated brine and $H_2O$ and dried. The solvent was removed under reduced pressure to give 225 mg (81%) N4-(3-ethynylphenyl)-7-fluoroquinazoline-4,6-diamine as a yellow solid.

N4-(3-ethynylphenyl)-7-fluoroquinazoline-4,6-diamine (100 mg, 0.36 mmol) was dissolved into DMF (3 mL) containing pyridine (35 μL, 0.432 mmol). Phenyl chloroformate (46 μL, 0.36 mmol) was dropped into the mixture at room temperature and heated to 70° C. for 1 h to give phenyl 4-(3-ethynylphenylamino)-7-fluoroquinazolin-6-ylcarbamate. The obtained compound was used in the next step directly without purification. Then the amine (0.36 mmol) was added and stirred at 70° C. for 2.5 h. After cooled to room temperature, the reaction mixture was diluted with ethyl acetate and washed with water. The combined organic layers were concentrated and purified with silica column to give Compound 60 (105 mg, 75% yield).

$^1$H NMR (DMSO-$d_6$, 400 MHz): δ 10.22 (s, 1H), 8.70 (s, 1H), 8.66 (s, 1H), 8.63 (s 1H), 8.02 (s, 1H), 7.90 (d, J=8 Hz, 1H), 7.62 (d, J=12 Hz, 1H), 7.42 (t, J=8.4 Hz, 1H), 7.25 (d, J=7.6 Hz, 1H), 4.23 (s, 1H), 3.49 (m, 4H), 1.53 (m, 6H); MS (m/e): 390 (M+1).

Examples 61-65

Synthesis of Compounds 61-65

Compounds 61-65 were prepared in a manner similar to that described in Example 60.

Compound 61:

$^1$H NMR (DMSO-d$_6$, 400 MHz): δ 9.88 (s, 1H), 8.71 (s, 1H), 8.59 (d, J=6.4 Hz, 2H), 8.05 (s 1H), 7.90 (d, J=9.2 Hz, 1H), 7.61 (d, J=7.6 Hz, 1H), 7.41 (t, J=8.0 Hz, 1H), 7.24 (d, J=8.8 Hz, 1H), 4.22 (s, 1H), 3.65 (m, 4H), 3.49 (m, 6H); MS (m/e): 392 (M+1).

Compound 62:

$^1$H NMR (DMSO-d$_6$, 400 MHz): δ 10.04 (s, 1H), 8.79 (s, 1H), 8.67 (d, J=0.4 Hz, 1H), 8.56 (s, 1H), 8.07 (s, 1H), 7.92 (d, J=8.8 Hz, 1H), 7.60 (d, J=10.8 Hz, H), 7.41 (m, 2H), 7.23 (d, J=7.6 Hz, 1H), 7.12 (m, 3H), 4.62 (s, 1H), 4.23 (s, 1H), 3.01 (s, 1H); MS (m/e): 444 (M+1).

Compound 63:

$^1$H NMR (DMSO-d$_6$, 400 MHz): δ 10.00 (s, 1H), 8.83 (s, 1H), 8.73 (d, J=4 Hz, 1H), 8.56 (s, 1H), 8.00 (s, 1H), 7.78 (d, J=8 Hz, 1H), 7.61 (d, J=12 Hz, 1H), 7.40 (m, J=7.6 Hz, 1H), 7.23 (d, J=7.2 Hz, 1H), 4.22 (s, 1H), 3.57 (s, 8H), 3.37 (s, 6H); MS (m/e): 438 (M+1).

Compound 64:

$^1$H NMR (DMSO-d$_6$, 400 MHz): δ 9.96 (s, 1H), 8.67 (s, 1H), 8.59 (s, 1H), 8.60 (s, 1H), 8.39 (s, 1H), 8.05 (d, J=8.4 Hz, 1H), 7.91 (d, J=8.8 Hz, 1H), 7.59 (d, J=10.8 Hz, 1H), 7.39 (d, J=7.6 Hz, 1H), 7.22 (d, J=6 Hz, 1H), 7.13 (d, J=2.0 Hz, 1H), 4.22 (s, 1H), 3.68 (m, 4H), 2.22 (s, 6H), 1.80 (m, 2H); MS (m/e): 419 (M+1).

Compound 65:

$^1$H NMR (DMSO-d$_6$, 400 MHz): δ 9.93 (s, 1H), 8.73 (s, 1H), 8.58 (s, 2H), 8.06 (s, 1H), 7.91 (d, J=8.0 Hz, 1H), 7.58 (d, J=8.8 Hz, 1H), 7.40 (t, J=6.8 Hz, 1H), 7.23 (d, J=8 Hz, 1H), 4.22 (s, 1H), 2.92 (t, J=5.2 Hz, 2H), 2.51 (m, 4H), 1.99-1.91 (m, 4H), 1.72-1.42 (m, 4H), 1.23-1.16 (m, 4H); MS (m/e): 459 (M+1).

Example 66

Synthesis of N-(4-(3-ethynylphenylamino)-7-methoxyquinazolin-6-yl)piperidine-1-carboxamide (Compound 66)

The synthetic route to Compound 62 is shown below:

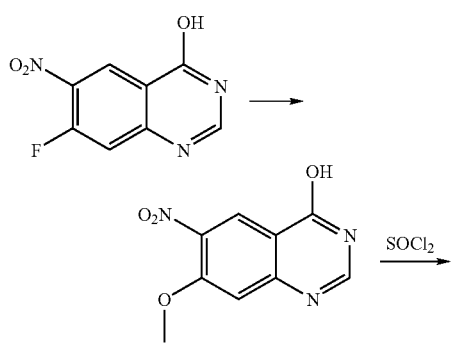

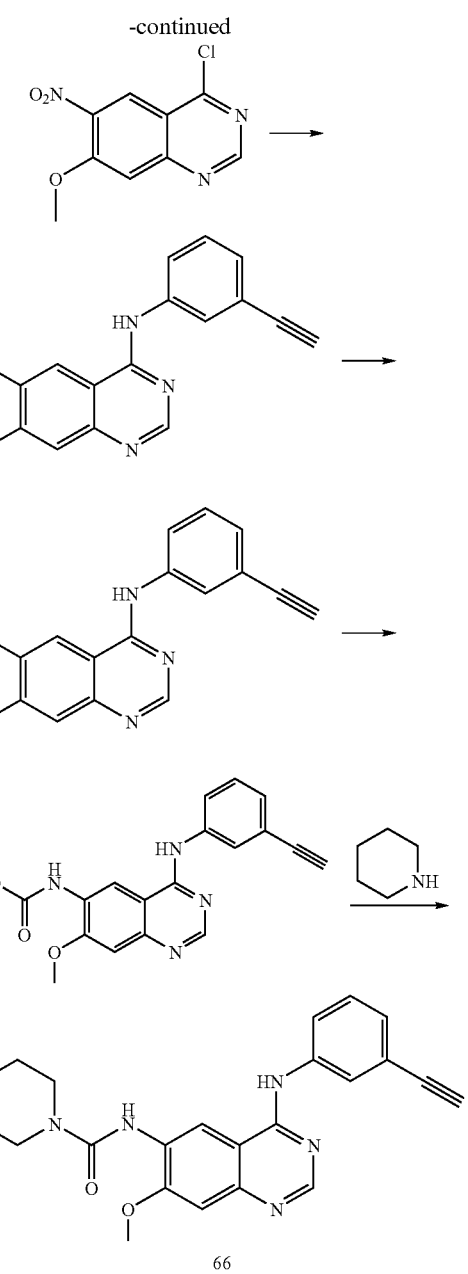

Sodium (92 mg, 4 mmol) was dissolved in methanol (4 mL) under nitrogen at 0° C. 7-Fluoro-6-nitroquinazolin-4-ol (418 mg, 2 mmol) was added. The mixture was refluxed for 3 h and then cooled to room temperature, and treated with 2N HCl to adjust its pH to 3-4. The solution was concentrated, and the residue was diluted with ethyl acetate, and washed with water twice. The organic solution was concentrated to give 7-methoxy-6-nitroquinazolin-4-ol (405 mg, yield: 92%).

7-Methoxy-6-nitroquinazolin-4-ol was transformed to Compound 66 in a manner similar to that described in Example 60.

$^1$H NMR (DMSO-d6, 400 MHz): 9.81 (s, 1H), 8.59 (s, 1H), 8.53 (s, 1H), 8.02 (s, 1H), 7.98 (s, 1H), 7.89 (d, J=8.8 Hz, 1H), 7.38 (t, J=8 Hz, 1H), 7.25 (s, 1H), 7.19 (d, J=7.6 Hz, 1H), 4.21 (s, 1H), 3.98 (s, 3H), 3.53-3.51 (m, 4H), 1.60-1.53 (s, 6H); MS (m/e): 402 (M+1).

Examples 67-84

Synthesis of Compounds 67-84

Compounds 67~84 were prepared in a manner similar to that described in Example 66.

Compound 67:
$^1$H NMR (DMSO-d$_6$, 400 MHz): 9.69 (s, 1H), 8.58 (s, 1H), 8.54 (s, 1H), 8.10 (s, 1H), 8.04 (s, 1H), 7.90 (d, J=8.8 Hz, 1H), 7.38 (t, J=8 Hz, 1H), 7.26 (s, 1H), 7.19 (d, J=7.2 Hz, 1H), 4.19 (s, 1H), 3.99 (s, 3H), 3.64 (t, J=4.8 Hz, 4H), 3.49 (s, J=4.8 Hz, 4H); MS (m/e): 404 (M+1).

Compound 68:
$^1$H NMR (DMSO-d$_6$, 400 MHz): 9.71 (s, 1H), 8.57 (s, 1H), 8.52 (s, 1H), 8.07 (s, 1H), 8.04 (s, 1H), 7.91 (d, J=8.8 Hz, 1H), 7.37 (t, J=6.4 Hz, 1H), 7.24 (s, 1H), 7.18 (d, J=5.2 Hz, 1H), 4.19 (s, 1H), 3.98 (s, 3H), 3.50 (m, 4H), 2.48 (m, 6H), 1.04 (s, 3H); MS (m/e): 431 (M+1).

Compound 69:
$^1$H NMR (DMSO-d$_6$, 400 MHz): 9.65 (s, 1H), 8.73 (s, 1H), 8.57 (s, 1H), 8.49 (s, 1H), 8.00 (s, 1H), 7.87 (d, J=7.6 Hz, 1H), 7.37 (t, J=8 Hz, 1H), 7.24 (s, 1H), 7.17 (d, J=7.6 Hz, 1H), 4.19 (s, 1H), 4.01 (s, 3H), 3.56 (s, 8H), 3.36 (s, 6H); MS (m/e): 450 (M+1).

Compound 70:
$^1$H NMR (DMSO-d$_6$, 400 MHz): 9.73 (s, 1H), 8.66 (s, 1H), 8.53 (s, 1H), 8.49 (s, 1H), 8.03 (s, 1H), 7.98 (s, 1H), 7.89 (d, J=7.2 Hz, 1H), 7.46-7.36 (m, 3H), 7.25-7.13 (m, 6H), 4.63 (s, 2H), 4.19 (s, 1H), 3.98 (s, 3H), 3.04 (s, 3H); MS (m/e): 456 (M+1).

Compound 71:
$^1$H NMR (DMSO-d$_6$, 400 MHz): 9.66 (s, 1H), 8.88 (s, 1H), 8.48 (s, 1H), 8.41 (s, 1H), 7.98 (s, 1H), 7.85 (d, J=8.0 Hz, 1H), 7.37 (t, J=8.0 Hz, 1H), 7.12 (s, 1H), 7.15 (d, J=7.2 Hz, 1H), 4.18 (s, 1H), 4.03 (s, 3H), 3.43-3.30 (m, 7H); MS (m/e): 392 (M+1).

Compound 72:
$^1$H NMR (DMSO-d$_6$, 400 MHz): 9.76 (s, 1H), 8.62 (s, 1H), 8.51 (s, 1H), 8.36 (s, 1H), 8.00 (s, 1H), 7.87 (d, J=7.6 Hz, 1H), 7.37 (t, J=8.0 Hz, 1H), 7.26 (s, 1H), 7.18 (d, J=7.6 Hz, 1H), 4.21 (s, 1H), 4.01 (s, 3H), 3.54 (dd, J=4.0 Hz, 4.0 Hz, 4H), 3.46 (s, 3H), 3.16 (s, 3H); MS (m/e): 406 (M+1).

Compound 73:
$^1$H NMR (DMSO-d$_6$, 400 MHz): 9.68 (s, 1H), 8.57 (s, 1H), 8.50 (s, 1H), 8.04 (s, 1H), 8.00 (s, 1H), 7.89 (d, J=7.6 Hz, 1H), 7.35 (t, J=8.0 Hz, 1H), 7.24 (s, 1H), 7.17 (d, J=7.6 Hz, 1H), 4.20 (s, 1H), 3.98 (s, 3H), 3.42-3.40 (m, 2H), 2.99 (s, 3H), 2.80-2.74 (m, 6H), 1.09 (m, 6H); MS (m/e): 447 (M+1).

Compound 74:
$^1$H NMR (DMSO-d$_6$, 400 MHz): 9.69 (s, 1H), 8.56 (s, 1H), 8.53 (s, 1H), 8.05 (s, 1H), 8.04 (s, 1H), 7.90 (d, J=7.6 Hz, 1H), 7.38 (t, J=8 Hz, 1H), 7.26 (s, 1H), 7.19 (d, J=7.6 Hz, 1H), 4.21 (s, 1H), 3.99 (s, 3H), 3.58 (m, 4H), 2.36 (m, 4H), 2.23 (s, 3H); MS (m/e): 417 (M+1).

Compound 76:
$^1$H NMR (DMSO-d$_6$, 400 MHz): 9.70 (s, 1H), 8.57 (s, 1H), 8.53 (s, 1H), 8.04 (s, 2H), 7.90 (d, J=8.0 Hz, 1H), 7.38 (t, J=8.0 Hz, 1H), 7.25 (s, 1H), 7.19 (d, J=8.0 Hz, 1H), 4.21 (s, 1H), 3.99 (s, 3H), 3.50 (m, 4H), 2.49 (m, 4H), 2.24 (m, 2H), 0.85-0.11 (m, 5H); MS (m/e): 457 (M+1).

Compound 77:
$^1$H NMR (DMSO-d$_6$, 400 MHz): 9.69 (s, 1H), 8.56 (s, 1H), 8.53 (s, 1H), 8.04 (s, 2H), 7.90 (d, J=8.0 Hz, 1H), 7.38 (t, J=8.0 Hz, 1H), 7.25 (s, 1H), 7.19 (d, J=7.6 Hz, 1H), 4.21 (s, 1H), 4.11 (m, 2H), 4.03 (s, 3H), 2.95 (m, 2H), 2.73 (m, 4H), 2.21 (m, 1H), 1.88 (m, 2H), 1.71 (m, 4H), 1.41 (m, 2H); MS (m/e): 458 (M+1).

Compound 79:
$^1$H NMR (DMSO-d$_6$, 400 MHz): 9.69 (s, 1H), 8.56 (s, 1H), 8.53 (s, 1H), 8.04 (s, 2H), 7.90 (d, J=7.6 Hz, 1H), 7.38 (t, J=8.0 Hz, 1H), 7.25 (s, 1H), 7.19 (d, J=7.6 Hz, 1H), 4.21 (s, 1H), 4.14 (m, 2H), 3.99 (s, 3H), 2.86 (m, 2H), 2.20 (s, 6H), 1.78 (m, 2H), 1.35 (m, 2H), 1.24 (m, 1H); MS (m/e): 445 (M+1).

Compound 80:
$^1$H NMR (DMSO-d$_6$, 400 MHz): 9.66 (s, 1H), 8.61 (s, 1H), 8.52 (s, 2H), 8.04 (s, 1H), 7.91 (d, J=7.2 Hz, 1H), 7.38 (t, J=8.0 Hz, 1H), 7.22 (s, 1H), 7.21 (d, J=7.2 Hz, 1H), 4.26 (m, 2H), 4.18 (s, 1H), 3.50 (m, 4H), 2.51 (m, 2H), 2.41 (m, 4H), 1.49 (m, 3H), 1.04 (m, 3H); MS (m/e): 445 (M+1).

Compound 81:
$^1$H NMR (DMSO-d6, 400 MHz): 8.53 (s, 1H), 8.34-8.31 (m, 3H), 7.83 (dd, J=2.0 Hz, J=1.6 Hz, 1H), 7.60 (d, J=9.2 Hz, 1H), 7.47 (s, 1H), 7.7.45 (s, 1H), 7.31 (t, J=7.6 Hz, 2H), 7.21 (t, J=7.2 Hz, 1H), 5.61-5.58 (m, 1H), 3.79-3.77 (m, 1H), 3.66-3.64 (m, 1H), 3.39-3.37 (m, 2H), 3.18-3.17 (m, 2H), 2.40 (s, 6H), 2.25-2.24 (m, 1H), 1.58 (d, J=7.6 Hz, 3H); MS (m/e): 405 (M+1).

Compound 82:
$^1$H NMR (DMSO, 400 MHz): 8.52 (s, 1H), 8.28 (s, 2H), 7.63 (s, 1H), 7.48 (d, J=7.6 Hz, 2H), 7.24-7.14 (m, 4H), 5.80-5.77 (m, 1H), 3.99 (s, 3H), 3.78-3.89 (m, 4H), 3.29-3.22 (m, 2H), 2.33 (s, 6H), 2.25-2.24 (m, 1H), 1.56 (d, J=7.2 Hz, 3H); MS (m/e): 453 (M+1).

Compound 83:
$^1$H NMR (DMSO-d6, 400 MHz): 8.74 (s, 1H), 8.48 (s, 1H), 8.29 (s, 1H), 7.56 (s, 1H), 7.23-7.15 (m, 6H), 3.96 (s, 3H), 3.72-3.57 (m, 3H), 3.32-3.29 (m, 2H), 2.82-2.78 (m, 2H), 2.23 (s, 6H), 1.34 (s, 4H); MS (m/e): 447 (M+1).

Compound 84:
$^1$H NMR (DMSO-d6, 400 MHz): 9.54 (s, 1H), 8.61 (s, 1H), 8.44 (s, 1H), 7.69 (s, 2H), 7.48 (d, J=8.0 Hz, 2H), 7.23-7.19 (m, 3H), 3.99 (s, 3H), 3.80-3.66 (m, 2H), 3.45-3.40 (m, 2H), 3.18-3.06 (m, 3H), 2.90-2.83 (m, 6H), 2.08-2.01 (m, 3H), 1.24-1.18 (m, 3H); MS (m/e): 447 (M+1).

Example 85

Synthesis of 1-(2-(dimethylamino)ethyl)-3-(4-(3-ethynylphenylamino)quinazolin-7-yl)-1-methylurea (Compound 85)

The synthetic route to Compound 85 is shown below:

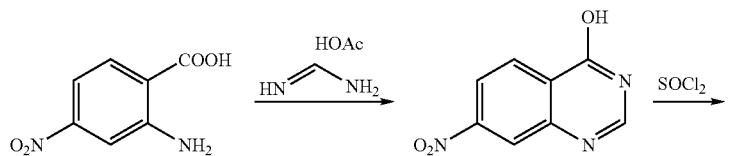

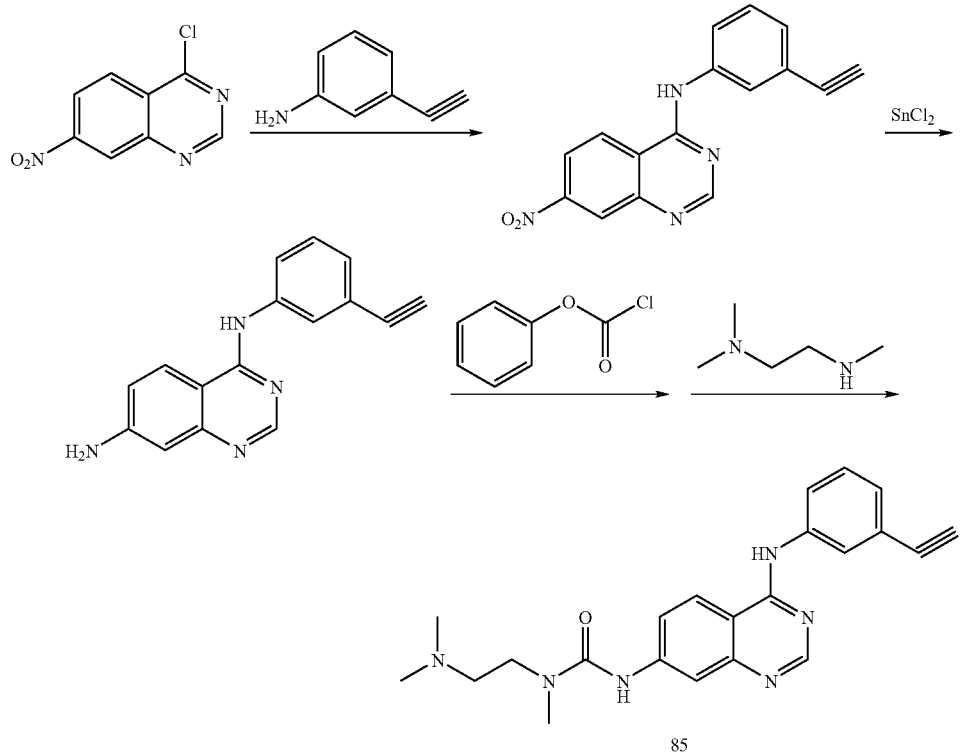

To a solution of 2-amino-4-nitrobenzoic acid (6.00 g, 32.94 mmol) in ethanol (40 mL) was added formamidin acetate (6.80 g, 65.32 mmol). The reaction mixture was refluxed for 5 h. The reaction mixture was cooled to room temperature and refrigerated. The precipitate was filtered out, washed with several portions of cooled ethanol, and then dried in vacuo to give 5.60 g (89%) of 7-nitroquinazolin-4-ol as a yellow solid.

A mixture of 7-nitroquinazolin-4-ol (3.4 g, 17.79 mmol), thionyl chloride (20 mL), and DMF (0.5 mL) was refluxed for 48 h. After the mixture was cooled, excess thionyl chloride was removed by evaporation and the residue was azeotroped with toluene to afford 2.61 g (70%) of 4-chloro-7-nitro-quinazoline as a yellowish solid.

A mixture of 4-chloro-7-nitroquinazoline (2.0 g, 9.54 mmol), isopropanol (30 mL), and 3-ethynylbenzenamine (1.2 g, 10.00 mmol) was refluxed for 5 h. The reaction mixture was cooled to room temperature and refrigerated. The solid was filtered, washed with cold isopropanol several times, and dried in vacuo to give 2.6 g (94%) of N-(3-ethynylphenyl)-7-nitroquinazolin-4-amine as a yellow solid.

A mixture of N-(3-ethynylphenyl)-7-nitroquinazolin-4-amine (2.0 g, 6.89 mmol), $SnCl_2$ (5.0 g, 26.37 mmol), and ethyl acetate (50 mL) was refluxed for 3 h, and then subeject to extraction with ethyl acetate (20 mL) twice. The combined organic layers were washed with brine (20 mL) twice, dried over $Na_2SO_4$, and concentrated in vacuo to afford 1.6 g (86%) of N4-(3-ethynylphenyl)quinazoline-4,7-diamine as a yellow solid.

A mixture of N4-(3-ethynylphenyl)quinazoline-4,7-diamine (48 mg, 0.18 mmol), phenyl carbonochloridate (25.2 μL), pyridine (32 μL), and DMF (2 mL) was stirred at room temperature for 1.5 h. N,N,N-trimethylethane-1,2-diamine (20 mg, 0.19 mmol) was added. The mixture was stirred at 80° C. for 3 h. Then the resulting solution was poured into water and extracted with ethyl acetate (20 mL) 3 times. The combined organic layers were washed with brine (10 mL) twice, dried over $Na_2SO_4$, and concentrated in vacuo to afford 55 mg (78%) of Compound 85 as a yellow solid.

$^1$H NMR (DMSO-$d_6$, 400 MHz): δ 9.92 (s, 1H), 9.66 (s, 1H), 8.69~8.58 (d, J=8.8 Hz, 1H), 8.52 (s, 1H), 8.15 (s, 1H), 8.00~7.98 (dd, J=0.8 Hz, 8.8 Hz, 1H), 7.92~7.91 (d, J=1.6 Hz, 1H), 7.72~7.70 (d, J=9.2 Hz, 1H), 7.39~7.35 (t, J=7.6 Hz, 1H), 7.19~7.17 (d, J=7.6 Hz, 1H), 4.20 (s, 1H), 3.48~3.45 (m, 2H), 3.00 (s, 3H), 2.53~2.48 (m, 2H), 2.28 (s, 6H); MS (m/e): 389.5 (M+1)

Examples 86-90

Synthesis of Compounds 86-90

Compounds 86-90 were prepared in a manner similar to that described in Example 85.

Compound 86:

$^1$H NMR (DMSO-$d_6$, 400 MHz): δ 9.85 (s, 1H), 8.56~8.54 (d, J=9.2, 1H), 8.52 (s, 1H), 8.13 (s, 1H), 7.98~7.96 (d, J=8.8 Hz, 1H), 7.84 (s, 1H), 7.69~7.66 (d, J=9.6 Hz, 1H), 7.40~7.36 (t, J=7.6 Hz, 1H), 7.20~7.18 (d, J=7.5 Hz, 1H), 4.20 (s, 1H), 2.99 (s, 3H), 2.87~2.85 (m, 2H), 2.66~2.56 (m, 6H), 1.03~0.99 (t, J=7.2 Hz, 6H); MS (m/e): 417.5 (M+1).

Compound 87:

$^1$H NMR (DMSO-$d_6$, 400 Hz): δ 9.90 (s, 1H), 8.97 (s, 1H), 8.59~8.457 (d, J=9.2 Hz, 1H), 8.53 (s, 1H), 8.15 (s, 1H), 8.02~8.02 (d, J=1.6 Hz, 1H), 8.00~7.98 (d, J=7.6 Hz, 1H), 7.85~7.83 (dd, J=1.6 Hz, 8.8 Hz, 1H), 7.39~7.35 (t, J=8.0 Hz, 1H), 7.20~7.18 (d, J=7.6 Hz, 1H), 5.88~5.79 (m, 1H), 5.21~5.16 (m, 2H), 4.20 (s, 1H), 4.03~4.02 (d, J=5.2 Hz, 2H), 3.15 (s, 3H); MS (m/e): 358.4 (M+1).

Compound 88:

$^1$H NMR (DMSO-$d_6$, 400 MHz): δ 10.13 (s, 1H), 9.86 (s, 1H), 8.56~8.54 (d, J=9.2 Hz, 1H), 8.52 (s, 1H), 8.12 (s, 1H), 7.97 (s, 1H), 7.95 (s, 1H), 7.58~7.56 (d, J=9.2 Hz, 1H), 7.49~7.46 (t, J=6.4 Hz, 1H), 7.39~7.33 (m, 5H), 7.27~7.23 (m, 1H), 7.20~7.18 (d, J=7.2 Hz, 1H), 4.36~4.34 (d, J=6.0 Hz, 2H), 4.21 (s, 1H); MS (m/e): 394.4 (M+1).

Compound 89:

$^1$H NMR (DMSO-d$_6$, 400 MHz): δ 9.91 (s, 1H), 8.59~8.57 (d, J=9.2 Hz, 1H), 8.53 (s, 1H), 8.14 (s, 1H), 8.02~8.01 (d, J=2.0 Hz, 1H), 7.99~7.98 (d, J=7.6 Hz, 1H), 7.85~7.82 (dd, J=1.6 Hz, 8.8 Hz, 1H), 7.39~7.35 (t, J=8 Hz, 1H), 7.20~7.18 (d, J=8 Hz, 1H), 4.21 (s, 1H), 3.64~3.62 (m, 4H), 3.54~3.52 (m, 4H); MS (m/e): 374.4 (M+1)

Compound 90:

$^1$H NMR (DMSO-d$_6$, 400 MHz): δ 9.73 (s, 1H), 8.79 (s, 1H), 8.54 (s, 1H), 8.46~8.44 (d, J=9.6 Hz, 1H), 8.11 (s, 1H), 7.96 (s, 1H), 7.95~7.93 (d, J=8 Hz, 1H), 7.80~7.77 (t, J=1.2 Hz, 9.2), 7.41~7.37 (t, J=15.2 Hz, 1H), 7.21~7.19 (d, J=8 Hz, 1H), 4.21 (s, 1H), 3.55~3.51 (m, 2H), 3.30 (s, 1H), 3.04 (s, 1H); MS (m/e): 376.4 (M+1).

Example 91

Synthesis of N-(4-(3-ethynylphenylamino)quinazolin-6-yl)-2-(4-methylpiperazin-1-yl)acetamide (Compound 91)

The synthetic route to Compound 91 is shown below.

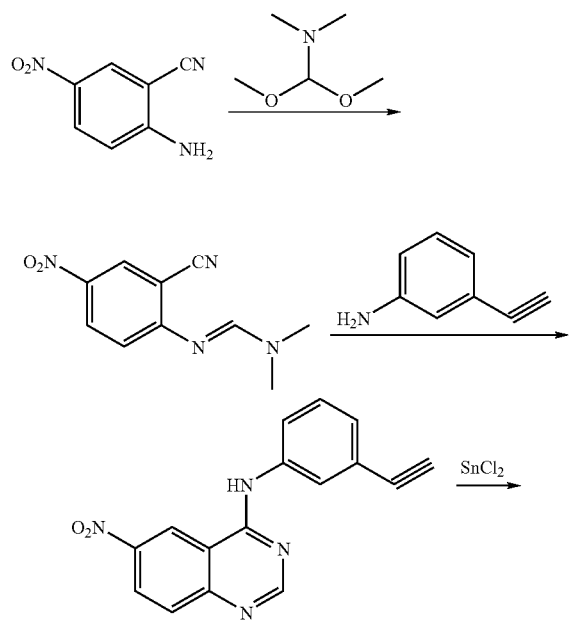

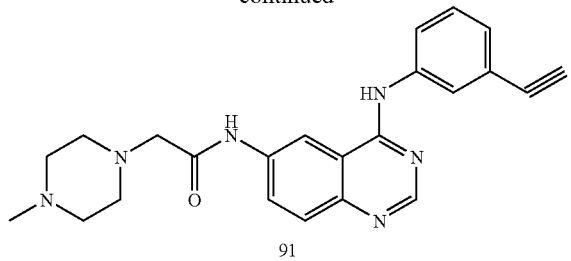

91

To a solution of 5-nitroanthranilonitrile (1.00 g, 6.13 mmol) in dioxane (25 mL) was added dimethylformamide dimethylacetal (0.88 g, 7.36 mmol). The reaction mixture was stirred at 100° C. for 2 h and then cooled to room temperature and refrigerated. The precipitate was filtered out, washed with cold ether several times, and then dried in vacuo to give 1.30 g (97%) of (E)-N'-(2-cyano-4-nitrophenyl)-N,N-dimethylformamidine as a yellow solid.

(E)-N'-(2-cyano-4-nitrophenyl)-N,N-dimethylformamidine (1.00 g, 4.58 mmol) and 3-aminophenylacetylene (0.64 g, 5.49 mmol) was dissolved in HOAc (15 mL). After stirred at 100° C. for 3 h, the resulting mixture was cooled to room temperature. The precipitate was filtered out, washed with ether, and dried in vacuo to give 1.23 g (93%) of N-(3-ethynylphenyl)-6-nitroquinazolin-4-amine as a yellow solid.

A mixture of N-(3-ethynylphenyl)-6-nitroquinazolin-4-amine (1.00 g, 3.45 mmol) and SnCl$_2$.2H$_2$O (3.10 g, 13.8 mmol) in ethyl acetate (35 mL) was refluxed for 2 h and then cooled to room temperature. The pH was adjusted to 9-10 by treatment with 5% aqueous NaHCO$_3$. The mixture was subjected to extraction with EtOAc. The combined organic layers were washed with saturated brine and H$_2$O and dried. The solvent was removed under reduced pressure to give 0.79 g (89%) of N4-(3-ethynylphenyl)quinazoline-4,6-diamine as a yellow solid.

To a solution of N4-(3-ethynylphenyl)quinazoline-4,6-diamine (100 mg, 0.38 mmol) in DMF (2 mL) containing N,N-diisopropylethylamine (124 μL, 0.76 mmol) was added chloroacetyl chloride (32 μL, 0.38 mmol) at room temperature. After 10 min, 1-methylpiperazine (209 μL, 1.90 mmol) was added and the reaction mixture was stirred at 80° C. for 5 h. The reaction mixture was concentrated and the residue was purified by PTLC to give Compound 91 as a yellow solid in 94% yield.

$^1$H NMR (CD$_3$OD, 400 MHz): δ 8.65 (s, 1H), 8.54 (s, 1H), 7.99~7.97 (m, 2H), 7.84~7.79 (m, 2H), 7.43~7.39 (t, J=8.0 Hz, 1H), 7.31~7.29 (d, J=8.0 Hz, 1H), 4.62 (s, 2H), 3.54 (s, 1H), 2.75~2.67 (bs, 8H), 2.41 (s, 3H); MS (m/e): 401.5 (M+1).

Examples 92-125

Synthesis of Compounds 92-125

Compounds 92-125 were prepared in a manner similar to that described in Example 91.

Compound 92:

$^1$H NMR (CD3OD, 400 MHz): 8.59 (d, J=2.0 Hz, 1H), 8.37 (s, 1H), 7.93 (dd, J=2.4 Hz, J=2.4 Hz, 1H), 7.72 (d, J=8.8 Hz, 1H), 7.47 (t, J=6.8 Hz, 1H), 7.28-7.25 (m, 1H), 7.11 (q, 1H), 5.87-5.84 (m, 1H), 3.38 (s, 2H), 3.04 (m, 4H), 2.86 (m, 4H), 2.66 (s, 3H), 1.71 (d, J=7.2 Hz, 3H), MS (m/e): 423 (M+1).

Compound 93:
¹H NMR (DMSO-d₆, 400 MHz): δ 9.99 (s, 1H), 9.88 (s, 1H), 8.66 (s, 1H), 8.57 (s, 1H), 8.06 (d, J=9.2 Hz, 1H), 8.03 (s, 1H), 7.89 (d, J=8.0 Hz, 1H), 7.78 (d, J=8.8 Hz, 1H), 7.41 (t, J=8.0 Hz, 1H), 7.23 (d, J=7.2 Hz, 1H), 4.23 (s, 1H), 3.20 (d, 2H), 3.17 (d, J=4.4 Hz, 1H), 2.60 (m, 8H), 2.6 (m, 8H), 2.35 (t, J=6.8 Hz, 3H); MS (m/e): 415 (M+1).

Compound 94:
¹H NMR (DMSO-d₆, 400 MHz): δ 9.97 (s, 1H), 9.88 (s, 1H), 8.66 (d, J=1.6 Hz, 1H), 8.57 (s, 1H), 8.06 (d, J=9.2 Hz, 1H), 8.03 (s, 1H), 7.89 (d, J=8.0 Hz, 1H), 1H), 7.78 (d, J=9.2 Hz, 1H), 7.41 (t, J=8.0 Hz, 1H), 7.23 (d, J=8.0 Hz, 1H), 4.23 (s, 1H), 3.19 (d, 2H), 2.6 (m, 8H), 0.99 (d, J=6.8 Hz, 6H); MS (m/e): 429 (M+1).

Compound 95:
¹H NMR (DMSO-d₆, 400 MHz): δ 9.96 (s, 1H), 8.79 (s, 1H), 8.58 (s, 1H), 8.12 (d, J=8.8 Hz, 1H), 8.07 (s, 1H), 7.92 (d, J=7.6 Hz, 1H), 7.80 (d, J=8.4 Hz, 1H), 7.40 (t, J=7.2 Hz, 1H), 7.22 (d, J=7.2 Hz, 1H), 4.23 (s, 1H), 3.39 (s, 2H), 2.98 (m, 8H), 1.13 (s, 6H); MS (m/e): 417 (M+1).

Compound 96:
¹H NMR (DMSO-d₆, 400 MHz): δ 9.94 (s, 1H), 8.73 (s, 1H), 8.57 (s, 1H), 8.11 (d, J=6.4 Hz, 1H), 8.05 (s, 1H), 7.90 (d, J=8.0 Hz, 1H), 7.79 (d, J=9.2 Hz, 1H), 2.79 (s, J=7.6 Hz, 1H), 7.21 (d, J=7.6 Hz, 1H), 4.21 (s, 1H), 3.39 (s, 2H), 3.34 (m, 4H), 2.79 (s, 6H); MS (m/e): 389 (M+1).

Compound 97:
MS (m/e): 413.2 (M+1).

Compound 98:
¹H NMR (DMSO, 400 MHz): δ10.09 (s, 1H), 9.92 (s, 1H), 8.62 (s, 1H), 8.57 (s, 1H), 8.10 (d, J=8.8 Hz, 1H), 8.02 (s, 1H), 7.99 (d, J=8.0 Hz, 1H), 7.81 (d, J=8.8 Hz, 1H), 7.41 (t, J=8.0 Hz, 1H), 7.22 (d, J=7.6 Hz, 1H), 4.21 (s, 1H), 3.47 (t, J=4.2 Hz, 4H), 3.39 (s, 2H), 3.26 (s, 6H), 2.85 (t, J=3.9 Hz, 4H); MS (m/e): 434 (M+1).

Compound 99:
¹H NMR (DMSO-d₆, 400 MHz): δ 9.98 (s, 1H), 9.85 (s, 1H), 8.62 (d, J=2.0 Hz, 1H), 8.57 (s, 1H), 8.10 (dd, J=8.8, 2.0 Hz 1H), 8.03 (s, 1H), 7.88 (dd, J=8.4, 1.2 Hz 1H), 7.78 (d, J=9.2 Hz, 1H), 7.41 (t, J=7.6 Hz, 1H), 7.23 (d, J=8.0 Hz, 1H), 4.23 (s, 1H), 3.18 (s, 2H), 2.90 (d, J=12.0 Hz, 2H), 2.48 (s, 3H), 2.22 (t, J=11.2 Hz, 2H), 1.97 (t, J=9.6 Hz, 1H), 1.85 (d, J=12.0 Hz, 2H), 1.67 (d, 4H), 1.55 (m, 2H); MS (m/e): 455 (M+1).

Compound 100:
¹H NMR (DMSO-d₆, 400 MHz): δ 9.98 (s, 1H), 9.86 (s, 1H), 8.64 (d, J=1.6 Hz, 1H), 8.57 (s, 1H), 8.05 (dd, J=8.8, 2.0 Hz 1H), 8.03 (s, 1H), 7.89 (dd, J=8.4, 1.2 Hz 1H), 7.78 (d, J=9.2 Hz, 1H), 7.41 (t, J=8.0 Hz, 1H), 7.23 (d, J=8.0 Hz, 1H), 4.23 (s, 1H), 3.20 (s, 2H), 2.56 (m, 8H), 2.37 (m, 4H), 2.14 (s, 6H); MS (m/e): 458 (M+1).

Compound 102:
MS (m/e): 475 (M+1).

Compound 103:
¹H NMR (DMSO-d₆, 400 MHz): δ 9.97 (s, 1H), 9.86 (s, 1H), 8.64 (d, J=1.6 Hz, 1H), 8.57 (s, 1H), 8.06 (dd, J=9.2, 2.0 Hz 1H), 8.03 (s, 1H), 7.89 (dd, J=8.4, 1.2 Hz 1H), 7.78 (d, J=8.4 Hz, 1H), 7.41 (t, J=8.0 Hz, 1H), 7.23 (d, J=7.6 Hz, 1H), 4.23 (s, 1H), 3.21 (s, 2H), 2.56 (m, 8H), 2.20 (d, J=6.4 Hz, 2H), 1.24 (s, 1H), 0.83 (m, 1H), 0.46 (m, 2H), 0.80 (m, 2H); MS (m/e): 441 (M+1).

Compound 104:
¹H NMR (DMSO-d₆, 400 MHz): δ 9.99 (s, 1H), 9.86 (s, 1H), 8.65 (d, J=1.2 Hz, 1H), 8.57 (s, 1H), 8.06 (dd, J=8.8, 2.0 Hz 1H), 8.03 (s, 1H), 7.89 (dd, J=8.4, 1.2 Hz 1H), 7.79 (d, J=9.2 Hz, 1H), 7.41 (t, J=8.0 Hz, 1H), 7.23 (d, J=7.6 Hz, 1H), 4.23 (s, 1H), 3.38 (s, 2H), 3.17 (d, J=5.2 Hz, 1H), 2.86 (t, J=5.6 Hz, 4H), 2.62 (d, J=4.8 Hz, 4H) 2.31 (s, 3H), 1.80 (m, 2H), 1.24 (s, 1H); MS (m/e): 415 (M+1)

Compound 105:
MS (m/e): 431 (M+1).

Compound 106:
MS (m/e): 427.2 (M+1).

Compound 107:
¹H NMR (DMSO-d₆, 400 MHz): δ 9.94 (s, 1H), 9.84 (s, 1H), 8.63 (s, 1H), 8.55 (s, 1H), 8.03 (m, 2H), 7.88 (d, J=8.0 Hz, 1H), 7.77 (d, j=9.2 Hz, 1H), 7.37 (t, J=8.0 Hz, 1H), 7.20 (d, j=7.6 Hz, 1H), 4.20 (s, 1H), 3.16 (s, 2H), 2.95 (d, j=11.2 Hz, 2H), 2.39 (m, 5H), 2.17 (t, j=8.8 Hz, 2H), 1.62 (m, 4H), 1.35 (m, 4H), 0.83 (t, j=7.6 Hz, 6H); MS (m/e): 485.3 (M+1).

Compound 108:
¹H NMR (DMSO-d₆, 400 MHz): δ10.09 (s, 1H), 9.86 (s, 1H), 8.68 (s, 1H), 8.57 (s, 1H), 8.02 (m, 2H), 7.88 (d, J=8.0 Hz, 1H), 7.79 (d, j=9.2 Hz, 1H), 7.41 (t, J=8.0 Hz, 1H), 7.23 (d, J=7.6 Hz, 1H), 4.20 (s, 1H), 3.78 (s, 2H), 3.58 (s, 2H), 3.28 (s, 2H), 2.63 (s, 2H), 2.51 (s, 2H), 1.99 (s, 1H), 0.73 (m, 4H); MS (m/e): 455.2 (M+1).

Compound 109:
¹H NMR (DMSO-d₆, 400 MHz): δ9.96 (s, 1H), 9.84 (s, 1H), 8.62 (s, 1H), 8.57 (s, 1H), 8.09 (d, J=8.8 Hz, 1H), 8.02 (s, 1H), 7.88 (d, J=8.0 Hz, 1H), 7.79 (t, J=8.8 Hz, 1H), 7.41 (t, J=8.0 Hz, 1H), 7.23 (d, J=8.0 Hz, 1H), 4.22 (s, 1H), 3.57 (m, 1H), 3.17 (s, 2H), 2.80 (m, 2H), 2.30 (m, 2H), 1.78 (m, 2H), 1.54 (m, 2H); MS (m/e): 402.1 (M+1).

Compound 110:
¹H NMR (DMSO-d₆, 400 MHz): δ 9.95 (s, 1H), 9.84 (s, 1H), 8.61 (s, 1H), 8.55 (s, 1H), 8.09 (m, 2H), 7.86 (d, j=8.8 Hz, 1H), 7.76 (d, j=9.2 Hz, 1H), 7.79 (t, j=8.0 Hz, 1H), 7.21 (d, j=7.6 Hz, 1H), 4.21 (s, 1H), 3.42 (t, j=6.0 Hz, 2H), 3.22 (s, 3H), 3.17 (s, 2H), 2.49 (m, 10H); MS (m/e): 445.2 (M+1).

Compound 111:
¹H NMR (DMSO-d₆, 400 MHz): δ 9.95 (s, 1H), 9.84 (s, 1H), 8.64 (s, 1H), 8.57 (s, 1H), 8.08 (d, j=8.8 Hz, 1H), 8.03 (s, 1H), 7.89 (d, j=8.1 Hz, 1H), 7.78 (d, j=9.2 Hz, 1H), 7.40 (t, j=8.4 Hz, 1H), 7.23 (d, j=7.6 Hz, 1H), 4.21 (s, 1H), 3.18 (s, 2H), 2.95 (d, j=10.8 Hz, 2H), 2.40 (s, 3H), 2.30 (m, 4H), 2.18 (m, 7H), 1.76 (m, 2H), 1.56 (m, 2H); MS (m/e): 484.0 (M+1).

Compound 112:
¹H NMR (CD3OD, 400 MHz): δ8.69 (s, 1H), 8.51 (s, 1H), 7.94 (s, 1H), 7.81~7.75 (m, 3H), 7.40~7.36 (t, J=8.0 Hz, 1H), 7.28~7.26 (d, J=8.0 Hz, 1H), 3.51 (s, 1H), 2.86~2.82 (m, 2H), 2.69~2.65 (m, 10H), 1.11~1.09 (d, J=6.0 Hz, 6H); MS (m/e): 443.5 (M+1).

Compound 113:
¹H NMR (CD3OD, 400 MHz): δ8.65 (s, 1H), 8.52 (s, 1H), 7.95~7.89 (m, 2H), 7.81~7.77 (m, 2H), 7.40~7.36 (t, J=8.0 Hz, 1H), 7.29~7.27 (d, J=8.0 Hz, 1H), 3.50 (s, 1H), 2.72 (m, 8H), 1.38~1.36 (d, J=6.8 Hz, 3H), 1.12~1.01 (d, J=6.4 Hz, 6H); MS (m/e): 443.5 (M+1).

Compound 114:
¹H NMR (DMSO-d₆, 400 MHz): 10.27 (s, 1H), 10.04 (s, 1H), 9.28 (s, 1H), 8.58 (s, 1H), 8.44 (d, J=7.2 Hz, 1H), 8.29 (s, 1H), 8.16 (d, J=7.6 Hz, 1H), 7.78 (d, J=8.8 Hz, 1H), 7.39 (t, J=7.6 Hz, 1H), 7.21 (d, J=7.2 Hz, 1H), 4.22 (s, 1H), 2.51 (s, 8H), 1.26 (s, 6H), 1.21 (s, 3H); MS (m/e): 429 (M+1).

Compound 115:
¹H NMR (DMSO-d₆, 400 MHz): δ 9.97 (s, 1H), 9.84 (s, 1H), 8.78 (s, 1H), 8.56 (s, 1H), 8.16 (d, J=9.2 Hz, 1H), 8.07 (s, 1H), 7.93 (d, J=8.4 Hz, 1H), 7.78 (d, J=9.2 Hz, 1H), 7.41 (t, J=8.4 Hz, 1H), 7.22 (d, J=8.0 Hz, 1H), 4.23 (s, 1H), 2.61 (s, 8H), 1.24 (s, 6H), 1.01 (d, J=10.8 Hz, 1H), 0.98-0.96 (m, 1H); MS (m/e): 457 (M+1).

Compound 116:

$^1$H NMR (DMSO-d$_6$, 400 MHz): 9.99 (s, 1H), 9.87 (s, 1H), 8.73 (s, 1H), 8.56 (s, 1H), 8.15 (d, J=7.6 Hz, 1H), 8.08 (s, 1H), 8.7.95 (d, J=7.2 Hz, 1H), 7.78 (d, J=10.2 Hz, 1H), 7.41 (t, J=7.6 Hz, 1H), 7.22 (d, J=8.0 Hz, 1H), 4.23 (s, 1H), 3.15 (d, J=4.8 Hz, 1H) 2.55 (s, 8H), 1.25 (s, 6H), 1.02-0.971 (m, 3H); MS (m/e): 443 (M+1).

Compound 117:

$^1$H NMR (DMSO-d$_6$, 400 MHz): δ 9.86 (s, 1H), 9.42 (s, 1H), 8.68 (s, 1H), 8.57 (s, 1H), 8.18 (d, J=7.2 Hz, 1H), 8.05 (s, 1H), 7.92 (d, J=7.6 Hz, 1H), 7.58 (d, J=7.2 Hz, 1H), 7.39 (t, J=6.0 Hz, 1H), 7.22 (d, J=7.6 Hz, 1H), 6.14 (s, 1H), 4.22 (s, 1H), 3.09~3.06 (m, 2H), 1.49 (s, 3H), 1.32 (s, 6H); MS (m/e): 374 (M+1).

Compound 118:

$^1$H NMR (DMSO-d$_6$, 400 MHz): δ10.00 (s, 1H), 9.82 (s, 1H), 9.04 (s, 1H), 8.52 (s, 1H), 7.96 (s, 1H), 7.85~7.83 (d, J=7.2 Hz, 1H), 7.40~7.36 (t, J=8.0 Hz, 1H), 7.19 (s, 1H), 4.20 (s, 1H), 4.07 (s, 3H), 3.34 (s, 2H), 2.61~2.58 (m, 4H), 2.48~2.36 (m, 4H), 1.05~1.02 (t, J=9.6 Hz, 3H); MS (m/e): 445.5 (M+1).

Compound 119:

$^1$H NMR (DMSO-d$_6$, 400 MHz): δ10.04 (s, 1H), 9.82 (s, 1H), 9.04 (s, 1H), 8.52 (s, 1H), 7.96 (s, 1H), 7.85~7.83 (d, J=7.2 Hz, 1H), 7.40~7.36 (t, J=8.0 Hz, 1H), 7.19 (s, 1H), 4.20 (s, 1H), 4.07 (s, 3H), 3.2 (s, 2H), 2.61~2.58 (m, 4H), 2.48~2.36 (m, 8), 1.10 (bs, 6H); MS (m/e): 459.5 (M+1).

Compound 120:

$^1$H NMR (DMSO-d$_6$, 400 MHz): 10.00 (s, 1H), 9.83 (s, 1H), 9.04 (s, 1H), 8.53 (s, 1H), 7.96 (s, 1H), 7.84 (d, J=7.6 Hz, 1H), 7.38 (t, J=8.0 Hz, 1H), 7.32 (s, 1H), 7.20 (d, J=7.6 Hz, 1H), 4.21 (s, 1H), 4.08 (s, 3H), 3.22 (s, 2H), 2.60 (m, 8H), 2.23 (s, 3H); MS (m/e): 431 (M+1).

Compound 121:

$^1$H NMR (DMSO-d$_6$, 400 MHz): δ10.16 (s, 1H), 9.81 (s, 1H), 9.08 (s, 1H), 8.52 (s, 1H), 7.97 (s, 1H), 7.84 (d, J=8.8 Hz, 1H), 7.38 (t, J=8.0 Hz, 1H), 7.32 (s, 1H), 7.20 (d, J=8.0 Hz, 1H), 4.21 (s, 1H), 4.06 (s, 3H), 3.46 (t, J=5.2 Hz, 1H), 3.26 (s, 3H), 2.76 (t, J=5.2 Hz, 1H), 1.24 (s, 1H); MS (m/e): 406 (M+1).

Compound 123:

$^1$H NMR (CD3OD, 400 MHz): δ8.93 (s, 1H), 8.48 (s, 1H), 7.93 (s, 1H), 7.77 (d, J=8.0 Hz, 1H), 7.38 (t, J=7.6 Hz, 1H), 7.27 (t, J=7.2 Hz, 2H), 4.14 (s, 3H), 3.37 (s, 1H), 3.25 (s, 2H), 3.12-3.09 (m, 3H), 2.42~2.37 (m, 2H), 2.02-2.00 (m, 2H), 1.80-1.77 (m, 2H), 1.31-1.25 (m, 4H), 1.20 (s, 6H); MS (m/e): 487 (M+1).

Compound 124:

$^1$H NMR (DMSO-d$_6$, 400 MHz): δ10.04 (s, 1H), 9.81 (s, 1H), 9.02 (s, 1H), 8.53 (s, 1H), 7.97 (s, 1H), 7.85 (d, J=8.0 Hz, 1H), 7.38 (t, J=8.0 Hz, 1H), 7.32 (s, 1H), 7.20 (d, J=7.6 Hz, 1H), 4.19 (s, 1H), 4.07 (s, 3H), 3.21 (s, 2H), 2.68-2.60 (m, 4H), 1.22 (s, 3H), 1.02-0.97 (m, 6H); MS (m/e): 445 (M+1).

Compound 125:

$^1$H NMR (DMSO-d$_6$, 400 MHz): δ10.52 (s, 1H), 9.94 (s, 1H), 8.95 (s, 1H), 8.57 (s, 1H), 7.99 (s, 1H), 7.86 (d, J=9.2 Hz, 1H), 7.39 (t, J=8.4 Hz, 1H), 7.33 (s, 1H), 6.76 (d, J=7.6 Hz, 1H), 4.23 (s, 1H), 4.04 (s, 3H), 2.98 (s, 8H), 2.78-2.75 (m, 3H), 2.34-2.30 (m, 2H), 1.37 (s, 6H); MS (m/e): 473 (M+1).

Example 126

Synthesis of 1-(4-(3-ethynylphenylamino)quinazolin-6-yl)-3-methyl-1H-imidazol-2 (3H)-one (Compound 126)

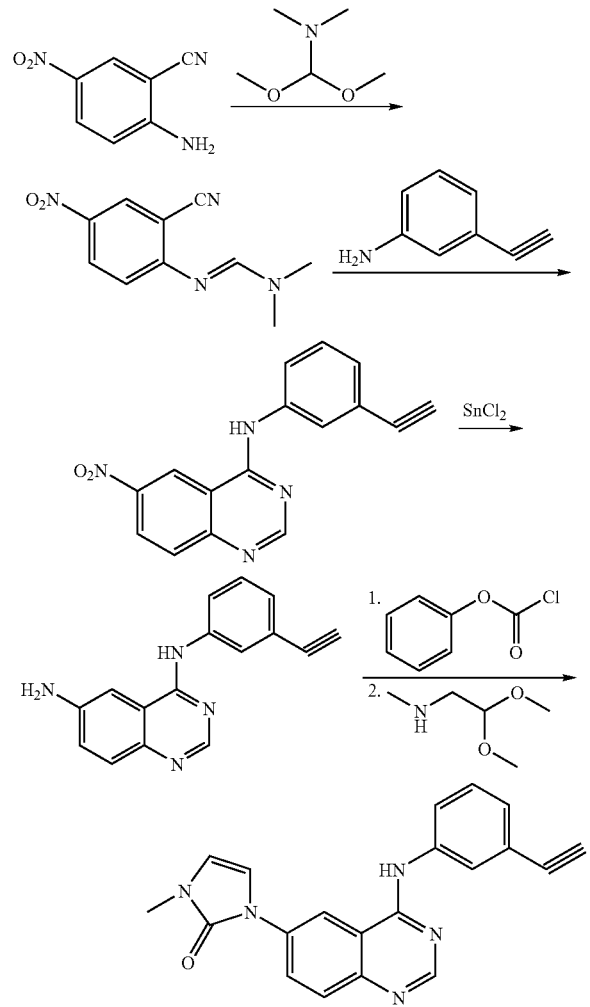

To a solution of 5-nitroanthranilonitrile (1.00 g, 6.13 mmol) in dioxane (25 mL) was added dimethylformamide dimethyl acetal (0.88 g, 7.36 mmol). Th reaction mixture was stirred at 100° C. for 2 h and then cooled to room temperature and refrigerated. The precipitate was filtered out, washed with cold ether several time, and then dried in vacuo to give 1.30 g (97%) of N'-(2-cyano-4-nitrophenyl)-N,N-dimethylformamidine as a yellow solid.

A mixture of N'-(2-cyano-4-nitrophenyl)-N,N-dimethylformamidine (1.00 g, 4.58 mmol) and 3-aminophenylacetylene (0.64 g, 5.49 mmol) in HOAc (15 mL) was stirred at 100° C. for 3 h and cooled to room temperature. The precipitate was filtered, washed with ether, and was dried in vacuo to give 1.23 g (93%) of N-(3-ethynylphenyl)-6-nitroquinazolin-4-amine as a yellow solid.

N-(3-ethynylphenyl)-6-nitroquinazolin-4-amine (1.00 g, 3.45 mmol) and SnCl$_2$.2H$_2$O (3.10 g, 13.8 mmol) in ethyl acetate (35 mL) were refluxed for 2 h. After cooled to room temperature, the mixture was treated with 5% aqueous NaHCO₃ to adjust its pH to 9-10 and then subjected to extraction with EtOAc. The combined organic layers were washed with saturated brine and H₂O, dried, and concentrated under reduced pressure to give 0.79 g (89%) of N4-(3-ethynylphenyl)quinazoline-4,6-diamine as a yellow solid.

To a solution of N4-(3-ethynylphenyl)quinazoline-4,6-diamine (100 mg, 0.38 mmol) in DMF (2 mL) containing pyridine (37 μL, 0.46 mmol) was added phenyl chloroformate (49 μL, 0.38 mmol) dropwise at room temperature. After 10 min, (methylamino)acetaldehyde dimethylacetal (45.2 mg, 0.38 mmol) was added and the reaction mixture was heated to 100° C. for 1 h. After cooled to room temperature, the reaction mixture was diluted with ethyl acetate and washed with water. The combined organic layers were concentrated and purified with a silica column to give Compound 126 as a yellow solid in 83% yield.

¹H NMR (CD₃OD, 400 MHz): 8.84 (s, 1H), 8.83~8.82 (d, J=2.0 Hz, 1H), 8.60~8.57 (dd, J=2.0 Hz, 9.6 Hz, 1H), 7.98~7.96 (d, J=9.2 Hz, 1H), 7.95 (s, 1H), 7.81~7.79 (dd, J=1.6 Hz, 7.2 Hz, 1H), 7.52~7.49 (m, 2H), 7.17~7.16 (d, J=2.8 Hz, 1H), 6.82~6.81 (d, J=2.8 Hz, 1H), 3.64 (s, 1H), 3.38 (s, 3H); MS (m/e): 342.3 (M+1).

Example 127

Synthesis of 1-(4-(3-ethynylphenylamino)quinazolin-6-yl)-1H-imidazol-2 (3H)-one

Compound 127 was prepared in a manner similar to that described in Example 126.

¹H NMR (CD3OD, 400 MHz): 8.55 (s, 2H), 8.24~8.22 (dd, J=2.8 Hz, 9.2 Hz, 1H), 7.97 (s, 1H), 7.88~7.86 (d, J=8.8 Hz, 1H), 7.82-7.81 (d, J=2.4 Hz, 1H), 7.40~7.36 (t, J=8.0 Hz, 1H), 7.28~7.26 (d, J=8.8 Hz, 1H), 7.09~7.08 (d, J=3.2 Hz, 1H), 6.79~6.78 (d, J=3.2 Hz, 1H), 3.52 (s, 1H); MS (m/e): 327.9 (M+1).

Example 128

Synthesis of 1-(4-(3-ethynylphenylamino)quinazolin-6-yl)-3-(2-methoxy-ethyl)-1H-imidazol-2(3H)-one (Compound 128)

The synthetic route to Compound 128 is shown below:

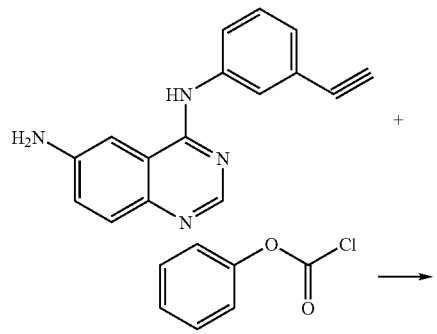

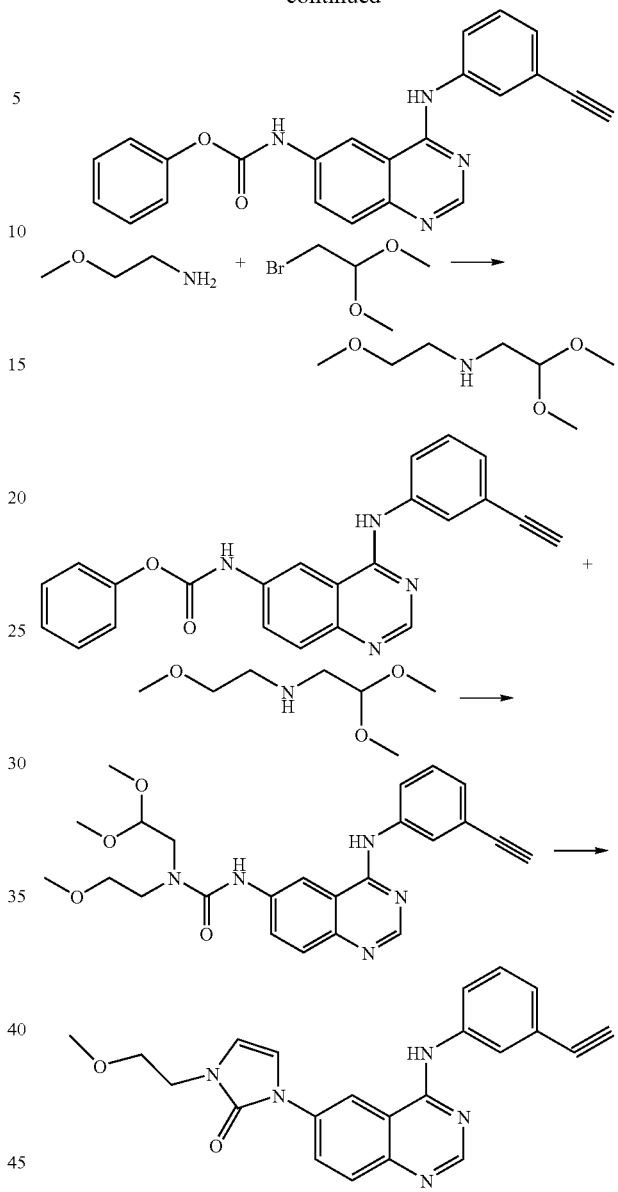

To a solution of N4-(3-ethynylphenyl)quinazoline-4,6-diamine (100 mg, 0.38 mmol) in DMF (2 mL) containing pyridine (37 μL, 0.46 mmol) was added phenyl chloroformate (49 μL, 0.38 mmol) dropwise at room temperature for 1 h. The reaction mixture was diluted with ethyl acetate and washed with water and brine. The combined organic layers were concentrated to give phenyl 4-(3-ethynylphenylamino)quinazolin-6-ylcarbamate as a yellow solid in 95% yield and used in the next step without purification.

To a solution of 2-methoxyethanamine (100 mg, 1.33 mmol) in DMF (2 mL) was added K₂CO₃ (276 mg, 1.99 mmol) and 2-bromo-1,1-dimethoxyethane (236 mg, 1.39 mmol). The mixture was stirred at 80° C. for 3 h. After cooled to room temperature, the reaction mixture was diluted with ethyl acetate and washed with water and brine. The organic layer was concentrated to give 2,2-dimethoxy-N-(2-methoxyethyl)ethanamine as a yellow oil in 91% yield and used in the next step without purification.

To a solution of phenyl 4-(3-ethynylphenylamino)quinazolin-6-ylcarbamate (50 mg, 0.13 mmol) in DMF (2 mL) was added 2,2-dimethoxy-N-(2-methoxyethyl)ethanamine (22.0 mg, 0.13 mmol). The mixture was stirred at 80° C. for 0.5 h and then p-toluenesulfonic acid (28.5 mg, 0.15 mmol) was added. After stirred at 80° C. for additional 1 h, the mixture was cooled to room temperature and diluted with ethyl acetate and washed with water and brine. The organic layer was concentrated and purified with silica column to give Compound 128 as yellow solid in 82% yield.

$^1$H NMR (CD$_3$OD, 400 MHz): 8.57 (s, 2H), 8.24~8.22 (dd, J=2.8 Hz, 9.2 Hz, 1H), 7.98 (s, 1H), 7.89~7.87 (d, J=8.8 Hz, 1H), 7.82~7.81 (d, J=2.4 Hz, 1H), 7.40~7.36 (t, J=8.0 Hz, 1H), 7.29~7.27 (d, J=8.8 Hz, 1H), 7.09~7.08 (d, J=3.2 Hz, 1H), 7.40~7.36 (d, J=3.2 Hz, 1H), 3.92~3.90 (t, J=5.2 Hz, 2H), 3.68~3.66 (t, J=5.2 Hz, 2H), 3.52 (s, 1H), 3.40 (s, 3H); MS (m/e): 386.4 (M+1).

Examples 129-156

Synthesis of Compounds 129-156

Compounds 129-156 were prepared in a manner similar to that described in Example 128.

Compound 129:
$^1$H NMR (DMSO-d6, 400 MHz): 10.06 (s, 1H), 8.71 (s, 1H), 8.7-0 (s, 1H), 8.51~8.48 (dd, J=1.6 Hz, 8.4 Hz, 1H), 8.09 (s, 1H), 7.99~7.97 (d, J=8.0 Hz, 1H), 7.89-7.87 (d, J=8.8 Hz, 1H), 7.45~7.41 (t, J=8.0 Hz, 1H), 7.34~7.33 (d, J=3.2 Hz, 1H), 7.26~7.24 (d, J=7.2 Hz, 1H), 6.93~6.92 (d, J=3.2 Hz, 1H), 4.23 (s, 1H), 3.77~3.74 (t, J=6.4 Hz, 2H), 3.61~3.55 (m, 4H), 2.61~2.56 (t, J=6.4 Hz, 2H), 2.48~2.24 (m, 4H); MS (m/e): 441.5 (M+1).

Compound 130:
$^1$H NMR (DMSO-d6, 400 MHz): 10.04 (s, 1H), 8.69 (s, 1H), 8.63 (s, 1H), 8.49~8.46 (dd, J=1.6 Hz, 8.4 Hz, 1H), 8.08 (s, 1H), 7.99~7.97 (d, J=8.0 Hz, 1H), 7.89-7.87 (d, J=8.8 Hz, 1H), 7.45~7.41 (t, J=8.0 Hz, 1H), 7.34~7.33 (d, J=3.2 Hz, 1H), 7.26~7.24 (d, J=7.2 Hz, 1H), 6.96~6.95 (d, J=3.2 Hz, 1H), 4.23 (s, 1H), 3.86~3.83 (t, J=6.8 Hz, 2H), 2.84~2.80 (t, J=6.8 Hz, 2H), 2.12 (s, 3H); MS (m/e): 402.5 (M+1).

Compound 131:
$^1$H NMR (DMSO-d6, 400 MHz): 9.74 (s, 1H), 8.67 (s, 1H), 8.63 (s, 1H), 8.45~8.43 (dd, J=2.4 Hz, 8.8 Hz, 1H), 8.07 (s, 1H), 7.97~7.95 (d, J=8.0 Hz, 1H), 7.89-7.87 (d, J=8.8 Hz, 1H), 7.45~7.41 (t, J=8.0 Hz, 1H), 7.31~7.30 (d, J=3.2 Hz, 1H), 7.26~7.24 (d, J=7.2 Hz, 1H), 7.08~7.07 (d, J=3.2 Hz, 1H), 4.23 (s, 1H), 4.14~4.10 (m, 1H), 3.99~3.96 (m, 2H), 3.50~3.45 (t, J=8.4 Hz, 2H), 1.91~1.86 (m, 2H), 1.79~1.75 (m, 2H); MS (m/e): 412.4 (M+1).

Compound 132:
$^1$H NMR (DMSO-d6, 400 MHz): 9.74 (s, 1H), 8.67 (s, 1H), 8.63 (s, 1H), 8.45~8.43 (dd, J=2.4 Hz, 8.8 Hz, 1H), 8.07 (s, 1H), 7.97~7.95 (d, J=8.0 Hz, 1H), 7.89-7.87 (d, J=8.8 Hz, 1H), 7.45~7.41 (t, J=8.0 Hz, 1H), 7.31~7.30 (d, J=3.2 Hz, 1H), 7.26~7.24 (d, J=7.2 Hz, 1H), 7.08~7.07 (d, J=3.2 Hz, 1H), 4.23 (s, 1H), 3.98~3.97 (m, 1H), 3.25~3.24 (m, 2H), 3.03~2.99 (m, 2H), 2.29 (s, 3H), 1.95~1.80 (m, 4H); MS (m/e): 425.2 (M+1).

Compound 133:
$^1$H NMR (DMSO-d6, 400 MHz): 9.93 (s, 1H), 8.63 (s, 2H), 8.46~8.43 (dd, J=2.8 Hz, 8.8 Hz, 1H), 8.06 (s, 1H), 7.96~7.94 (d, J=8.4 Hz, 2H), 7.45~7.41 (t, J=8.0 Hz, 1H), 7.26~7.24 (m, 2H), 6.93 (s, 1H), 4.24 (s, 1H), 3.65~3.62 (t, J=6.8 Hz, 2H), 1.67~1.64 (m, 2H), 1.35~1.24 (m, 2H), 0.95~0.91 (t, J=7.2 Hz, 3H); MS (m/e): 384.4 (M+1).

Compound 134:
MS (m/e): 466.5 (M+1).

Compound 135:
$^1$H NMR (CD3OD, 400 MHz): 8.79 (s, 1H), 8.62 (s, 1H), 8.55~8.33 (d, J=8.8 Hz, 1H), 8.13 (s, 1H), 8.04~8.02 (d, J=8.0 Hz, 1H), 7.88~7.85 (d, J=8.0 Hz, 1H), 7.46~7.40 (m, 2H), 6.91~6.90 (d, J=3.2 Hz, 1H), 4.23 (s, 1H), 3.74~3.71 (t, J=6.4 Hz, 2H), 2.57~2.54 (t, J=6.4 Hz, 2H), 2.27 (s, 6H); MS (m/e): 399.4 (M+1).

Compound 136:
$^1$H NMR (DMSO-d6, 400 MHz): 10.41 (s, 1H), 8.84 (s, 1H), 8.62 (s, 1H), 8.06 (s, 1H), 8.57~8.54 (dd, J=2.4 Hz, 8.8 Hz, 1H), 8.17 (s, 1H), 8.07~8.05 (d, J=8.8 Hz, 1H), 7.87~7.85 (d, J=9.2 Hz, 1H), 7.58~7.57 (d, J=3.6 Hz, 1H), 7.42~7.39 (t, J=8.0 Hz, 1H), 7.24~7.18 (m, 2H), 6.90 (s, 1H), 6.61 (d, J=3.2 Hz, 1H), 4.35~4.32 (t, J=6.0 Hz, 2H), 4.24 (s, 1H), 4.02~3.99 (t, J=6.0 Hz, 2H); MS (m/e): 422.5 (M+1).

Compound 137:
$^1$H NMR (CD3OD, 400 MHz): 8.66~8.53 (m, 4H), 8.27~8.24 (dd, J=2.0 Hz, 9.2 Hz, 1H), 7.91~7.79 (m, 4H), 7.50 (m, 1H), 7.43~7.39 (t, J=8.0 Hz, 1H), 7.31~7.29 (d, J=7.6 Hz, 1H), 7.18~7.17 (d, J=3.2 Hz, 1H), 6.90~6.89 (d, J=3.2 Hz, 1H), 5.02 (s, 2H), 3.38 (s, 1H); MS (m/e): 419.5 (M+1).

Compound 138:
$^1$H NMR (DMSO-d6, 400 MHz): 9.96 (s, 1H), 8.66 (s, 1H), 8.63 (s, 1H), 8.45~8.43 (d, J=8.4 Hz, 1H), 8.05 (s, 1H), 7.95~7.87 (m, 2H), 7.45~6.99 (m, 8H), 6.99 (s, 1H), 6.61 (d, J=3.2 Hz, 1H), 4.88 (s, 2H), 4.24 (s, 1H); MS (m/e): 436.5 (M+1).

Compound 139:
$^1$H NMR (DMSO-d6, 400 MHz): 10.04 (s, 1H), 8.68 (s, 1H), 8.62 (s, 1H), 8.46~8.44 (d, J=9.2 Hz, 1H), 8.07 (s, 1H), 7.97~7.95 (d, J=7.6 Hz, 1H), 7.88-7.86 (d, J=9.2 Hz, 1H), 7.44~7.40 (t, J=8.0 Hz, 1H), 7.28 (s, 1H), 7.25~7.23 (d, J=7.2 Hz, 1H), 6.81 (s, 1H), 4.24 (s, 1H), 3.07 (s, 1H), 0.90 (bs, 4H); MS (m/e): 368.4 (M+1).

Compound 140:
$^1$H NMR (CD3OD, 400 MHz): 8.60 (s, 1H), 8.58~8.57 (d, J=2.4 Hz, 1H), 8.25~8.22 (dd, J=2.0 Hz, 9.2 Hz, 1H), 8.01 (s, 1H), 7.90~7.88 (d, J=9.2 Hz, 1H), 7.86-7.84 (d, J=8.4 Hz, 1H), 7.43~7.39 (t, J=8.0 Hz, 1H), 7.31~7.29 (d, J=7.6 Hz, 1H), 7.12 (s, 1H), 6.86 (s, 1H), 4.59~4.57 (m, 1H), 3.56 (s, 1H), 2.16~2.12 (m, 2H), 1.92~1.76 (m, 6H); MS (m/e): 396.4 (M+1).

Compound 141:
$^1$H NMR (DMSO-d6, 400 MHz): 9.92 (s, 1H), 8.63 (s, 2H), 8.42~8.39 (dd, J=2.4 Hz, 9.2 Hz, 1H), 8.01 (s, 1H), 7.95~7.93 (d, J=9.2 Hz, 1H), 7.88~7.86 (d, J=9.2 Hz, 1H), 7.44~7.40 (t, J=8.0 Hz, 1H), 7.25~7.23 (m, 2H), 7.03 (s, 1H), 4.23 (s, 1H), 4.10 (bs, 1H), 3.04 (s, 2H), 1.88 (bs, 8H), 1.03 (bs, 3H); MS (m/e): 439.4 (M+1).

Compound 142:
$^1$H NMR (CD3OD, 400 MHz): 9.88 (s, 1H), 8.64 (s, 1H), 8.61 (s, 1H), 8.42~8.40 (d, J=8.8 Hz, 1H), 8.04 (s, 1H), 7.93~7.88 (m, 2H), 7.50~7.49 (d, J=4.8 Hz, 1H), 7.45~7.41 (t, J=7.6 Hz, 1H), 7.26~7.24 (d, J=7.6 Hz, 1H), 7.23~7.22 (d, J=2.8 Hz, 1H), 7.15 (s, 1H), 7.04~7.02 (t, J=4.0 Hz, 1H), 6.97~6.96 (d, J=2.8 Hz, 1H), 5.04 (s, 2H), 4.24 (s, 1H); MS (m/e): 424.5 (M+1).

Compound 143:
$^1$H NMR (DMSO-d6, 400 MHz): 9.93 (s, 1H), 8.64 (s, 1H), 8.63 (s, 1H), 8.44~8.42 (dd, J=2.0 Hz, 8.8 Hz, 1H), 8.05 (s, 1H), 7.95~7.93 (d, J=8.4 Hz, 1H), 7.90~7.88 (d, J=8.8 Hz, 1H), 7.45~7.43 (t, J=8.0 Hz, 1H), 7.27~7.25 (m, 2H), 6.86~6.85 (d, J=3.2 Hz, 1H), 6.00~5.93 (m, 1H), 5.24~5.16 (m, 2H), 4.29~4.27 (d, J=5.2 Hz, 2H), 4.24 (s, 1H); MS (m/e): 368.4 (M+1).

Compound 144:

¹H NMR (DMSO-d6, 400 MHz): 9.89 (s, 1H), 8.62 (bs, 2H), 8.42 (bs, 1H), 8.05 (s, 1H), 7.91~7.80 (m, 2H), 7.44 (bs, 1H), 7.25~7.14 (m, 2H), 6.99 (s, 1H), 4.25 (s, 1H), 3.61 (bs, 2H), 3.26 (bs, 2H), 3.04~2.90 (m, 2H), 2.08 (bs, 2H), 1.93~1.88 (m, 4H); MS (m/e): 453.5 (M+1).

Compound 145:

¹H NMR (CD3OD, 400 MHz): 9.91 (s, 1H), 8.64 (s, 1H), 8.63~8.62 (d, J=2.0 Hz, 1H), 8.39~8.36 (dd, J=1.6 Hz, 9.2 Hz, 1H), 8.04 (s, 1H), 7.93~7.89 (m, 2H), 7.46~7.42 (t, J=8.0 Hz, 1H), 7.27 (s, 1H), 7.25~7.24 (d, J=3.2 Hz, 1H), 6.97~6.96 (d, J=3.2 Hz, 1H), 4.52~4.51 (d, J=2.0 Hz, 2H), 4.25 (s, 1H), 3.44 (s, 1H); MS (m/e): 366.4 (M+1).

Compound 146:

¹H NMR (CD3OD, 400 MHz): 9.88 (s, 1H), 8.63 (s, 1H), 8.60 (s, 1H), 8.43~8.41 (d, J=8.8 Hz, 1H), 8.03 (s, 1H), 7.93~7.87 (m, 2H), 7.46~7.42 (t, J=7.6 Hz, 1H), 7.26~7.24 (d, J=8.0 Hz, 1H), 7.21~7.20 (d, J=3.2 Hz, 1H), 6.94~6.93 (d, J=2.8 Hz, 1H), 4.25 (s, 1H), 3.66~3.63 (t, J=6.8 Hz, 2H), 2.48~2.39 (m, 6H), 1.79~1.76 (m, 2H), 0.96~0.93 (t, J=7.2 Hz, 6 Hz); MS (m/e): 441.5 (M+1).

Compound 147:

¹H NMR (DMSO-d6, 400 MHz): 10.11 (s, 1H), 8.72 (d, J=2.0 Hz, 1H), 8.63 (s, 1H), 8.59 (dd, J=2.0 Hz, J=2.0 Hz, 1H), 8.10 (s, 1H), 7.99 (d, J=8.0 Hz, 1H), 7.88 (d, J=9.2 Hz, 1H), 7.43 (t, J=8.0 Hz, 1H), 7.35 (d, J=2.8 Hz, 1H), 7.24 (d, J=7.6 Hz, 1H), 6.88 (d, J=2.8 Hz, 1H), 4.23 (s, 1H), 3.80-3.78 (m, 2H), 3.65-3.62 (m, 2H), 3.51-3.48 (m, 2H), 1.14-1.08 (m, 3H); MS (m/e): 400 (M+1).

Compound 148:

¹H NMR (CD₃OD, 400 MHz): 9.88 (s, 1H), 8.62 (s, 1H), 8.60 (s, 1H), 8.03 (s, 1H), 7.93~7.91 (d, J=8.0 Hz, 1H), 7.89~7.87 (d, J=9.2 Hz, 1H), 7.45~7.43 (t, J=8.0 Hz, 1H), 7.26~7.24 (d, J=7.2 Hz, 1H), 7.18~7.17 (d, J=3.2 Hz, 1H), 6.91~6.90 (d, J=2.8 Hz, 1H), 4.23 (s, 1H), 3.75~3.72 (t, J=6.4 Hz, 2H), 2.59~2.56 (t, J=6.4 Hz, 2H), 2.51~2.40 (m, 4H), 2.38~2.32 (m, 4H), 2.14 (s, 3H); MS (m/e): 454.5 (M+1).

Compound 149:

¹H NMR (CD₃OD, 400 MHz): 9.92 (s, 1H), 8.63 (s, 1H), 8.60 (s, 1H), 8.44~8.42 (d, J=8.8 Hz, 1H), 8.04 (s, 1H), 7.96~7.87 (m, 2H), 7.46~7.42 (t, J=7.6 Hz, 1H), 7.26~7.24 (d, J=7.6 Hz, 1H), 7.18~7.17 (d, J=2.8 Hz, 1H), 6.91~6.90 (d, J=2.4 Hz, 1H), 4.25 (s, 1H), 3.37~3.69 (m, 1H), 3.52~3.47 (m, 1H), 2.30~2.26 (m, 2H), 2.19~2.06 (m, 2H), 1.78~1.71 (m, 2H), 1.65~1.59 (m, 2H), 1.42~1.45 (m, 1H), 1.07~1.10 (m, 3H); MS (m/e): 439.5 (M+1).

Compound 150:

¹H NMR (CD₃OD, 400 MHz): 8.57 (s, 1H), 8.53 (s, 1H), 8.22~8.20 (dd, J=1.6 Hz, 9.2 Hz, 1H), 7.99 (s, 1H), 7.89~7.87 (d, J=8.8 Hz, 1H), 7.84~7.82 (d, J=8.0 Hz, 1H), 7.39~7.37 (t, J=7.6 Hz, 1H), 7.29~7.27 (d, J=7.2 Hz, 1H), 7.03~7.02 (d, J=2.8 Hz, 1H), 6.82~6.81 (d, J=3.2 Hz, 1H), 4.16~4.12 (t, J=6.8 Hz, 2H), 3.56 (s, 1H), 2.59~2.56 (t, J=6.4 Hz, 2H); MS (m/e): 400.4 (M+1).

Compound 151:

¹H NMR (CD₃OD, 400 MHz): 8.58~8.57 (m, 2H), 8.25~8.22 (dd, J=2.0 Hz, 8.8 Hz, 1H), 7.98 (s, 1H), 7.92~7.89 (d, J=8.8 Hz, 1H), 7.86~7.84 (d, J=8.0 Hz, 1H), 7.43~7.39 (t, J=7.6 Hz, 1H), 7.31~7.29 (d, J=7.2 Hz, 1H), 7.09~7.08 (d, J=2.8 Hz, 1H), 6.80~6.79 (d, J=3.2 Hz, 1H), 3.86~3.83 (t, J=6.4 Hz, 2H), 3.53 (s, 1H), 2.91~2.88 (t, J=6.8 Hz, 2H), 2.26~2.22 (m, 2H), 1.85~1.66 (m, 5H); MS (m/e): 425.1 (M+1).

Compound 152:

¹H NMR (CD₃OD, 400 MHz): 8.61 (s, 1H), 8.53 (s, 1H), 8.22~8.20 (dd, J=1.6 Hz, 9.2 Hz, 1H), 7.99 (s, 1H), 7.89~7.87 (d, J=8.8 Hz, 1H), 7.84~7.82 (d, J=8.0 Hz, 1H), 7.39~7.37 (t, J=7.6 Hz, 1H), 7.29~7.27 (d, J=7.2 Hz, 1H), 7.03~7.02 (d, J=2.8 Hz, 1H), 6.83~6.82 (d, J=2.8 Hz, 1H), 4.08~4.05 (t, J=6.8 Hz, 2H), 3.55 (s, 1H), 3.52~3.40 (m, 4H), 2.85~2.82 (t, J=6.8 Hz, 2H), 2.00~1.89 (m, 4H); MS (m/e): 453.4 (M+1).

Compound 153:

¹H NMR (CD₃OD, 400 MHz): 8.59 (s, 1H), 8.57~8.56 (d, J=2.0 Hz, 1H), 8.24~8.21 (dd, J=2.4 Hz, 8.8 Hz, 1H), 7.99 (s, 1H), 7.90~7.88 (d, J=8.8 Hz, 1H), 7.84~7.82 (d, J=7.2 Hz, 1H), 7.42~7.38 (t, J=8.0 Hz, 1H), 7.30~7.28 (d, J=7.6 Hz, 1H), 7.10~7.09 (d, J=3.2 Hz, 1H), 6.81~6.80 (d, J=3.6 Hz, 1H), 3.90~3.87 (t, J=5.6 Hz, 2H), 3.54 (s, 1H), 3.45~3.42 (t, J=6.0 Hz, 2H), 2.94 (s, 3H); MS (m/e): 449.5 (M+1).

Compound 154:

¹H NMR (CD₃OD, 400 MHz): 8.58 (s, 1H), 8.56~8.55 (d, J=2.0 Hz, 1H), 8.23~8.20 (dd, J=2.4 Hz, 8.8 Hz, 1H), 7.99 (s, 1H), 7.89~7.87 (d, J=8.8 Hz, 1H), 7.84~7.82 (d, J=8.0 Hz, 1H), 7.41~7.37 (t, J=8.0 Hz, 1H), 7.29~7.27 (d, J=7.6 Hz, 1H), 7.08~7.07 (d, J=2.8 Hz, 1H), 6.80~6.79 (d, J=3.6 Hz, 1H), 3.96~3.93 (t, J=5.6 Hz, 2H), 3.53 (s, 1H), 3.52~3.48 (t, J=5.6 Hz, 2H), 2.94 (s, 3H), 2.84 (s, 3H); MS (m/e): 463.5 (M+1).

Compound 155:

¹H NMR (CD₃OD, 400 MHz): 8.58 (s, 1H), 8.56~8.55 (d, J=2.0 Hz, 1H), 8.23~8.20 (dd, J=2.0 Hz, 8.8 Hz, 1H), 7.98 (s, 1H), 7.89~7.87 (d, J=9.2 Hz, 1H), 7.84~7.82 (d, J=8.0 Hz, 1H), 7.41~7.37 (t, J=7.6 Hz, 1H), 7.29~7.27 (d, J=8.0 Hz, 1H), 7.07~7.06 (d, J=2.8 Hz, 1H), 6.73~6.72 (d, J=2.8 Hz, 1H), 3.85~3.82 (t, J=5.6 Hz, 2H), 3.55~3.52 (t, J=6.0 Hz, 2H), 3.52 (s, 1H), 1.56~1.52 (m, 1H), 0.83~0.81 (m, 2H), 074~0.71 (m, 2H); MS (m/e): 439.5 (M+1).

Compound 156:

¹H NMR (CD₃OD, 400 MHz): 8.61 (d, J=2.0 Hz, 1H), 8.60~8.56 (dd, J=2.0 Hz, 1H), 8.24~8.21 (dd, J=2.0 Hz, 9.2 Hz, 1H), 8.01~7.99 (dd, J=2.0 Hz, 4.4 Hz, 1H), 7.92~7.91 (dd, J=2.4 Hz, 9.2 Hz, 1H), 7.86~7.84 (d, J=8.0 Hz, 1H), 7.43~7.39 (t, J=8.0 Hz, 1H), 7.32~7.30 (d, J=8.0 Hz, 1H), 4.05~4.02 (t, J=5.6 Hz, 1H), 3.98~3.96 (t, J=5.6 Hz, 1H), 3.94~3.92 (t, J=5.6 Hz, 1H), 3.78~3.75 (t, J=5.6 Hz, 1H), 3.55 (s, 1H), 3.27 (s, 1.5H), 3.05 (s, 1.5H), 1.92~1.85 (m, 1H), 0.82~0.77 (m, 3H), 0.69~0.65 (m, 1H); MS (m/e): 453.5 (M+1).

Example 157

Synthesis of 3-(2-(dimethylamino)ethyl)-1-(4-(3-ethynylphenylamino)quinazolin-7-yl)-1H-imidazol-2(3H)-one (Compound 157)

The Synthetic route to Compound 157 is shown below:

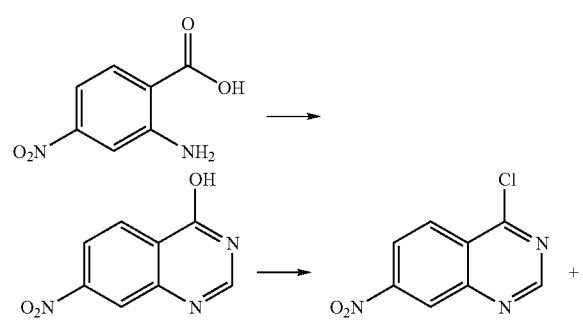

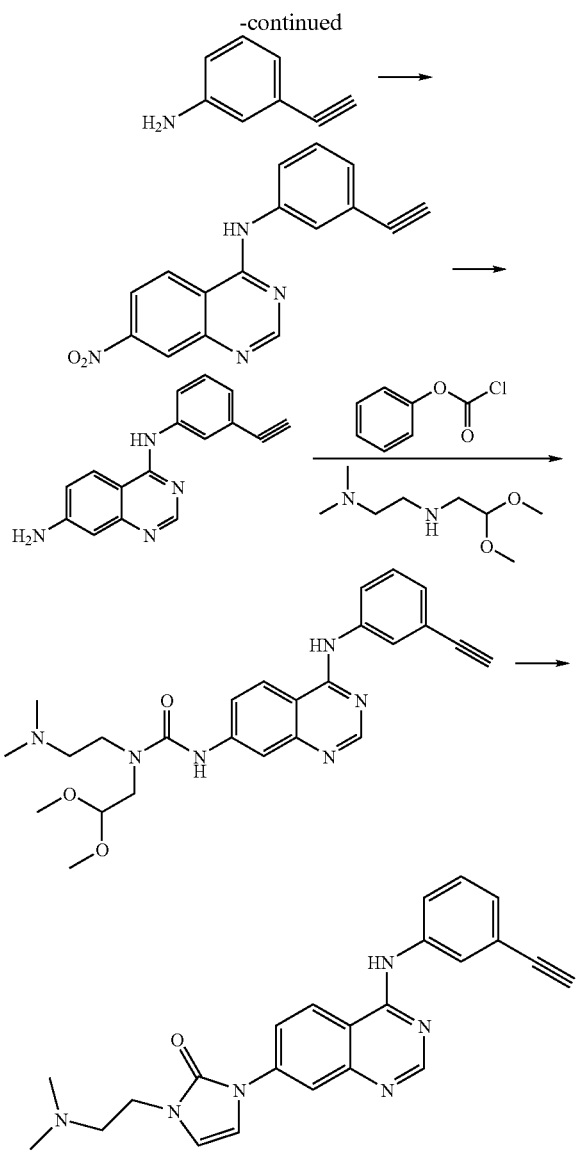

To a solution of 2-amino-4-nitrobenzoic acid (6.00 g, 32.94 mmol) in ethanol (40 mL) was added formamidin acetate (6.80 g, 65.32 mmol). The reaction mixture was refluxed for 5 h and cooled to room temperature and refrigerated. The precipitate was filtered out, washed with several portions of cooled ethanol, and then dried in vacuo to give 5.60 g (89%) of 7-nitroquinazolin-4-ol as a yellow solid.

A mixture of 7-nitroquinazolin-4-ol (3.4 g, 17.79 mmol), thionyl chloride (20 mL), and DMF (0.5 mL) was refluxed for 48 h. After the mixture was cooled to room temperature, excess thionyl chloride was removed by evaporation and the residue was azeotroped with toluene to afford 2.61 g (70%) of product 4-chloro-7-nitroquinazoline as a yellowish solid.

A mixture of 4-chloro-7-nitroquinazoline (2.0 g, 9.54 mmol), isopropanol (30 mL), and 3-thynylbenzenamine (1.2 g, 10.00 mmol) was refluxed for 5 h. The resulting mixture was cooled to room temperature and refrigerated. The precipitate was filtered out, washed with cold isopropanol several times, and dried in vacuo to give 2.6 g (94%) of N-(3-ethynylphenyl)-7-nitroquinazolin-4-amine as a yellow solid.

N-(3-ethynylphenyl)-7-nitroquinazolin-4-amine (2.0 g, 6.89 mmol), SnCl$_2$ (5.0 g, 26.37 mmol), and ethyl acetate (50 mL) was refluxed for 3 h. The mixture was subjected to extraction with ethyl acetate (20 mL). The combined organic layers were washed with brine (20 mL×2), dried over Na$_2$SO$_4$, and concentrated in vacuo to afford 1.6 g (86%) of N4-(3-ethynylphenyl)quinazoline-4,7-diamine as a yellow solid.

A mixture of N4-(3-ethynylphenyl)quinazoline-4,7-diamine (48 mg, 0.18 mmol), phenyl carbonochloridate (25.2 uL, 0.18 mmol), pyridine (32 μL), and DMF (2 mL) was stirred at room temperature for 1.5 h. To this was added N1-(2,2-dimethoxyethyl)-N2,N2-dimethylethane-1,2-diamine (33.5 mg, 0.19 mmol). The mixture was stirred at 80° C. for 1 h and then p-toluenesulfonic acid (35.6 mg, 0.20 mmol) was added. The mixture was stirred at 80° C. for additional 1 h. After cooled to room temperature, it was diluted with ethyl acetate and washed with water and brine. The combined organic layers were concentrated and purified with silica column to give Compound 157 as a yellow solid in 75% yield.

$^1$H NMR (CD$_3$OD, 400 MHz): 8.57 (s, 1H), 8.48~8.47 (d, J=3.6 Hz, 1H), 8.46 (s, 1H), 8.09 (s, 1H), 8.07 (s, 1H), 7.98 (s, 1H), 7.83~7.81 (d, J=8.0 Hz, 1H), 7.42~7.38 (t, J=8.0 Hz, 1H), 7.31~7.29 (d, J=7.6 Hz, 1H), 7.13~7.12 (d, J=2.8 Hz, 1H), 6.83~6.82 (d, J=2.8 Hz, 1H), 3.89~3.85 (t, J=6.8 Hz, 2H), 3.56 (s, 1H), 2.72~2.69 (t, J=6.4 Hz, 2H), 2.35 (s, 6H); MS (m/e): 399.4 (M+1).

Examples 158-163

Synthesis of Compounds 158-163

Compounds 158-163 were prepared in a manner similar to that described in Example 157.

Compound 158:
$^1$H NMR (CD$_3$OD, 400 MHz): 8.59 (s, 1H), 8.52~8.49 (d, J=8.8 Hz, 1H), 8.11~8.08 (d, J=2.4 Hz, 1H), 8.09~8.08 (d, J=2.4 Hz, 1H), 7.98 (s, 1H), 7.83~7.81 (d, J=8.0 Hz, 1H), 7.43~7.39 (t, J=7.6 Hz, 1H), 7.32~7.30 (d, J=7.6 Hz, 1H), 7.18~7.17 (d, J=2.8 Hz, 1H), 6.85~6.84 (d, J=3.2 Hz, 1H), 3.81~3.77 (t, J=6.8 Hz, 2H), 3.56 (s, 1H), 2.74~2.67 (m, 6H), 2.02~1.95 (m, 2H), 1.14~1.10 (t, J=7.2 Hz, 6H); MS (m/e): 441.5 (M+1).

Compound 159:
$^1$H NMR (MeOD, 400 MHz): 8.58 (s, 1H), 8.48~8.45 (dd, J=1.6 Hz, 8.0 Hz, 1H), 8.09~8.08 (d, J=2.4 Hz, 1H), 8.07 (s, 1H), 7.98 (s, 1H), 7.83~7.81 (d, J=8.0 Hz, 1H), 7.42~7.38 (t, J=8.0 Hz, 1H), 7.31~7.29 (d, J=7.2 Hz, 1H), 7.12~7.11 (d, J=2.8 Hz, 1H), 6.84~6.83 (d, J=3.2 Hz, 1H), 3.90~3.85 (m, 1H), 3.67~3.64 (m, 1H), 3.55 (s, 1H), 3.23~3.18 (m, 1H), 3.01~2.94 (m, 1H), 2.86~2.82 (m, 1H), 2.44~2.38 (m, 1H), 2.32~2.26 (m, 1H), 1.98~1.91 (m, 1H), 1.75~1.69 (m, 1H), 1.18 (s, 3H); MS (m/e): 439.5 (M+1H).

Compound 160:
$^1$H NMR (CD$_3$OD, 400 MHz): 8.59 (s, 1H), 8.51~8.49 (dd, J=2.0 Hz, 7.6 Hz, 1H), 8.13~8.12 (d, J=2.0 Hz, 1H), 8.11~8.10 (d, J=2.0 Hz, 1H), 7.98 (s, 1H), 7.83~7.81 (d, J=8.0 Hz, 1H), 7.43~7.39 (t, J=8.4 Hz, 1H), 7.32~7.30 (d, J=8.0 Hz, 1H), 7.16~7.15 (d, J=3.6 Hz, 1H), 6.82~6.81 (d, J=3.2 Hz, 1H), 3.82~3.78 (t, J=7.2 Hz, 2H), 3.61 (s, 1H), 2.73~2.33 (m, 10H), 2.28 (s, 3H), 2.00~1.93 (m, 2H); MS (m/e): 468.5 (M+1).

Compound 161:
$^1$H NMR (CD$_3$OD, 400 MHz): 8.59 (s, 1H), 8.51~8.49 (d, J=9.6 Hz, 1H), 8.11~8.08 (m, 2H), 7.98 (s, 1H), 7.83~7.81 (d, J=8.0 Hz, 1H), 7.43~7.39 (t, J=7.6 Hz, 1H), 7.32~7.30 (dd, J=1.6 Hz, 6.8 Hz, 1H), 7.17~7.16 (d, J=3.2 Hz, 1H), 6.86~6.85 (d, J=2.8 Hz, 1H), 3.85~3.78 (t, J=6.8 Hz, 2H), 3.55 (s, 1H), 3.12~3.07 (m, 1H), 2.38 (s, 3H), 2.30~2.12 (m, 4H), 1.85~1.78 (m, 2H), 1.69~1.55 (m, 2H); MS (m/e): 439.5 (M+1).

Compound 162:

$^1$H NMR (CD$_3$OD, 400 MHz): 8.59 (s, 1H), 8.51~8.48 (d, J=10.0 Hz, 1H), 8.11~8.09 (m, 2H), 7.98 (s, 1H), 7.84~7.81 (d, J=8.8 Hz, 1H), 7.43~7.39 (t, J=8.0 Hz, 1H), 7.32~7.30 (d, J=7.6 Hz, 1H), 7.15~7.14 (d, J=3.2 Hz, 1H), 6.88~6.87 (d, J=2.8 Hz, 1H), 3.77~3.73 (t, J=7.2 Hz, 2H), 3.54 (s, 1H), 3.54~3.50 (t, J=7.2 Hz, 2H), 3.42~3.39 (t, J=7.2 Hz, 1H), 2.44~2.40 (t, J=7.6 Hz, 2H), 2.12~2.07 (m, 2H), 2.04~1.99 (m, 2H); MS (m/e): 453.5 (M+1).

Compound 163:

1H NMR (CD$_3$OD, 400 MHz): 8.60 (s, 1H), 8.53~8.50 (d, J=10.0 Hz, 1H), 8.12~8.10 (m, 2H), 7.99 (s, 1H), 7.84~7.82 (d, J=8.0 Hz, 1H), 7.84~7.82 (d, J=8.0 Hz, 1H), 7.44~7.41 (t, J=7.6 Hz, 1H), 7.33~7.31 (d, J=7.2 Hz, 1H), 7.19~7.18 (d, J=2.8 Hz, 1H), 6.86~6.85 (d, J=3.6 Hz, 1H), 3.94~3.91 (t, J=6.8 Hz, 2H), 3.56 (s, 1H), 3.26~3.23 (m, 2H), 3.03 (s, 3H), 2.30~2.26 (m, 2H); MS (m/e): 448.4 (M+1).

Example 164

Synthesis of 3-(2-(diethylamino)ethyl)-1-(4-(3-ethynylphenylamino)-7-fluoroquinazolin-6-yl)-1H-imidazol-2(3H)-one (Compound 164)

The synthetic route to Compound 164 is shown below:

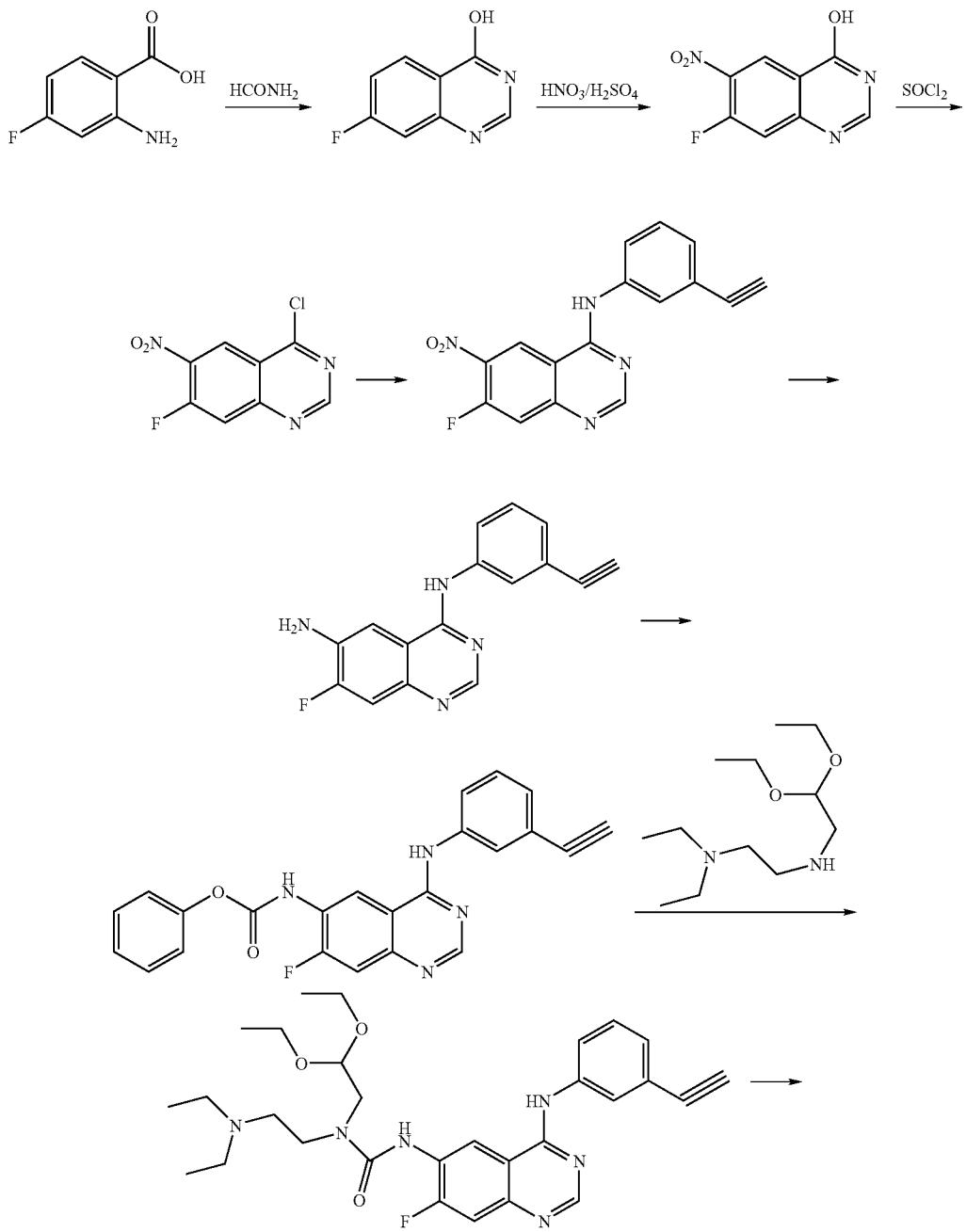

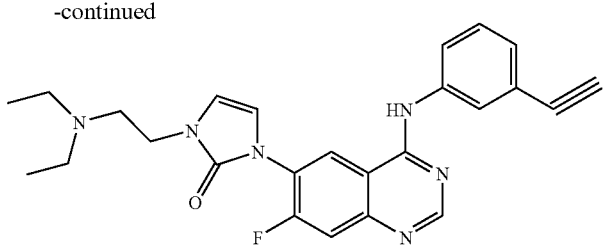

2-amino-4-fluorobenzoic acid (1.55 g, 10 mmol) was dissolved into formamide (5 mL) and stirred at 150° C. for 6 h. The mixture was cooled to room temperature with stirring. The precipitate was filtered out and washed with diethyl ether to give 1.3 g of 7-fluoroquinazolin-4-ol (78%).

7-Fluoroquinazolin-4-ol (1 g, 6.0 mmol) was dissolved in concentrated $H_2SO_4$ (3 mL) at 0° C. Concentrated $HNO_3$ (3 mL) was added dropwise with stirring in 15 min. The mixture was stirred at 100° C. for 3 h and cooled to room temperature. The mixture was poured into ice-water with stirring. The precipitate was filtered and recrystallized in HOAc to give 0.60 g of 7-fluoro-6-nitroquinazolin-4-ol (38%).

7-Fluoro-6-nitroquinazolin-4-ol (518 mg, 2 mmol) was dissolved into thionyl chloride (3 mL) containing 2 drops of DMF. The solution was refluxed for 3 h. The solvent was removed under reduced pressure to afford 4-chloro-7-fluoro-6-nitroquinazoline, which was used directly in the next step without purification.

4-Chloro-7-fluoro-6-nitroquinazolineand 3-ethynylbenzenamine (234 mg, 2 mmol) was dissolved into isopropanol (5 mL). The mixture was refluxed for 3 h and cooled to room temperature. The precipitate was filtered and washed with water to give 0.59 g of N-(3-ethynylphenyl)-7-fluoro-6-nitroquinazolin-4-amine (95%).

A mixture of N-(3-ethynylphenyl)-7-fluoro-6-nitroquinazolin-4-amine (310 mg, 1 mmol) and $SnCl_2.2H_2O$ (171 mg, 4.5 mmol) in ethyl acetate (35 mL) was refluxed for 2 h. After cooled to room temperature, the mixture was treated with 5% aqueous $NaHCO_3$ to adjust its pH to 9-10, and then subjected to extraction with EtOAc. The organic layers were washed with saturated brine and $H_2O$ and dried. The solvent was removed under reduced pressure to give 225 mg (81%) N4-(3-ethynylphenyl)-7-fluoroquinazoline-4,6-diamine as a yellow solid.

N4-(3-ethynylphenyl)-7-fluoroquinazoline-4,6-diamine (50 mg, 0.18 mmol) was dissolved into DMF (2 mL) containing pyridine (17.5 μL, 0.21 mmol). Phenyl chloroformate (23 μL, 0.18 mmol) was added to the mixture at room temperature and stirred at 70° C. for 1 h to give phenyl 4-(3-ethynylphenylamino)-7-fluoroquinazolin-6-ylcarbamate. N1-(2,2-diethoxyethyl)-N2,N2-diethylethane-1,2-diamine (42 mg, 0.18 mmol) was added and stirred at 70° C. for 2.5 h. After cooled to room temperature, the reaction mixture was diluted with ethyl acetate and washed with water. The organic layer was concentrated and purified with a silica column to give 45 mg (70%) of 1-(2,2-diethoxyethyl)-1-(2-(diethylamino)ethyl)-3-(4-(3-ethynylphenylamino)-7-fluoroquinazolin-6-yl)urea.

To a solution of 1-(2,2-diethoxyethyl)-1-(2-(diethylamino)ethyl)-3-(4-(3-ethynylphenylamino)-7-fluoroquinazolin-6-yl)urea (45 mg, 0.08 mmol) in DMF (2 mL) was added p-toluenesulfonic acid (28.5 mg, 0.15 mmol). The mixture was stirred at 80° C. for 1 h and then cooled to room temperature. It was diluted with ethyl acetate and washed with water and brine. The organic layer was concentrated and purified with a silica column to give Compound 164 as yellow solid in 90% yield.

$^1$H NMR (DMSO-d6, 400 MHz): 10.18 (s, 1H), 8.89 (d, J=8.0 Hz, 1H), 8.67 (s, 1H), 8.06 (s, 1H), 7.93 (d, J=7.6 Hz, 1H), 7.65 (d, J=11.2 Hz, 1H), 7.42 (t, J=8.0 Hz, 1H), 7.25 (d, J=7.2 Hz, 1H), 6.88 (s, 1H) 6.87 (d, J=2.8 Hz, 1H), 4.24 (s, 1H), 3.66 (t, J=2.8 Hz, 2H), 2.66 (t, J=6.4 Hz, 2H), 2.49-2.53 (m, 4H), 0.98-0.93 (m, 6H); MS (m/e): 445 (M+1).

Example 165

Synthesis of 3-(2-(diethylamino)ethyl)-1-(4-(3-ethynylphenylamino)-7-methoxyquinazolin-6-yl)-1H-imidazol-2(3H)-one (Compound 165)

The synthetic route to Compound 165 is shown below:

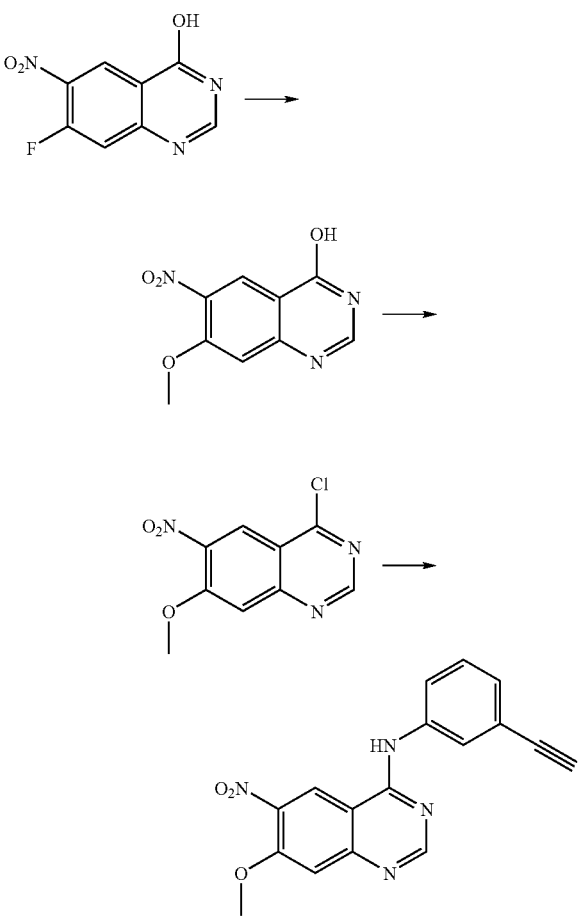

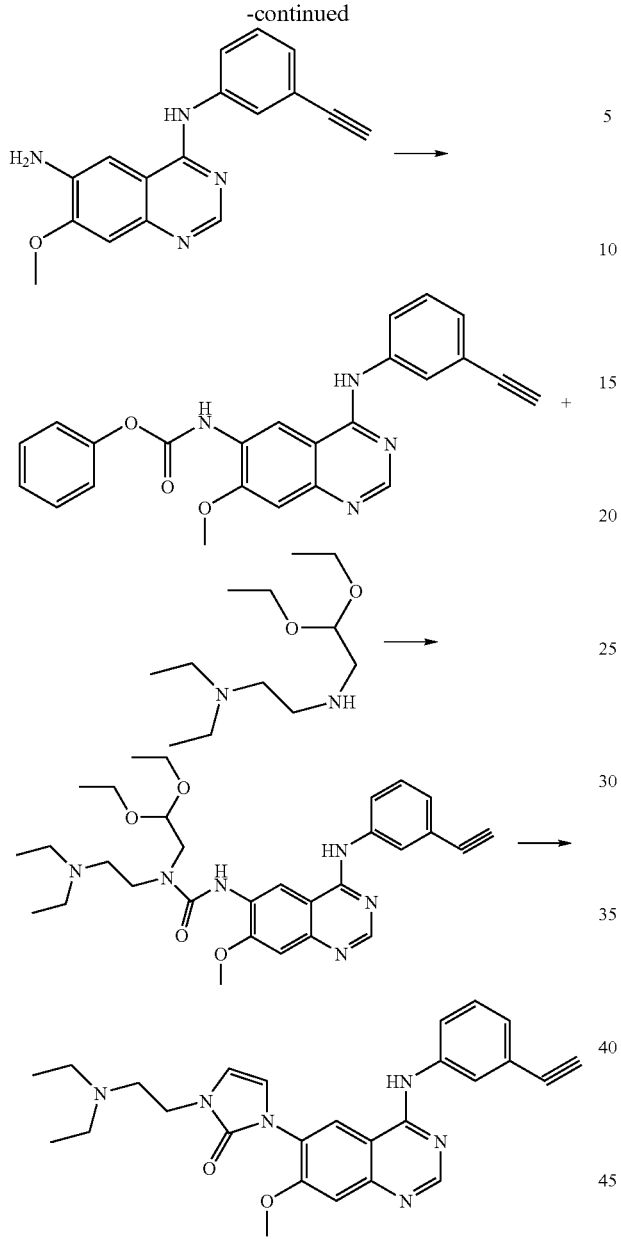

Sodium (92 mg, 4 mmol) was dissolved in methanol (4 mL) under nitrogen at 0° C. 7-Fluoro-6-nitroquinazolin-4-ol (418 mg, 2 mmol) was added. The mixture was refluxed for 3 h and cooled to room temperature and treated with 2N HCl to adjust its pH to 3-4. After the mixture was concentrated, the residue was diluted with ethyl acetate and washed with water twice. The organic layer was concentrated to give 405 mg (92%) of 7-methoxy-6-nitroquinazolin-4-ol.

7-Methoxy-6-nitroquinazolin-4-ol was converted to Compound 165 in a manner similar to that described in Example 160.

$^1$H NMR (DMSO-d6, 400 MHz): 9.98 (s, 1H), 8.69 (s, 1H), 8.63 (s, 1H), 8.05 (s, 1H), 7.92 (d, J=7.2 Hz, 1H), 7.35-7.29 (m, 2H), 7.21 (d, J=7.6 Hz, 1H), 6.75 (d, J=2.0 Hz, 1H), 6.58 (d, J=2.8 Hz, 1H), 4.15 (s, 1H), 3.91 (s, 3H), 3.64 (t, J=7.6 Hz, 2H), 2.65 (t, J=7.2 Hz, 2H), 2.58 (m, 4H), 0.97 (m, 6H); MS (m/e): 457 (M+1).

Examples 166-170

Synthesis of Compounds 166-170

Compounds 166-170 were prepared in a manner similar to that described in Example 165.

Compound 166:
$^1$H NMR (DMSO-d6, 400 MHz): 9.90 (s, 1H), 8.67 (s, 1H), 8.62 (s, 1H), 8.08 (s, 1H), 7.92 (d, J=8.4 Hz, 1H), 7.42-7.37 (m, 2H), 7.21 (d, J=7.6 Hz, 1H), 6.72 (s, 2H), 4.22 (s, 1H), 3.95 (s, 3H), 3.77 (t, J=2.8 Hz, 2H), 3.59 (t, J=4.8 Hz, 2H), 3.31 (s, 3H); MS (m/e): 416 (M+1).

Compound 167:
$^1$H NMR (DMSO-d6, 400 MHz): 9.94 (s, 1H), 8.69 (s, 1H), 8.62 (s, 1H), 8.09 (s, 1H), 7.93 (d, J=7.6 Hz, 1H), 7.42-7.37 (m, 2H), 7.21 (d, J=7.6 Hz, 1H), 6.79 (d, J=2.4 Hz, 1H), 6.73 (d, J=2.4 Hz, 1H), 4.22 (s, 1H), 3.94 (s, 3H), 3.75 (t, J=2.8 Hz, 2H), 3.68-3.57 (m, 4H), 3.59 (t, J=4.8 Hz, 2H), 2.51-2.48 (m, 4H); MS (m/e): 471 (M+1).

Compound 168:
$^1$H NMR (DMSO-d6, 400 MHz): 9.90 (s, 1H), 8.66 (s, 1H), 8.62 (s, 1H), 8.08 (s, 1H), 7.92 (d, J=8.0 Hz, 1H), 7.42-7.37 (m, 2H), 7.21 (d, J=7.2 Hz, 1H), 6.76 (d, J=2.8 Hz, 1H), 6.70 (d, J=2.8 Hz, 1H), 4.24 (s, 1H), 3.94 (s, 3H), 3.71 (t, J=6.0 Hz, 2H), 2.56 (t, J=8.4 Hz, 2H), 2.42 (s, 8H), 2.34 (s, 3H); MS (m/e): 484 (M+1).

Compound 169:
$^1$H NMR (DMSO-d6, 400 MHz): 9.94 (s, 1H), 8.69 (s, 1H), 8.62 (s, 1H), 8.08 (s, 1H), 7.92 (d, J=8.0 Hz, 1H), 7.41-7.35 (m, 2H), 7.21 (d, J=7.6 Hz, 1H), 6.76 (d, J=2.4 Hz, 1H), 6.72 (d, J=2.4 Hz, 1H), 4.24 (s, 1H), 3.93 (s, 3H), 3.72 (t, J=6.8 Hz, 2H), 2.46-2.50 (m, 6H), 1.80 (t, J=7.2 Hz, 2H), 1.00-0.96 (m, 6H); MS (m/e): 471 (M+1).

Compound 170:
$^1$H NMR (DMSO-d6, 400 MHz): 9.92 (s, 1H), 8.67 (s, 1H), 8.65 (s, 1H), 8.07 (s, 1H), 7.91 (d, J=8.8 Hz, 1H), 7.43-7.39 (m, 2H), 7.22 (d, J=7.2 Hz, 1H), 6.78 (s, 2H), 4.49 (d, J=2.0 Hz, 2H), 4.23 (s, 1H), 3.95 (s, 3H); MS (m/e): 396 (M+1).

Example 171

Inhibition of EGFR activity

A431 cells (human epidermoid carcinoma) were seeded in DMEM at 2.5×10$^4$ cells/well in 96-well plates and incubated overnight. The DMEM medium was discarded and the plates were washed with 200 µL of serum-free DMEM medium. After the medium was discarded, 90 µL serum-free DMEM medium was added to each well. The plates were incubated again overnight.

Each test compound was dissolved in DMSO-containing (5%) FBS-free DMEM to prepare a series of solutions at the concentrations of 10, 3.3, 1.1, 0.37, 0.12, 0.04, 0.013, and 0.004 µM. Solutions of compounds at various concentrations were added to wells (10 µL/well) except controls. The plates were incubated under 5% CO$_2$ at 37° C. for 60 min. 10 µL of 200 ng/ml EGF (Biosource, PHG0064) was added to each of the compound-treated wells and some of the controls, followed by incubation under 5% CO$_2$ at 37° C. again for 45 min.

After removal of the medium, to each well was added 100 µL of cell lysis buffer containing 50 mM Tris-Cl (pH 8.0), 0.5 M NaCl and 0.2 mM EDTA, 0.1% Triton X-100, and protease inhibitors (1 µg/ml aprotinin, 0.75 µg/ml leupeptin, 1 µg/ml pepstatin, 1 mM DTT, 500 µM sodium vanadate, and 1 mM PMSF). Note that the protease inhibitors were added immediately before use. The cell lysate was kept at −80° C. overnight 100 µL of 0.5 µg/ml anti-EGFR antibody (Perkin Elmer, AF231) in PBS was added to a 96-well DELFIA yellow plate (Perkin Elmer, AAAND-0001) and incubated at 25° C. overnight with gentle shaking. The medium was discarded and the plate was washed with 200 µL of DELFIA wash buffer 3 times. 200 µL of blocking buffer (PBS buffer containing 0.137 M NaCl, 0.0027 M KCl, 0.01 M Na$_2$PO$_4$-12H$_2$O, 0.0015 M KH$_2$PO$_4$, pH=7.4, and 1% BSA) was added to initiate the blocking procedure. The plate was incubated at 25° C. for 1 h with gentle shaking.

The blocking buffer was discarded and the plate was washed with 200 µL of DELFIA wash buffer (PBS buffer containing 0.05% Tween-20) 3 times. 80 µL of sample diluent (20 mM Tris-Cl/pH7.3, 150 mM NaCl, 0.1% BSA, and 0.05% Tween-20) and 20 µL of the above-obtained cell lysate were then added to each well. Incubation was continued at 25° C. for 1 h with gentle shaking.

The plate was washed again with 200 µL of DELFIA wash buffer 3 times. 100 µL of 0.5 µg/ml Eu-PT66 antibody (Perkin Elmer, AD0040) in DELFIA assay buffer (Perkin Elmer, 1244-106) was added and incubated at 25° C. for 1 h with gentle shaking. After washing with 200 µL of DELFIA wash buffer 3 times, 100 µL of DELFIA enhancement (Perkin Elmer, 4001-0010) was added. The incubation was continued at 25° C. for 30 min with gentle shaking.

Fluorescence was measured at 620 nm by Victor$^3$ (340 nm excitation and 620 nm emission)

Inhibition rates were calculated as follows:

$$\text{Inhibition}(\%) = 100 - \frac{\text{signal of compound well} - \text{signal of cell well}}{\text{signal of EGF well} - \text{signal of cell well}} \times 100\%$$

where "signal of compound well" represents the fluorescence detected from the well which contained cells, a test compound, and EGF; "signal of cell well" represents the fluorescence detected from the well which contained cells, but not a test compound and EGF; and "signal of EGF well" represents the fluorescence detected from the well which contained cells and EGF, but not a test compound.

IC$_{50}$ values (concentration required to inhibit EGFR activity by 50%) were subsequently calculated using the XL-Fit 2.0 software.

The results show that all of Compounds 1-170 inhibited EGFR activity. Their IC$_{50}$ values ranged from 0.001 µM to 10 µM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention can be made and used to practice this invention. Thus, other embodiments are also within the claims.

What is claimed is:

1. A compound of the following formula:

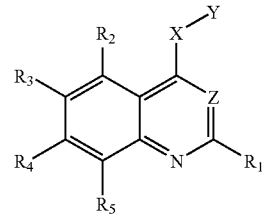

and/or a pharmaceutically acceptable salt thereof, in which
each of R$_1$, R$_2$, and R$_5$, independently, is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl;

one of R$_3$ and R$_4$ is

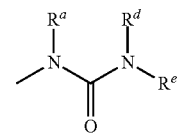

in which R$^a$ is H, alkyl, alkenyl, alkynyl, cycloalkyl, heterocycloalkyl, aryl, or heteroaryl; and each of R$^d$ and R$^e$, independently, is H, alkyl, alkenyl, or alkynyl, provided that R$^d$ and R$^e$ are not H simultaneously;
or R$^d$ and R$^e$, together with the nitrogen to which they are attached, form a 3-12 membered saturated, unsaturated, or aromatic ring containing 1-3 heteroatoms selected from N, O, and S; and
the other of R$_3$ and R$_4$ is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl;
X is NR$^f$, wherein R$^f$ is H, alkyl, alkenyl, alkynyl, aryl, cycloalkyl, heterocycloalkyl, heteroaryl, alkylcarbonyl, alkoxycarbonyl, aminocarbonyl, or aminosulfonyl;
Y is phenyl optionally substituted with akynyl, or optionally fused with 3-8 membered ring; and
Z is N.

2. The compound of claim 1, and/or a pharmaceutically acceptable salt thereof, wherein one of R$_3$ and R$_4$ is

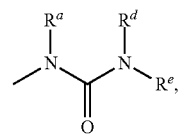

in which R$^a$ is H, alkyl, alkenyl, alkynyl, cycloalkyl, heterocycloalkyl, aryl, or heteroaryl; and each of R$^d$ and R$^e$, independently, is H, alkyl, alkenyl, or alkynyl, provided that R$^d$ and R$^e$ are not H simultaneously.

3. The compound of claim 1, and/or a pharmaceutically acceptable salt thereof, wherein one of R$_3$ and R$_4$ is

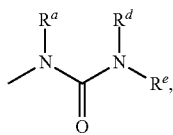

in which $R^a$ is H, alkyl, alkenyl, or alkynyl; and $R^d$ and $R^e$, together with the nitrogen to which they are attached, form a 3-12 membered saturated, unsaturated, or aromatic ring containing 1-3 heteroatoms selected from N, O, and S.

4. The compound of claim 1, and/or a pharmaceutically acceptable salt thereof, wherein X is NH or N—CH$_3$.

5. The compound of claim 4, and/or a pharmaceutically acceptable salt thereof, wherein Y is

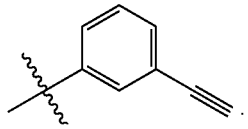 [SMILES: *c1cccc(C#C)c1]

6. The compound of claim 1, and/or a pharmaceutically acceptable salt thereof, wherein Y is

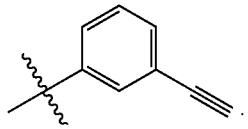 [SMILES: *c1cccc(C#C)c1]

7. The compound of claim 6, and/or a pharmaceutically acceptable salt thereof, wherein one of R$_3$ and R$_4$ is

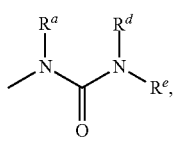

in which $R^a$ is H, alkyl, alkenyl, alkynyl, cycloalkyl, heterocycloalkyl, aryl, or heteroaryl; and each of $R^d$ and $R^e$, independently, is H, alkyl, alkenyl, or alkynyl, provided that $R^d$ and $R^e$ are not H simultaneously.

8. The compound of claim 6, and/or a pharmaceutically acceptable salt thereof, wherein one of R$_3$ and R$_4$ is

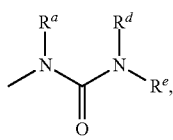

in which $R^a$ is H, alkyl, alkenyl, or alkynyl; and $R^d$ and $R^e$, together with the nitrogen to which they are attached, form a 3-12 membered saturated, unsaturated, or aromatic ring containing 1-3 heteroatoms selected from N, O, and S.

9. A compound selected from

Compound 1

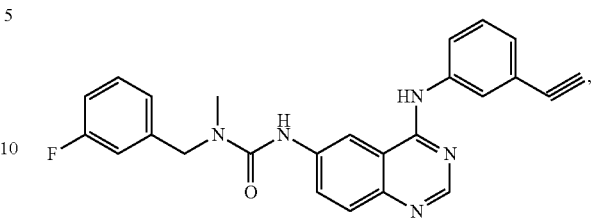

Compound 2

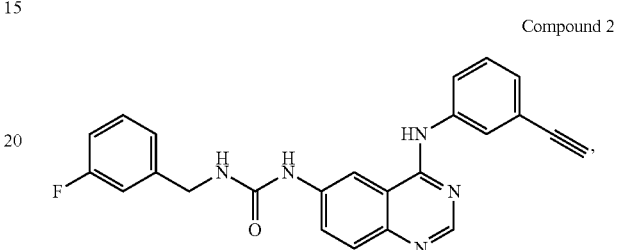

Compound 3

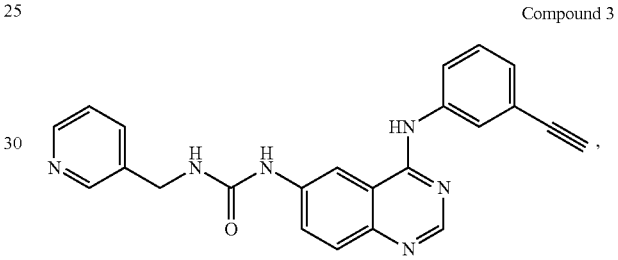

Compound 4

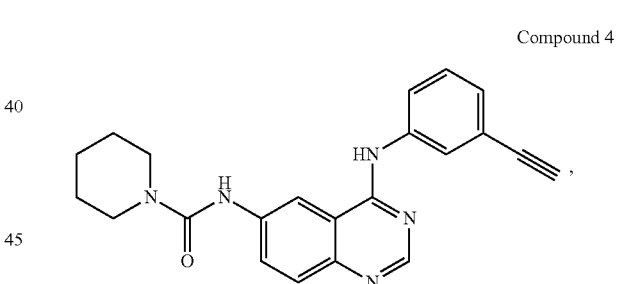

Compound 5

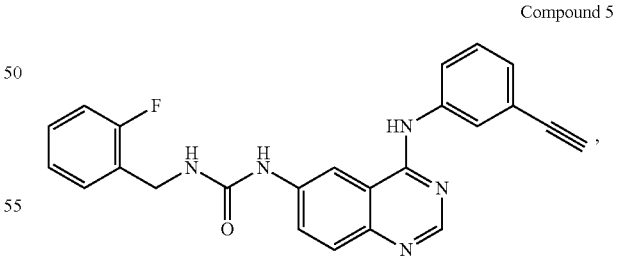

Compound 6

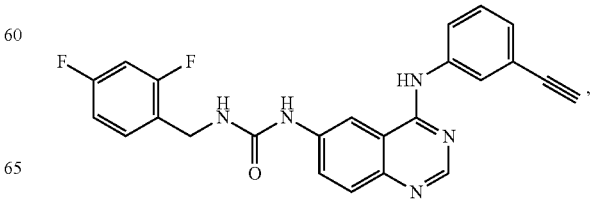

-continued
Compound 7
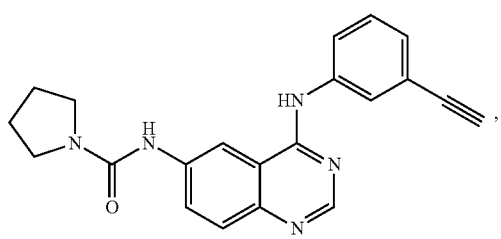
Compound 8
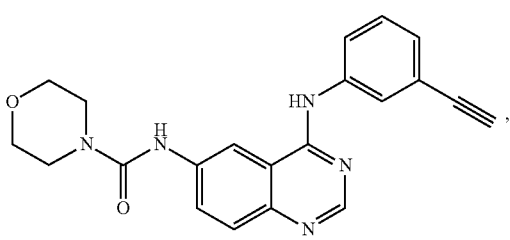
Compound 9
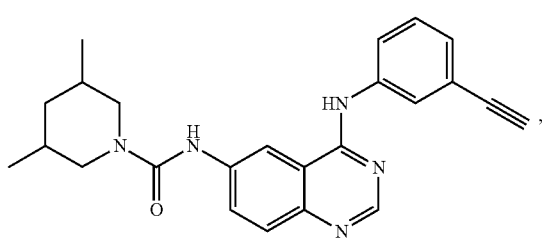
Compound 10
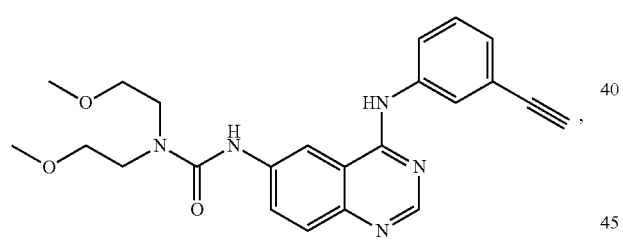
Compound 11
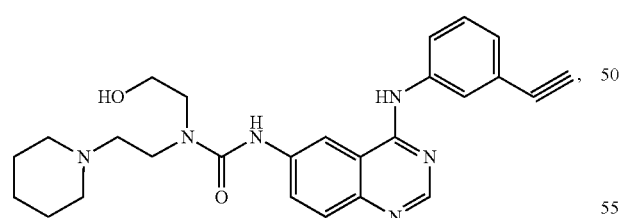
Compound 12
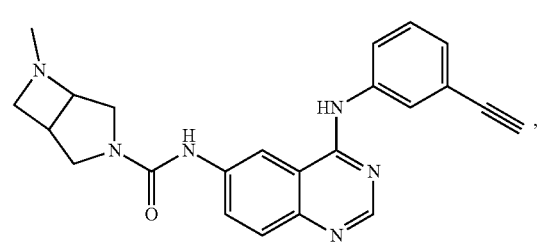
-continued
Compound 13
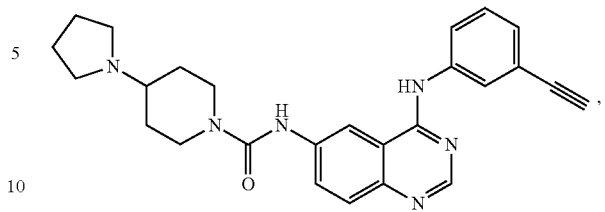
Compound 14
Compound 15
Compound 16
Compound 17
Compound 18
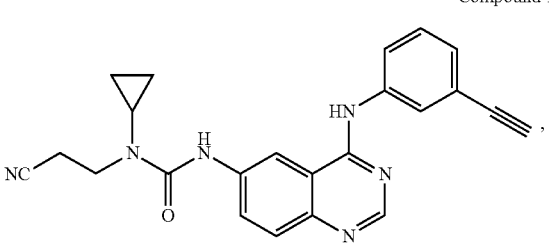

Compound 19
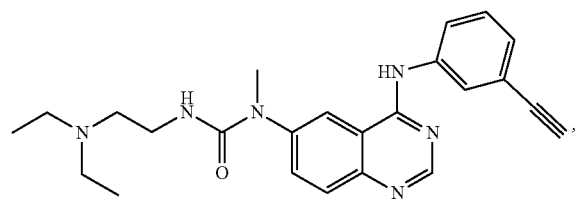
Compound 20
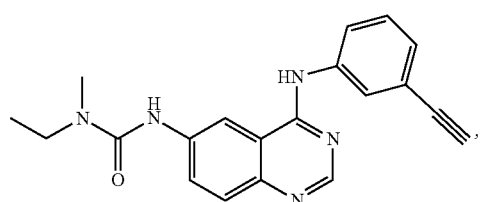
Compound 21
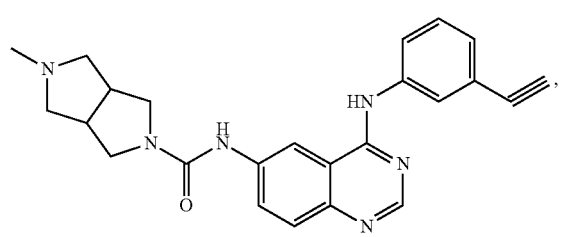
Compound 25
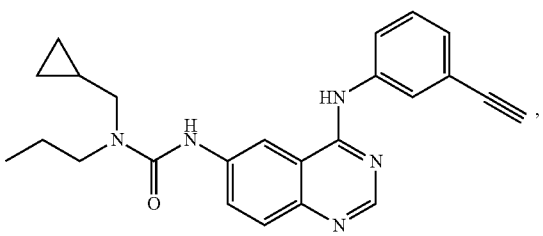
Compound 26
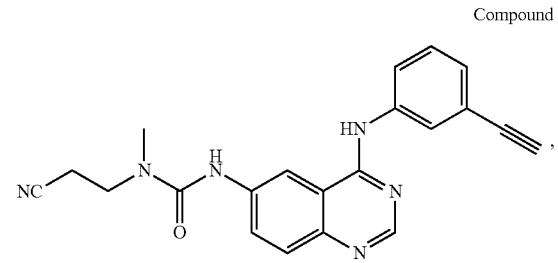
Compound 27
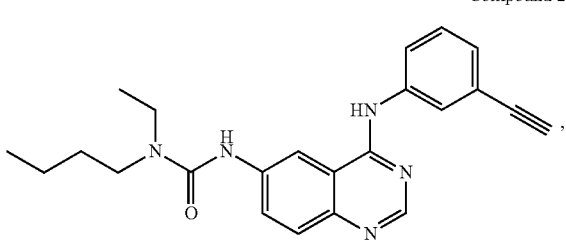
Compound 22
Compound 23
Compound 28
Compound 29
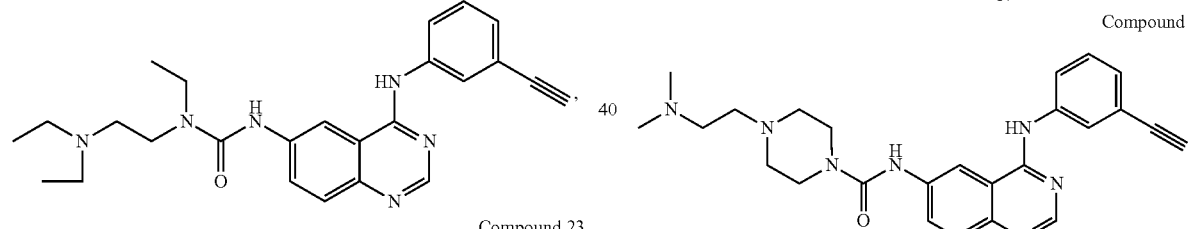
Compound 24
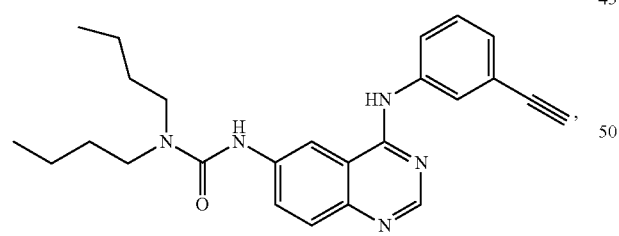
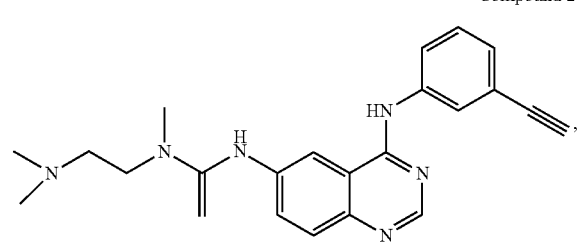
Compound 30
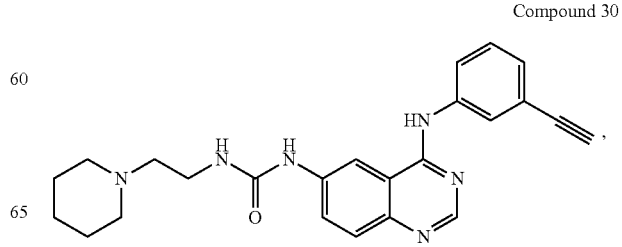

Compound 31
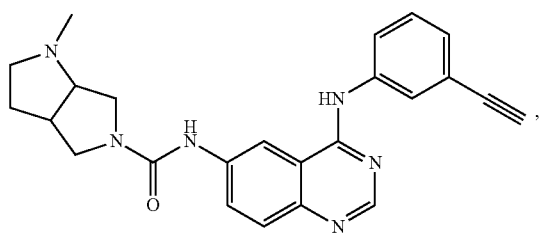
Compound 32
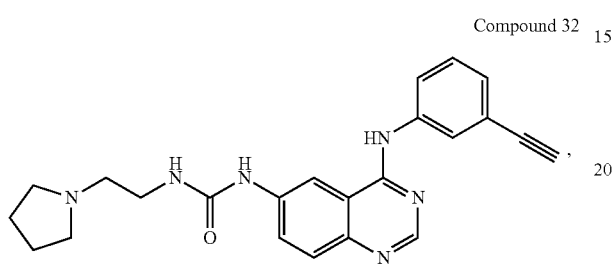
Compound 33
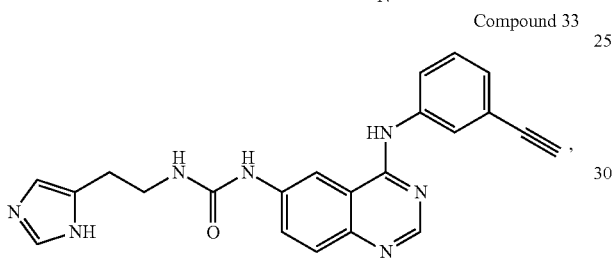
Compound 34
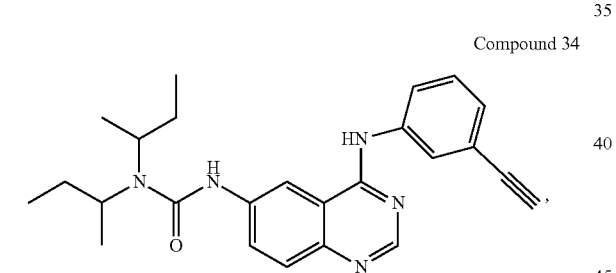
Compound 35
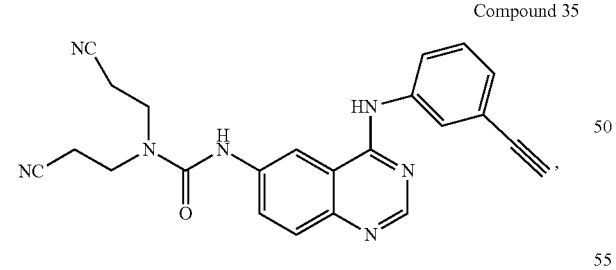
Compound 36
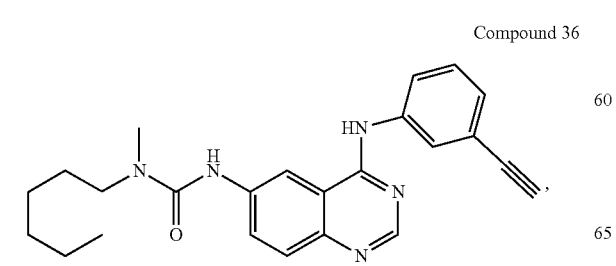
Compound 37
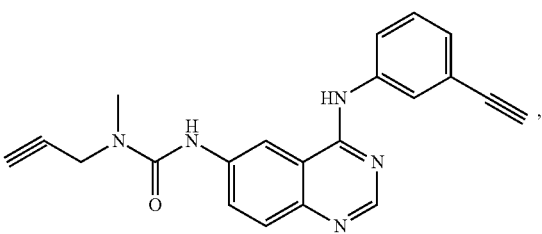
Compound 38
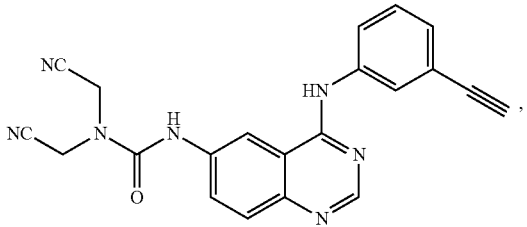
Compound 39
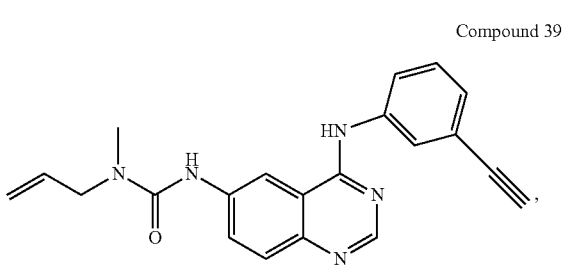
Compound 40
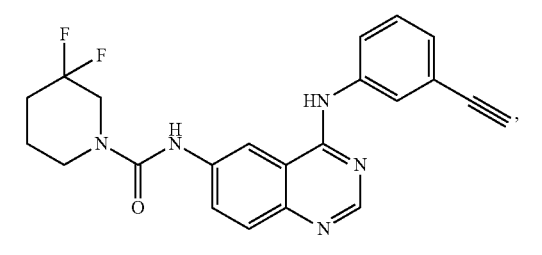
Compound 41
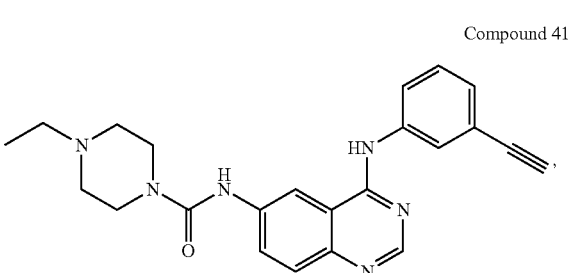
Compound 42
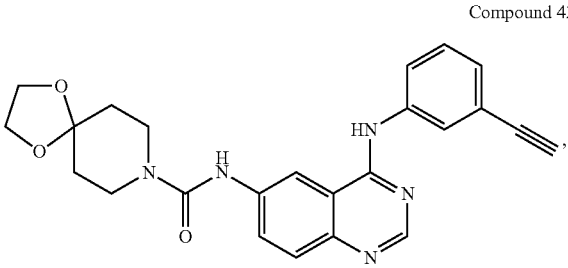

Compound 43
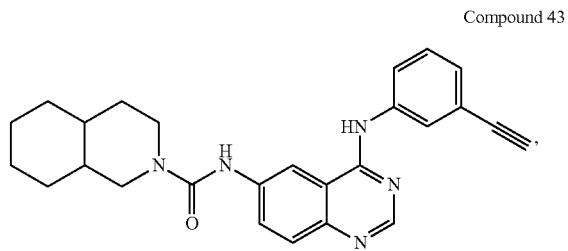
Compound 49
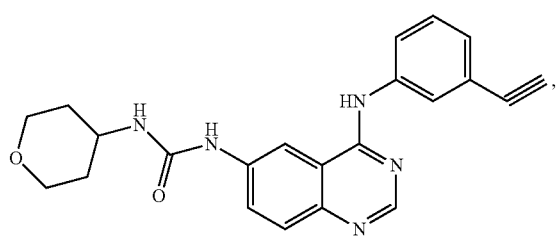
Compound 44
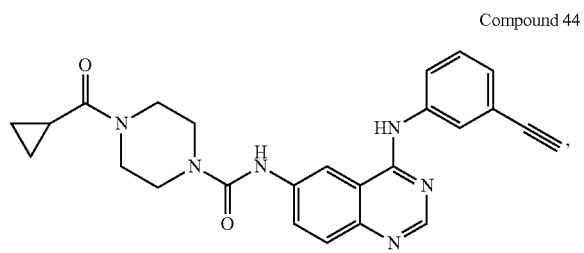
Compound 50
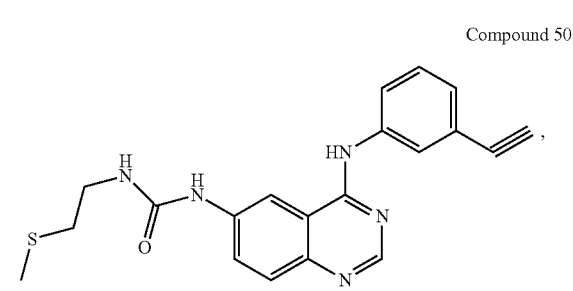
Compound 45
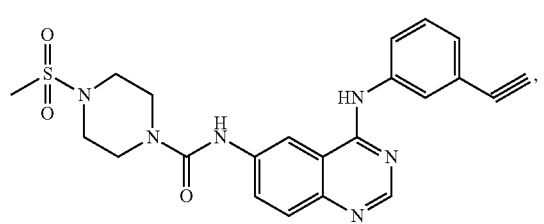
Compound 51
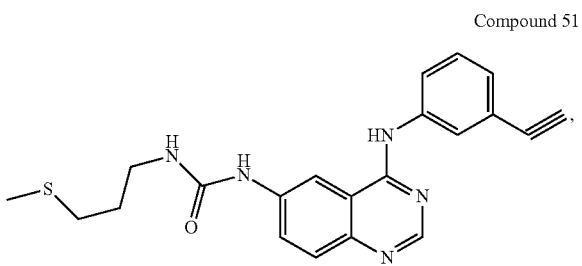
Compound 46
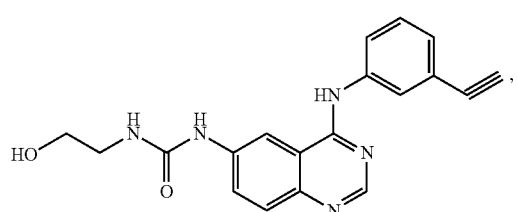
Compound 52
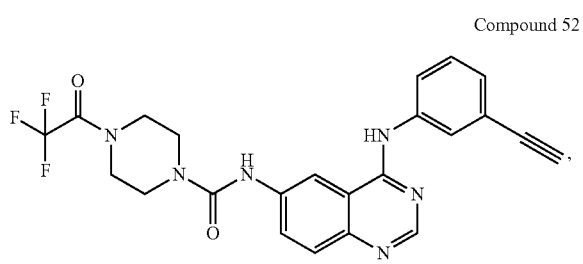
Compound 47
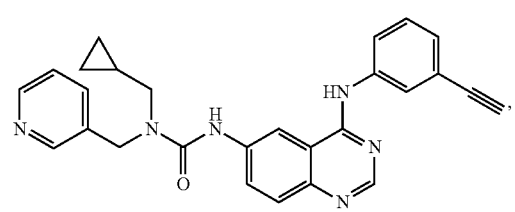
Compound 53
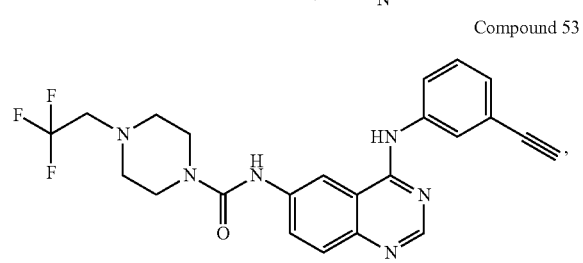
Compound 48
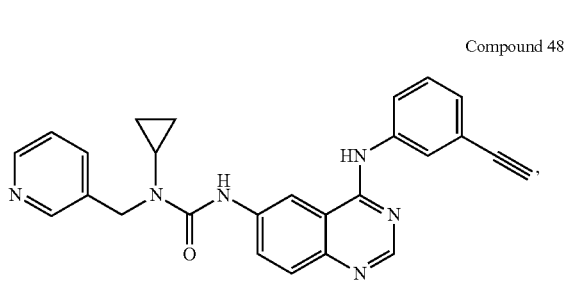
Compound 54
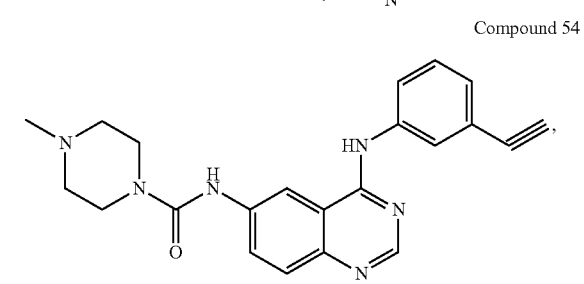

Compound 55
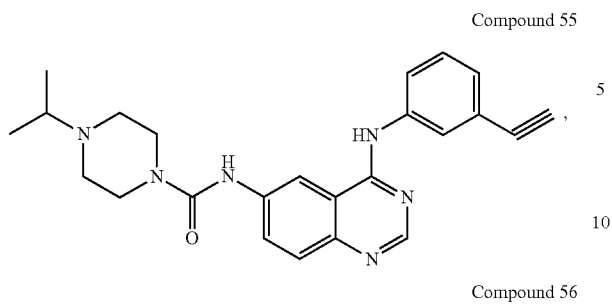
Compound 56
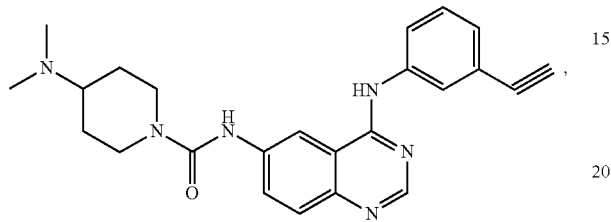
Compound 57
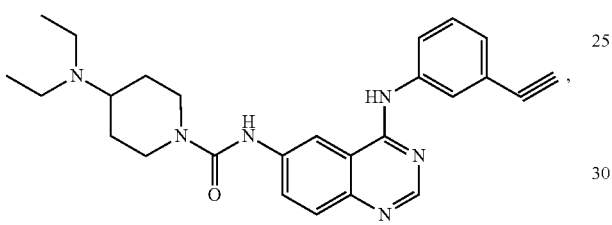
Compound 58
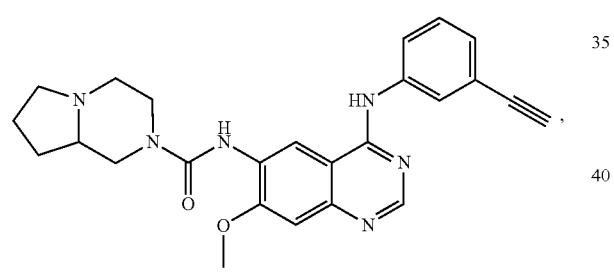
Compound 59
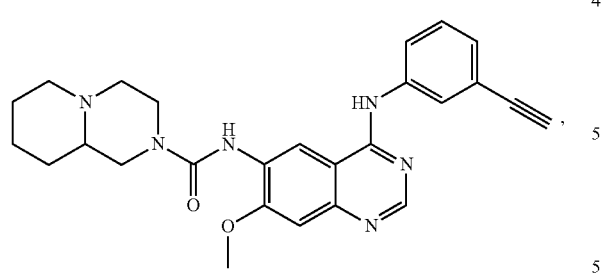
Compound 60
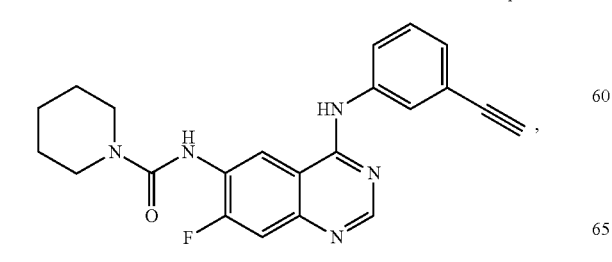
Compound 61
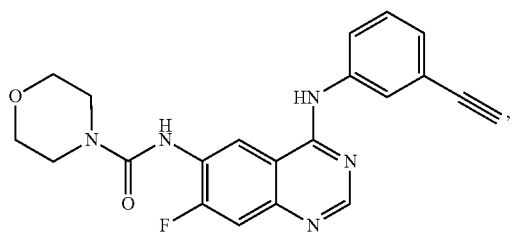
Compound 62
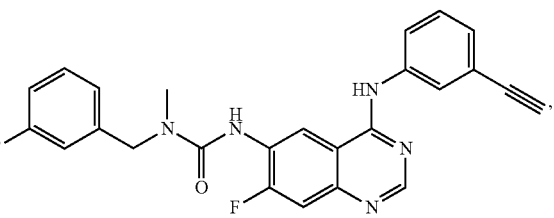
Compound 63
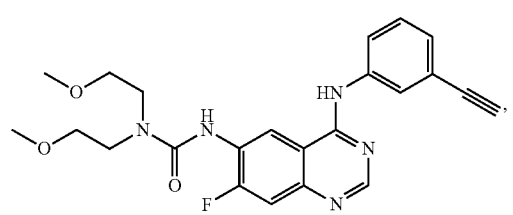
Compound 64
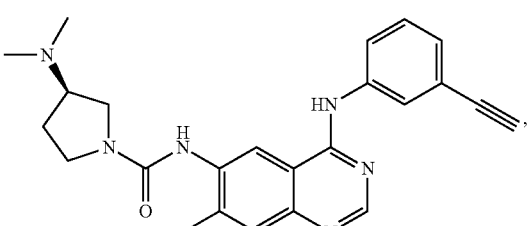
Compound 65
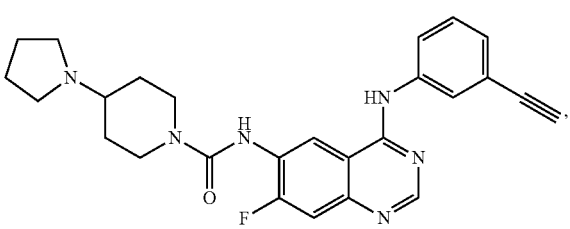
Compound 66
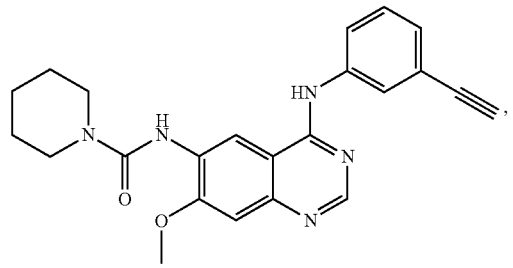

Compound 67
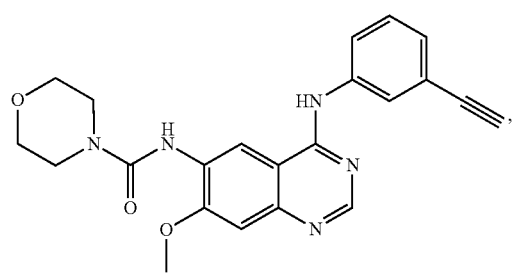
Compound 72
Compound 68
Compound 73
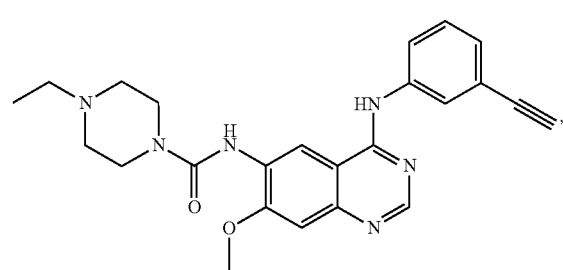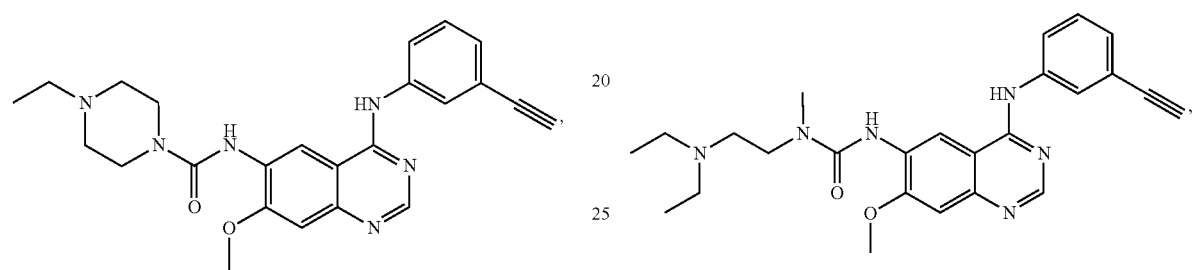
Compound 69
Compound 74
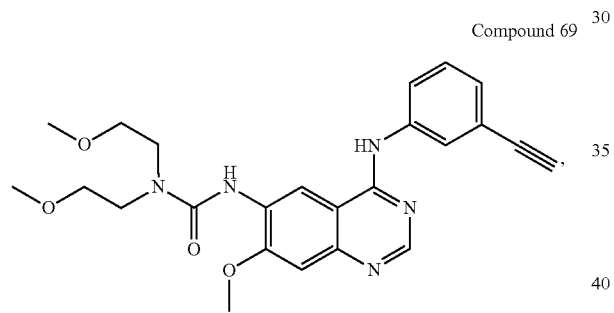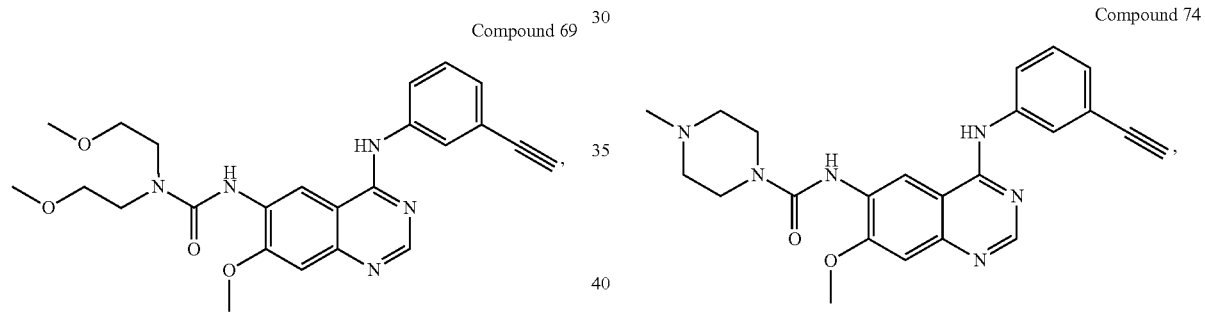
Compound 70
Compound 75
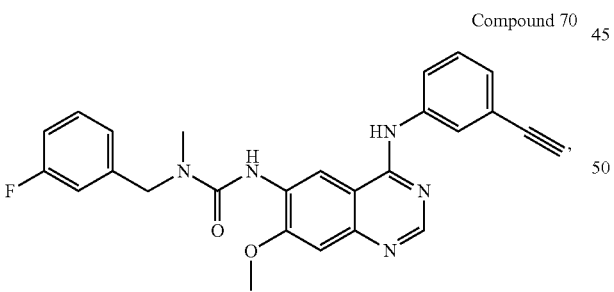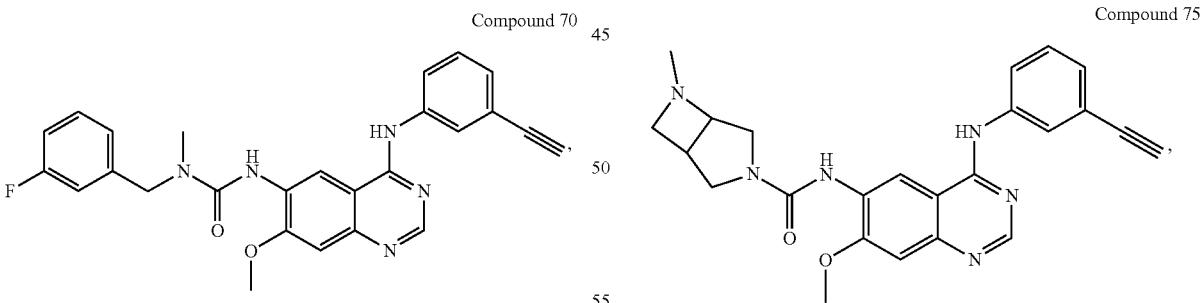
Compound 71
Compound 76
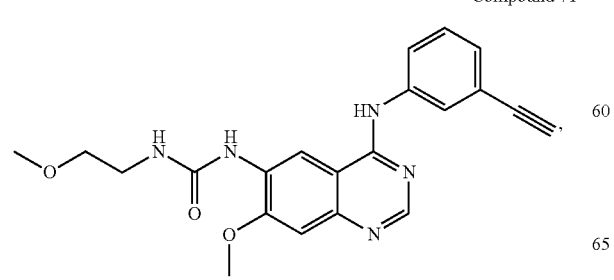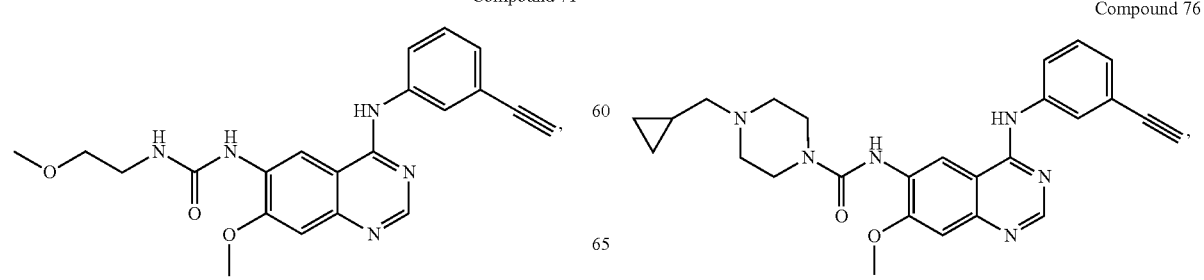

Compound 77
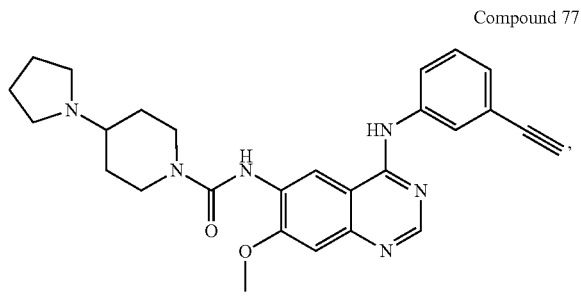
Compound 78
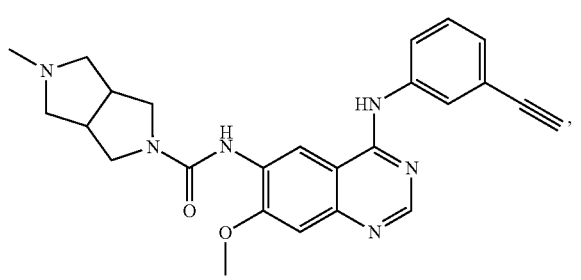
Compound 79
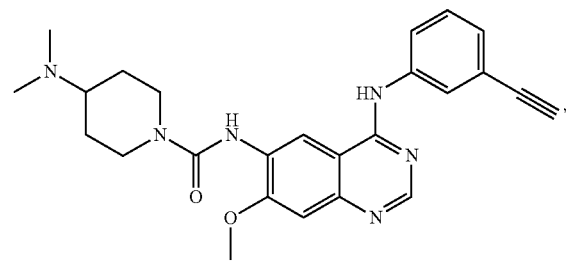
Compound 80
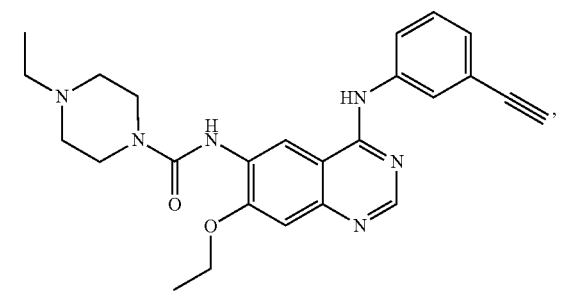
Compound 84
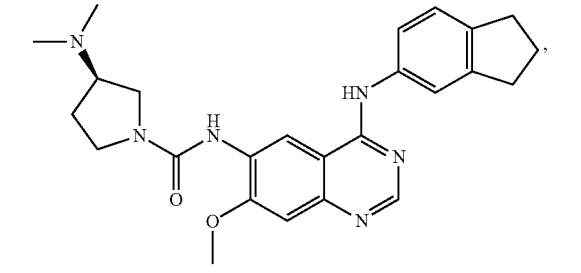
Compound 85
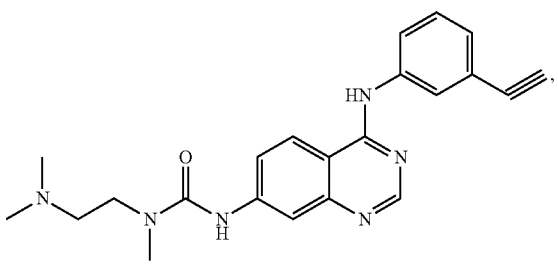
Compound 86
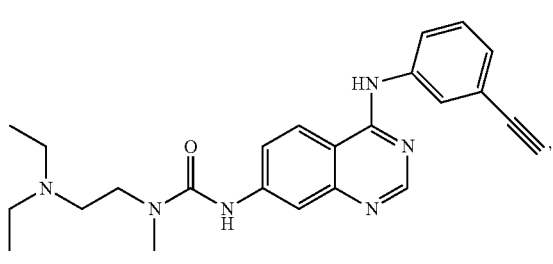
Compound 87
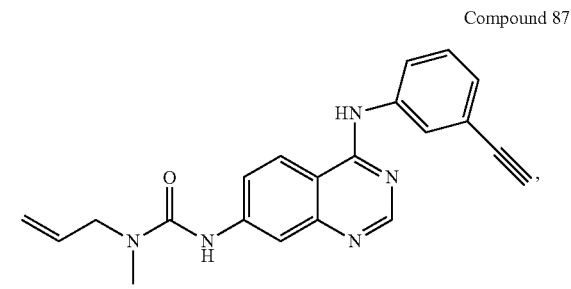
Compound 88
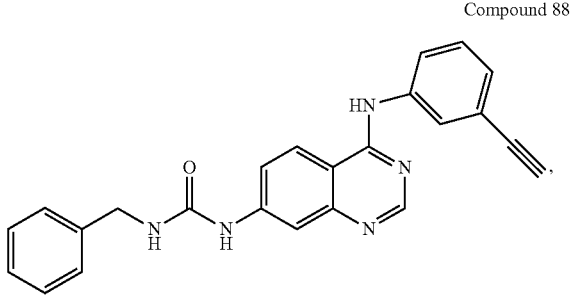
Compound 89
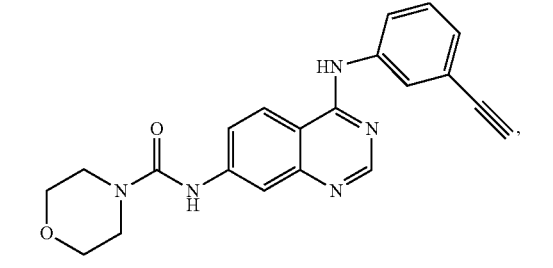

-continued

Compound 90

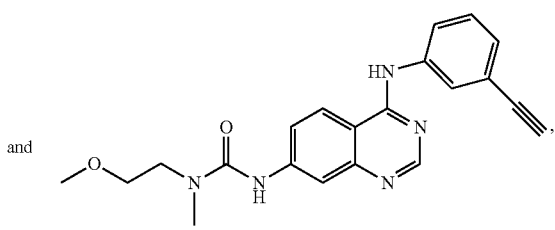 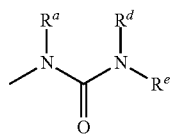

and and/or a pharmaceutically acceptable salt thereof.

10. A pharmaceutical composition, comprising a compound of the following formula:

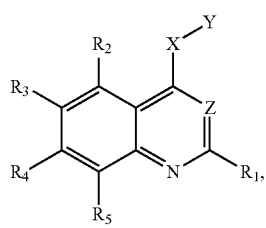

and/or a pharmaceutically acceptable salt thereof, and a pharmaceutically acceptable carrier thereof, in which each of $R_1$, $R_2$, and $R_5$, independently, is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl;

one of $R_3$ and $R_4$ is in which $R^a$ is H, alkyl, alkenyl, alkynyl, cycloalkyl, heterocycloalkyl, aryl, or heteroaryl; and each of $R^d$ and $R^e$, independently, is H, alkyl, alkenyl, or alkynyl, provided that $R^d$ and $R^e$ are not H simultaneously;

or $R^d$ and $R^e$, together with the nitrogen to which they are attached, form a 3-12 membered saturated, unsaturated, or aromatic ring containing 1-3 heteroatoms selected from N, O, and S; and the other of $R_3$ and $R_4$ is H, halo, nitro, amino, cyano, hydroxy, alkyl, alkenyl, alkynyl, aryl, cycloalkyl, heterocycloalkyl, heteroaryl, alkoxy, alkylthio, alkylcarbonyl, carboxy, alkoxycarbonyl, carbonylamino, sulfonylamino, aminocarbonyl, or aminosulfonyl;

X is $NR^f$, wherein $R^f$ is H, alkyl, alkenyl, alkynyl, aryl, cycloalkyl, heterocycloalkyl, heteroaryl, alkylcarbonyl, alkoxycarbonyl, aminocarbonyl, or aminosulfonyl;

Y is phenyl optionally substituted with akynyl, or optionally fused with 3-8 membered ring; and Z is N.

* * * * *